(12) United States Patent
Kumar et al.

(10) Patent No.: US 8,227,594 B2
(45) Date of Patent: Jul. 24, 2012

(54) ANTIVIRAL NUCLEOSIDES

(75) Inventors: Rakesh Kumar, Edmonton (CA); Babita Agrawal, Edmonton (CA); D. Lorne J. Tyrrell, Edmonton (CA)

(73) Assignee: Rakesh Kumar, Edmonton, Alberta (CA)

(*) Notice: Subject to any disclaimer, the term of this patent is extended or adjusted under 35 U.S.C. 154(b) by 441 days.

(21) Appl. No.: 12/467,939

(22) Filed: May 18, 2009

(65) Prior Publication Data

US 2010/0130440 A1    May 27, 2010

Related U.S. Application Data

(62) Division of application No. 10/477,763, filed as application No. PCT/CA02/00718 on May 17, 2002, now Pat. No. 7,589,077.

(60) Provisional application No. 60/291,960, filed on May 18, 2001.

(51) Int. Cl.
*A61K 31/7068* (2006.01)
*A61K 31/7072* (2006.01)

(52) U.S. Cl. ............... 536/26.8; 536/28.51; 536/28.52; 536/28.54; 536/28.55; 514/49

(58) Field of Classification Search ............... None
See application file for complete search history.

(56) References Cited

U.S. PATENT DOCUMENTS

| 3,221,010 | A | * | 11/1965 | Duschinsky | ............... | 536/28.52 |
| 6,034,087 | A | | 3/2000 | Kim et al. | | |
| 6,200,952 | B1 | * | 3/2001 | Horwitz | ............... | 514/4.3 |

FOREIGN PATENT DOCUMENTS

| EP | 0409575 | | 1/1991 |
| EP | 0507188 | | 10/1992 |
| WO | 199215308 | | 9/1992 |
| WO | 199414831 | | 7/1994 |
| WO | WO94/26761 | * | 11/1994 |
| WO | 199640164 | | 12/1996 |
| WO | 0026225 | | 5/2000 |

OTHER PUBLICATIONS

Chang et al., "Iodination of 2'-Deoxycytidine and Related Substances" Journal of Medicinal Chemistry (1963) vol. 6 No. 4 pp. 428-430.*
Cohen et al., "Studies on the biosynthesis of bacterial and viral pyrimidines. IV. Utilization of pyrimidine bases and nucleosides by bacterial mutants" Journal of Biological Chemistry (1957) vol. 228 No. 2 pp. 611-619.*
Codington et al., "Nucleosides. XXX. Synthesis of 2-deoxy-2-fluoro-D-ribose" Carbohydrate Research (1966) vol. 1 No. 6, abstract.*
Ezra et al., "Influence of Uracil Photohydrate Formation on the Conformational Properties of Heterodinucleoside Monophosphates" Biopolymers (1980) vol. 19 pp. 1983-2002.*

Visser et al., "Reaction of Acetyl Hypofluorite with Pyrimidines. Part 3.' Synthesis, Stereochemistry, and Properties of 5-Fluoro-5,6-dihydropyrimidine Nucleosides" J. Chem. Soc. Perkin Transactions I (1988) p. 2547-2554.*
Jansen et al., The Degradation of the Antitumor Agent Gemcitabine Hydrochloride in an Acidic Aqueous Solution at pH 3.2 and Identification of Degradation Products Journal of Pharmaceutical Sciences (2000) vol. 89 No. 7 pp. 885-891.*
Cadet et al., "1-(2-Deoxy-beta-D-erythro-pentopyranosyl)uracil and its alpha-D-anomer" published in Nucleic Acid Chemistry (1978) by Wiley-Interscience, pp. 311-315.*
Nucci et al., "Interaction of the High-Affinity Inhibitor Tetrahydro-dUMP with the Allosteric Enzyme Deoxycytidine Aminohydrolase" Archives of Biochemistry and Biophysics (1994) vol. 310 No. 1 pp. 49-53.*
Lin et al., "Anti-Human Immunodeficiency Virus Agent 3'-Azido-3'-Deoxythymidine Inhibits Replication of Epstein-Barr Virus" Antimicrobial Agents and Chemotherapy (Feb. 1988) vol. 32 No. 2 p. 265-267.*
Westphal et al., Activation of Lytic Epstein-Barr Virus (EBV) Infection by Radiation and Sodium Butyrate in Vitro and in Vivo: A Potential Method for Treating EBV-positive Malignancies Cancer Research (2000) vol. 60 pp. 5781-5788.*
Fahr et al., "Die kinetische Untersuchung der Beeinflussung des Zerfalls der bei der UV—Bestrahlung von Nucleinsaure-Bestandteilen entstehenden 6-Hydroxy-dihydrouracil-Derivate durch den Substituenten am N-1-Atom" Zeitschrift Fur Naturforschung. Teil B: Chemie, Bio (1967) vol. 22 No. 12 pp. 1256-1261.*
Allen, L.B. et al. "Acyclic pyrimidine nucleoside analogues: Influence on grown of L5178y mouse lymphoma cells and antiherpes activity in KB cells" Chemotherapy, vol. 31 (1985) pp. 151-159.
Barvian, M.R. et al., "Independent generation of 5.6-dihydrothmid-5-yl and investigation of its ability to effect nucleic acid strand scission via hydrogen atom abstraction"; J. Org. Chem. vol. 60 (1995) pp. 1916-1917.
Cadet, J. et al., "Preparation, isomerisation et configuration absolue des "hydrates" de thymidine"; Tetrahedron (1977) vol. 33: pp. 1603-1607.
Cadet, J. et al., "O6,5'-cyclo-5,6-dihydro-2'-deoxyuridine. Novel deoxyuridine photoproducts"; J. Am Chem. Soc. (1978); vol. 100: pp. 6715-6720.
Chemical Abstracts Registry Entry 3056-17-5 (Stavudine) Entered into Chemical Abstracts on Nov. 16, 1984.
Deinstag et al., "Lamivdine as Initial Treatment for Chronic Hepatitis B in the United States" ; The New England Journal of Medicine (1999) vol. 341, No. 7: pp. 1256-1263. Hirota K. et al., "Nucleosides, Part 5. Isolation and characterization of the stable cyclic adducts, (5R, 6S)- and (5S,6S)-bromoO6-5'-cyclo-5,6-dihydropyrimidine nucleosides"1 J. Chem. Soc. Perkin Trans. 1, (1988) pp. 2547-2554.
Inoue, H. et al., "Synthesis of 6,5'-S and 6,5'-N-cyclouridines (Nucleosides and Nucleotides. XXII)" Chem. Pharm. Bull, (1978) vol. 26: pp. 2664-2667.

(Continued)

Primary Examiner — Eric S Olson
(74) Attorney, Agent, or Firm — Bozicevic, Field & Francis LLP; Bret E. Field

(57) ABSTRACT

Disclosed are nucleosides which are useful in diagnosing and treating viral infections, for example, infections caused by hepatitis B virus (HBV), and herpes viruses including Epstein Barr virus.

18 Claims, No Drawings

OTHER PUBLICATIONS

Jansen P.J., et al., The degradation of the antitumor agent gemcitabine hydrochloride in an acidic aqueous solution at pH 3.2 and identification of degradation products: The Journal of Pharmaceutical Sciences (2000) vol. 89: pp. 885-891.

Kameyama K., et al., "Reaction of nucleosides with lead tetra-acetate: facile formation of cyclonucleosides" J. Chem. Soc., Chem. Commun. (1994) pp. 1658-1659.

Keppeler K. et al., "Synthesis and antiviral activity of acyclic derivatives of 5-ethyl-2'-deoxyuridine" Arch. Pharm. (Weinheim); (1986): pp. 360-365.

Kumar, R., et al., "Novel 5-vinyl pyrimidine nucleosides with potent anti-hepatitis B viruy activity" Bioorganic & Medicinal Chemistry Letters, (2001) vol. 11: pp. 2917-2920.

Kumar R., et al., "Synthesis and antiviral (HIV-1, HBV) activities-of 5-halo-6-methoxy(or azido)-5,6-dihydro-3'—deoxythymi dine diastereomers. Potential prodrugs to 3'-flouro-3'-deoxythymidine" J. Med. Chem. (1994) vol. 37: pp. 3554-3560.

Kumar R., et al., "Synthesis and antiviral activity of novel acyclic nucleoside analogues of 5-/1-azido-2-haloethyl) uracils" J. Med Chem. (2001) vol. 44: pp. 4225-4229.

Kumar R., et at., "Design and synthesis of novel 5-substituted acyclic pyrimidine nucleosides as potent and selective inhibitors of hepatitis B virus" J. Med. Chem (2002) vol. 45: pp. 2032-2040.

Lipkin, D, et al., "The iodination of thymidine. A synthesis of O6,5'-cyclothymidine" J. Am. Chem. Soc. (1971) vol. 93: pp. 3309-3310.

Lipschultz B.H., et al., "A novel route to pyrimidine nucleosides via intramolecular couplings of bases with 2'—deoxyribosides: quick and sterospecific . . . but with a twist" Synthesis (1994) pp. 1476-1484.

Lipschultz et al., "A novel route to the anti-HIV Nucleoside d4T" Tetrahedron Letters (1995) vol. 36, No. 16: pp. 2711-2712.

Lovett, E.G., et al., "Mass spectroscopy of pyrimidine cyclonucleosides" J. Am. Chem. Soc. (1973) vol. 95: pp. 2312-2320.

Mar et al., "Some nucleosides analogs with anti-human immunodeficiency virus activity inhibit replication of Epstein-Barr virus" Antiviral Research (1995) vol. 28: pp. 1-11.

Maruyama et al., "Halogenation of Pyrimidine 6-O-Cyclonucleosides" J. Org. Chem (1983) vol. 48: pp. 2719-2723.

McKinnell D. et al., "The Synthesis, Structure and Properties of a 1,2-Dihydropyrimidin-2-one formed by UV-Irradiation of 5-t-Buty1-1-Methyluracil" Tetrahedron, Elsevier Science Publishers, Amsterdam NL (1996) Jul. 22, 1996; vol. 52, No. 30: pp. 10159-10168.

Mendiratta, A., et al., "Structure-activity on antiviral 6-vinylpyrimidine nucleoside analogs using Wiener's topological index" J. Chem. Inf. Comput. Sci. (1994) vol. 34: pp. 867-871.

Merck Research Laboratories, "The Merck Manual of Diagnosis and Therapy, Seventeenth Edition" (1999) edited by Beers and Berkow; p. 1312 and p. 1322.

Mortura M. et al., Synthesis, lipophiticity and anti-HIV activity of a new brominated analog of zidovudine Nucleosides & Nucleotides (1999) vol. 18: pp. 337-351.

Ogilvie K.K., et al., "Uracil analogues of the acyclonucleoside 9-[[2-hydroxy-1-(hydroxymethyl)ethoxy)-methyl] guanine (BIOLF-62)" Can. J. Chem. (1984) vol. 62: pp. 16-21.

Orr G. F., et al., "Inhibition of uridine phosphorylase: Synthesis and struture-activity relationships of aryl-substituted 5-benzyluracils" J. Med. Chem (1995) vol. 38: pp. 3850-3856.

Park J. S., et al., "Enzyme affinity of the 5,6-dihydro derivatives of the substrate and product of thymidylate synthetase catalysis" J. Med. Chem. (1979) vol. 22: pp. 319-321.

Phadatare, S., et al., "Synthesis of N1-(4-hydroxy-1,2-butydien-1-yl)thymine, an analogue of 3'-deoxythimidine" J. Org. Chem. (1989) vol. 54: pp. 3675-3679.

Pragnacharyulu P.V.P. et al., "Diastereomeric 5,6—dihydrothymidines" J. Org. Chem. (1995) vol. 60: pp. 3096-3099.

Pragnacharyulu P.V.P. et al;; Unprecedented chlorination of 2,2 ?-anhydro-5,6-dihydropyrimidine nucleosides during DDQ oxidation: Tetrahedron Letters, Elsevier Science Publishers, Amsterdam NL (1997) May 26, 1997; vol. 38, No. 21: pp. 3683-3686.

Raez et al., Treatment of AIDS-Related Primary Central Nervous System Lymphoma with Zidovudine, Ganciclovir, and Interleuken 2 AIDS Research and Human Retroviruses (1999) vol. 15, No. 8: pp. 713-719.

Reefschlager J. et al., "Anti-herpes simplex virus and cytostatic activity of some new 5-substituted 1-(4-hydroxybutyl)- and 1-(2-hydroxyethoxymethyl) uracil nucleoside analogues" Acta Virol. (1985) vol. 29: pp. 185-193.

Sako M. et al., "A facile synthesis of 5'-O,6-cyclo-5,5-dihalogeno-5,6-dihydropyr imidine nucleosides" Synthesis (1987) pp. 829-831.

Sekine et al., "Facile Synthesis of 3'-0-Methylthymidine and 3'-Deoxythymidine and Related Deoxygenated Thymidine Derivative: A New Method for Selective Deoxygenation of Secondary Hydroxy Groups" Journal of Organic Chem. (1990) vol. 55: pp. 924-928.

Silverman, R., "The Organic Chemistry of Drug Design and Drug Action" Academic Press (1992) pp. 19-21 and 352-397.

Streicher W., et al., "Synthesis of New Acyclic Nucleoside Analogs and their Antiviral Properties Against Herpes Simplex Virus" Chemica Scripta, Press Syndicate of the Cambridge University (1986) vol. 26: pp. 179-183.

Takenaka, K., et al., "Synthesis of 5-ethylpyrimidine nucleoside analogs" J. Heterocyclic Chem. (1997) vol. 34: pp. 669-673.

Ueda, T., et al., "A facile conversion of amino to thiono group in certain nucleobases" Tet. Letters (1971) vol. 27: pp. 2507-2510.

Visser G.W.M., et al., "Reaction of acetyl hypoflourite with pyrimidines. Part 3. Synthesis, stereochemistry, and properties of 5-fluoro-5,6-dihydropyrimidine nucleosides" J. Chem. Soc. Perkin Trans. (1988) pp. 2547-2554.

* cited by examiner

ANTIVIRAL NUCLEOSIDES

This application is a divisional of U.S. patent application Ser. No. 10/447,763 filed Jun. 29, 2004, now U.S. Pat. No. 7,589,077, which is a national stage application of PCT/CA02/00718 filed May 17, 2002, which claims the benefit of U.S. Provisional Application No. 60/291,960 filed May 18, 2011, all of which are incorporated by reference herein in their entirety.

FIELD OF THE INVENTION

This invention relates to novel nucleosides with antiviral activities, and methods of preparation and use thereof. The nucleosides are useful medications for the prophylaxis, treatment and diagnosis of various viral infections, for example, infections caused by hepatitis B virus (HBV), herpes viruses such as the Epstein-Barr virus (EBV), herpes simplex virus type 1 (HSV-1), and herpes simplex virus type 2 (HSV-2).

BACKGROUND OF THE INVENTION

There are numerous viral infections which can be treated with various nucleosides. These infections include infections by the human immunodeficiency virus (HIV), hepatitis B virus (HBV), hepatitis C virus, human cytomegalovirus (HCMV), Herpes Simplex I virus (HSV-1), Herpes Simplex virus type-2 (HSV-2), and Varicella Zoster virus (VZV).

Hepatitis B virus (HBV) is a causative agent of acute and chronic hepatitis. HBV infections are the world's ninth leading cause of death. HBV infection often leads to acute hepatitis and liver damage, and causes abdominal pain, jaundice, and elevated blood levels of certain enzymes. HBV can cause fulminant hepatitis, a rapidly progressive form of the disease in which massive sections of the liver are destroyed. Many patients recover from acute viral hepatitis, but certain other patients have high levels of viral antigen which persist in the blood for an extended, or indefinite, period, causing a chronic infection. Chronic infections can lead to chronic persistent hepatitis. Chronic persistent hepatitis can cause fatigue, liver damage, cirrhosis of the liver, and hepatocellular carcinoma, a primary liver cancer. The epidemiology of HBV is in fact very similar to that of acquired immunodeficiency syndrome. Accordingly, HBV infection is common among patients with AIDS or HIV-associated infections. However, HBV is more contagious than HIV.

HBV infection is an increasingly serious problem among the homo- and heterosexual population, intravenous drug users, organ transplant recipients, and blood transfusion patients. New infection with HBV can be prevented by vaccination. However, the present vaccination is not effective for the approximately 350 million chronic carriers worldwide. It has been observed that suppression or eradication of the replication of HBV in the liver leads to improved liver pathology and decreased progression to liver cirrhosis and hepatocellular carcinoma.

The current therapy approved in the United States for treating chronic hepatitis B infection is alpha interferon, which is far from ideal. According to the American Liver Foundation and the International Hepatitis Foundation, patients with conditions such as advanced hepatitis, HIV coinfection, drug abuse or others are not eligible for this treatment, resulting in less than 50% of chronic carriers obtaining this therapy. Of these patients, only about 40% respond to the treatment. Many of these patients also relapse after treatment is stopped, and only about 30% of the patients show a long term benefit. Viral disappearance is only seen in about 10-20% of the treated patients. These data suggest that there is an extremely low response rate in patients treated with alpha interferon. In addition to the low response rate, interferon therapy causes severe side effects such as insomnia, depression, nausea, vomiting, fever and fatigue.

Various nucleosides have also been proposed for use in treating HBV infection. For example, lamivudine (3-TC) is approved; however, virus flare following therapy and increased emergence of resistant viral strains against lamivudine have been recognized in clinical trials with prolonged monotherapy in transplantation and chronic hepatitis patients. In the area of HBV, there is an urgent need to complement existing therapies (for example, with lamivudine) with other therapeutic agents. Accordingly, design and development of new anti-HBV chemotherapeutic agents, for use alone or in combination with other anti-HBV agents, is urgently needed for the management and treatment of chronic HBV infections.

Similar to hepatitis B virus, human immunodeficiency is a retrovirus. Although a number of nucleoside agents are known for HIV, they all don't show activity against hepatitis B virus (REF).

The Epstein-Barr virus (EBV) is a member of the genus Lymphocryptovirus, which belongs to the subfamily gammaherpesviridae. It is notably lymphotropic. EBV has the classic structure of herpes viruses, that is, its double-stranded DNA genome is contained within an icosapentahedral nucleocapsid, which, in turn, is surrounded by a lipid envelope studded with viral glycoproteins. An amorphous tegument protein occupies the space between the envelope and the nucleocapsid.

Human herpes viruses infect and replicate within lymphocytes to some extent, but EBV does so efficiently. Most importantly, the pathogenesis and host responses to infection with EBV are more dependent upon lymphocytic infection than is evident with the other human herpes viruses. EBV is now recognized as a cause of B-cell lymphoproliferative diseases, and has been linked to a variety of other severe and chronic illnesses, including a rare progressive mononucleosis-like syndrome and oral hairy leukoplakia in ADS patients. EBV DNA has been found in some T-cell lymphomas and Hodgkin's tissue samples. EBV has also been associated with autoimmune diseases such as Sjogren's syndrome.

EBV is primarily transmitted through the saliva, although some infections are transmitted by blood transfusion. More than 85% of patients in the acute phases of infectious mononucleosis secrete EBV.

EBV has been associated with cancer. At least two groups of patients are at risk for development of EBV-associated lymphomas: those who have received transplants of kidney, heart, bone marrow, liver, or thymus under the cover of immunosuppressive therapy, and patients with AIDS. EBV-associated cancers include Burkitt's Lymphoma, Hodgkin's disease, non-Hodgkin's lymphoma and Nasopharyngeal Carcinoma.

Several different DNA viruses have been shown to cause tumors in animals. The effect of cancerogenic chemicals on animals can result in activation of latent tumor viruses. It is possible that tumor viruses are involved in human tumors. The most likely human cases known today are leukemias, sarcomas, breast carcinomas, and cervical cancers where herpes viruses are also indicated. This makes the search for selective inhibitors of tumorigenic viruses and their functions an important undertaking in efforts to treat cancers.

There remains a strong need to provide new effective pharmaceutical agents to treat humans infected with herpes-viruses such as EBV. So far there is no effective drug for the treatment of EBV infections.

A variety of nucleosides are known as biologically important nucleosides, and a number of other nucleosides are known as intermediates for preparing these nucleosides. For example, cyclonucleosides have been used as intermediates for preparing halopyrimidine nucleosides. Lipshutz et al., Synthesis, 1476-1484 (1994), discloses forming diastereomeric cyclonucleosides (wherein the C-5'-hydroxyl group is coupled to a pyrimidine base such as thymine to form an ether linkage) as an intermediate for forming certain pyrimidine nucleosides. However, Lipshutz does not disclose or suggest the anti-Epstein Barr virus or anti-hepatitis B virus activity of the cyclonucleosides. Cadet et al., 109(21):6715-6720 (1978), discloses forming cyclic pyrimidine nucleosides as by-products in the irradiation of uracil derivatives. Sako et al., Synthesis, 829-831 (1987), also discloses using cyclonucleosides as intermediates for synthesizing partially modified nucleosides and nucleotides. Maruyama et al., J. Org. Chem., 48:2719-2723 (1983), discloses halogenating pyrimidine 5'-C6-cyclonucleosides to form halopyrimidine nucleosides. Although the halopyrimidine nucleosides are known to be biologically active as antiviral and antitumor agents, the antiviral (Epstein Barr virus, hepatitis B virus) ability of the 5'-C6-cyclonucleosides is neither disclosed nor suggested.

Some of 5,6-dihydro pyrimidine nucleosides are known to possess activity against human immunodeficiency virus, however, the hepatitis B virus and Epstein B virus activity have not been described before. Similarly, acyclic pyrimidine nucleosides have not been shown to possess activity against hepatitis B virus.

Accordingly, it is an object of the present invention to provide compounds and methods for treating viral infections caused by exposure to herpes viruses such as Epstein Barr virus, and Hepatitis B virus. The present invention provides such compounds and methods.

SUMMARY OF THE INVENTION

Compounds and methods for treating viral infections mediated by exposure to herpes viruses, such as Epstein Barr virus (EBV), and hepatitis B virus (HBV) are disclosed.

One aspect of the invention provides a method of treating a viral infection caused by a virus selected from the group consisting of Hepatitis B (HBV) and Epstein-Barr (EBV) viruses in a mammal, the method comprising administering to the mammal in need thereof, a therapeutically effective amount of a compound of formula 1A:

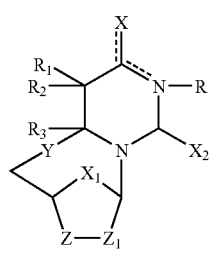

wherein:
X is $=O$, $=S$, $N=CH-N(CH_3)_2$, hydroxyl, alkoxy, thiol, acyloxy, amino, substituted amino, aminoacyl, or aminoacyloxy;

$X_1$ is O or S;
$X_2$ is $=O$, $=S$, hydroxyl, thiol, alkoxy, amino or substituted amino;
Y is O, S, NH or NAc;
R is H, alkyl, substituted alkyl, acyl, acylamino, or alkylcarboxyl with the provisio that R is not present when X is hydroxyl, thiol, alkoxy, amino or substituted amino;
$R_1$ is H, halogen, linear or branched, unsubstituted or substituted $C_1$-$C_6$ alkyl, alkoxy, substituted alkoxy, hydroxyl, amino, substituted amino, aminoacyl, thiol, thioalkoxy, carboxy, alkylcarboxyl, acylamino, acyl, aryl, alkaryl, nitro, cyano, thiocyano, azido, —$CH_2OCHO$ or formyl;
$R_2$ is H, —OH, —OAc, OMe or halogen;
$R_3$ is H; and
Z—$Z_1$ is selected from the groups consisting of $CR_4R_5$—$CR_6R_7$, (wherein $R_4$, $R_5$, $R_6$, and $R_7$ are independently selected from H, OH, halogens, cyano, $N_3$, $CH_2OH$, COOH, $C_1$-$C_4$ alkyl substituted carboxy, $NH_2$, $CH_2NH_2$, $CH_2COOH$, $C_1$-$C_3$ thioalkyl, thiol, $ONO_2$, $ONH_2$, and $CF_3$), CNS, NHCN, $CH_2N_3$, NH—($C_1$-$C_4$-alkyl), CHO, C=CH, $C_1$-$C_4$ alkoxy, or OCH$_2$aryl), CH=CH, S—$CH_2$, O—$CH_2$, or $C(R^{27})=C(R^{28})$ (wherein $R^{27}$ and $R^{28}$ are, independently of each other, selected from H, OH, halogen, or azido), and derivatives thereof wherein —OH and/or —$NH_2$ groups are protected with protecting groups, including esters, amides, phosphates, phosphoesters and phosphamides;
or a pharmaceutically acceptable salt, ester, prodrug or metabolite thereof.

Another aspect of the invention provides the use of a compound of formula 1A:

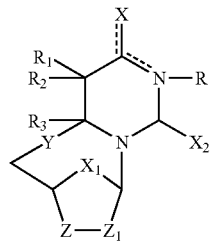

wherein:
X is $=O$, $=S$, $N=CH-N(CH_3)_2$, hydroxyl, alkoxy, thiol, acyloxy, amino, substituted amino, aminoacyl, or aminoacyloxy;
$X_1$ is O or S;
$X_2$ is $=O$, $=S$, hydroxyl, thiol, alkoxy, amino or substituted amino;
Y is O, S, NH or NAc;
R is H, alkyl, substituted alkyl, acyl, acylamino, or alkylcarboxyl with the provisio that R is not present when X is hydroxyl, thiol, alkoxy, amino or substituted amino;
$R_1$ is H, halogen, linear or branched, unsubstituted or substituted $C_1$-$C_6$ alkyl, alkoxy, substituted alkoxy, hydroxyl, amino, substituted amino, aminoacyl, thiol, thioalkoxy, carboxy, alkylcarboxy, acylamino, acyl, aryl, alkaryl, nitro, cyano, thiocyano, azido, —$CH_2OCHO$ or formyl;
$R_2$ is H, —OH, —OAc, OMe or halogen;
$R_3$ is H; and
Z—$Z_1$ is selected from the groups consisting of $CR_4R_5$—$CR_6R_7$, (wherein $R_4$, $R_5$, $R_6$, and $R_7$ are independently selected from H, OH, halogens, cyano, $N_3$, $CH_2OH$, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, and CF$_3$), CNS, NHCN, CH$_2$N$_3$, NH—(C$_1$-C$_4$-alkyl), CHO, C≡CH, C$_1$-C$_4$ alkoxy, or OCH$_2$aryl), CH═CH, S—CH$_2$, O—CH$_2$, or C(R$^{27}$)═C(R$^{28}$) (wherein R$^{27}$ and R$^{28}$ are independently of each other, selected from H, OH, halogen, or azido), and derivatives thereof wherein —OH and/or —NH$_2$ groups are protected with protecting groups, including esters, amides, phosphates, phosphoesters and phosphamides;

or a pharmaceutically acceptable salt, ester, prodrug or metabolite thereof; for preparing a medicament for treating a viral infection caused by a virus selected from the group of hepatitis B virus (HBV) and Epstein-ban virus (EBV) in a mammal.

Another aspect of the invention provides a compound of formula:

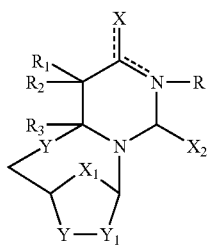

wherein:
R, R$_1$, R$_2$, R$_3$, X, X$_1$, X$_2$ and Y are described as in formula 1A, and
Y$_1$-Y$_2$ is selected from CH═CH, S—CH$_2$, O—CH$_2$, or C(R$^{27}$)═C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, phosphoesters and phosphamides.

Another aspect of the invention provides the use of a compound of formula 1A:

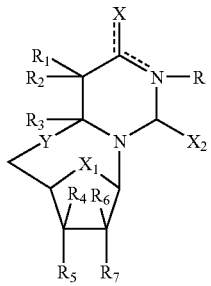

wherein:
R, R$_1$, R$_2$, R$_3$, X, X$_1$, X$_2$ and Y are as described as in formula 1A; and
R$_4$, R$_5$, R$_6$, and R$_7$ are independently selected from groups as in formula 1A;
provided that when:
R, R$_2$, and R$_3$ are H; and R$_1$ is F; and X, X$_1$, X$_2$ and Y are O; and R$_4$, R$_6$, and R$_7$ are H; then R$_5$ is different from OH, or N$_3$; and
R, R$_3$, R$_4$, R$_6$ and R$_7$ are H; N, R$_1$ and R$_2$ are Br; X, X$_1$, X$_2$ and Y are O then R$_5$ is different from OH; and R, R$_3$, R$_4$, R$_6$ and R$_7$ are H; R$_1$ and R$_2$ is I; X, X$_1$, X$_2$ and Y are O then R$_5$ is Different from OH; and
R, R$_3$, R$_4$, R$_6$ and R$_7$ are H; R$_1$ is CH$_3$, R$_2$ is either Br, I, H or OH; X, X$_1$, X$_2$ and Y are O then R$_5$ is different from OH; and
R, R$_3$, R$_4$, R$_6$ and R$_7$ are H; R$_1$ is CH$_3$, R$_2$ is either Br, I, H or OH; X, X$_1$, X$_2$ and Y are O then R$_5$ is different from N$_3$; and
R, R$_2$ R$_3$, R$_4$, R$_6$ and R$_7$ are H; R$_1$ is CH$_3$; X, X$_1$, X$_2$ and Y are O then R$_5$ is different from N$_3$ or OAc; and
R, R$_3$, R$_4$, and R$_6$ are H; R$_1$ and R$_2$ are Br; R$_7$ is OH; X, X$_1$, X$_2$ and Y are O then R$_5$ is different from OH; and
R, R$_2$ R$_3$, R$_4$, and R$_6$ are H; R$_1$ is F; R$_7$ is OH; X, X$_1$, X$_2$ and Y are O then R$_5$ is different from OH; and
Add compounds claim directed to preferred embodiments.

Another aspect of the invention provides a method of treating a viral infection caused by a virus selected from the group consisting of Hepatitis B (HBV) and Epstein-Barr (EBV) viruses in a mammal, the method comprising administering to the mammal in need thereof, a therapeutically effective amount of a compound of formula 1B:

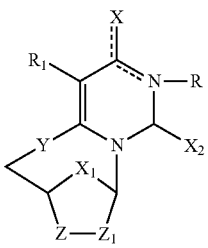

wherein:
X is ═O, ═S, N═CH—N(CH$_3$)$_2$, hydroxyl, alkoxy, thiol, acyloxy, amino, substituted amino, aminoacyl, or aminoacyloxy;
X$_1$ is O or S;
X$_2$ is ═O, ═S, hydroxyl, thiol, alkoxy, amino or substituted amino;
Y is O, S, NH or NAc;
R is H, alkyl, substituted alkyl, acyl, acylamino, or alkylcarboxyl with the provisio that R is not present when X is hydroxyl, thiol, alkoxy, amino or substituted amino;
R$_1$ is H, halogen, linear or branched, unsubstituted or substituted C$_1$-C$_6$ alkyl, alkoxy, substituted alkoxy, hydroxyl, amino, substituted amino, aminoacyl, thiol, thioalkoxy, carboxy, alkylcarboxy, acylamino, acyl, aryl, alkaryl, nitro, cyano, thiocyano, azido, —CH$_2$OCHO or formyl; and
Z—Z$_1$ is selected from the groups consisting of CR$_4$R$_5$—CR$_6$R$_7$, (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, and CF$_3$), CNS, NHCN, CH$_2$N$_3$, NH—(C$_1$-C$_4$-alkyl), CHO, C≡CH, C$_1$-C$_4$ alkoxy, or OCH$_2$aryl), CH═CH, S—CH$_2$, O—CH$_2$, or C(R$^{27}$)═C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, phosphoesters and phosphamides;
or a pharmaceutically acceptable salt, ester, prodrug or metabolite thereof.

Another aspect of the invention provides the use of a compound of formula 1B:

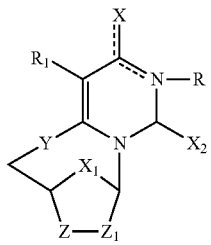

wherein:

X is =O, =S, N=CH—N(CH$_3$)$_2$, hydroxyl, alkoxy, thiol, acyloxy, amino, substituted amino, aminoacyl, or aminoacyloxy;

X$_1$ is O or S;

X$_2$ is =O, =S, hydroxyl, thiol, alkoxy, amino or substituted amino;

Y is O, S, NH or NAc;

R is H, alkyl, substituted alkyl, acyl, acylamino, or alkylcarboxyl with the provisio that R is not present when X is hydroxyl, thiol, alkoxy, amino or substituted amino;

R$_1$ is H, halogen, linear or branched, unsubstituted or substituted C$_1$-C$_6$ alkyl, alkoxy, substituted alkoxy, hydroxyl, amino, substituted amino, aminoacyl, thiol, thioalkoxy, carboxy, alkylcarboxy, acylamino, acyl, aryl, alkaryl, nitro, cyano, thiocyano, azido, —CH$_2$OCHO or formyl; and Z—Z$_1$ is selected from the groups consisting of CR$_4$R$_5$—CR$_6$R$_7$, (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, and CF$_3$), CNS, NHCN, CH$_2$N$_3$, NH—(C$_1$-C$_4$-alkyl), CHO, C=CH, C$_1$-C$_4$ alkoxy, or OCH$_2$aryl), CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, phosphoesters and phosphamides;

or a pharmaceutically acceptable salt, ester, prodrug or metabolite thereof; for preparing a medicament for treating a viral infection caused by a virus selected from the group consisting of hepatitis B virus (HBV) or Epstein-Barr virus (EBV) in a mammal.

Another aspect of the invention provides a compound of formula:

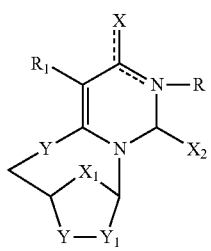

wherein:

R, R$_1$, X, X$_1$, X$_2$ and Y are described as in formula 1B, and Y$_1$-Y$_2$ is selected from CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, phosphoesters and phosphamides.

Another aspect of the invention provides a compound of the formula:

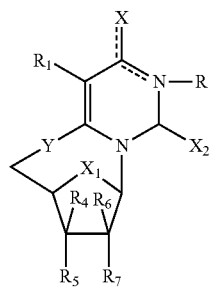

wherein:

R, R$_1$, X, X$_1$, X$_2$ and Y are as described as in formula 1B; and

R$_4$, R$_5$, R$_6$, and R$_7$ are independently selected from groups as in formula 1B;

provided that when:

R, R$_4$, R$_6$ R$_7$ are H; R$_1$ is I, Br, Cl or CH$_3$; X, X$_1$, X$_2$ and Y are O then R$_5$ is different from OH and OAc; and R is H or CH$_3$; R$_1$, R$_4$, R$_6$ and R$_7$ are H; X, X$_1$, X$_2$ and Y are O then R$_5$ is different from OH; and R$_4$, R$_6$ and R$_7$ are H; X is NH$_2$ or SH; X$_1$, X$_2$ and Y are O then R$_5$ is different from OH; and R, R$_1$, R$_4$, R$_6$ and R$_7$ are H; X is NHCOCH$_3$ or SH; X$_1$, X$_2$ and Y are O then R$_5$ is different from OAc; and R is CH$_3$ or CH$_2$Ph; R$_1$, R$_4$, R$_6$ and R$_7$ are H; X, X$_1$, X$_2$ and Y are O then R$_5$ is different from OH or OCH$_3$; and R, R$_1$, R$_4$, R$_6$ and R$_7$ are H; X and X$_1$ are O; X$_2$ is OCH$_3$, SH or NH$_2$; Y is S then R$_5$ is different from OH; and R, R$_4$, and R$_6$ are H; R$_1$ is H Br, I or Cl; R$_7$ is OH; X, X$_1$ X$_2$ and Y are O then R$_5$ is different from OH; and R is CH$_3$; R1, R$_4$, and R$_6$ are H; R$_7$ is OH; X, X$_1$ X$_2$ and Y are O then R$_5$ is different from OH or OCH$_3$; and R, R$_1$, R$_4$, and R$_6$ are H; R$_7$ is OH; X is S or NH$_2$; X$_1$ X$_2$ and Y are O then R$_5$ is different from OH; and R, R$_1$, R$_4$, and R$_6$ are H; R$_7$ is OH; X, X$_1$ and X$_2$ are O; Y is Nme; then R$_5$ is different from OH; and R, R$_1$, R$_4$, and R$_6$ are H; R$_7$ is OH; X, and X$_1$ O; X$_2$ is O or OCH$_3$, S or NH$_2$; Y is S; then R$_5$ is different from OH; and R, R$_1$, R$_4$, and R$_6$ are H; R$_7$ is OAc; X is NHCOCH$_3$; X$_1$ X$_2$ and Y are O; then R$_5$ is different from OAc; and R is CH$_2$Ph; R$_1$, R$_4$, and R$_6$ are H; R$_7$ is OH; X, X$_1$ X$_2$ and Y are O; then R$_5$ is different from OH.

Add compound claim directed to preferred embodiments.

Another aspect of the invention provides A method of treating a viral infection caused by a hepatitis B virus (HBV) in a mammal, the method comprising administering to the mammal in need thereof, a therapeutically effective amount of a compound of formula 1C:

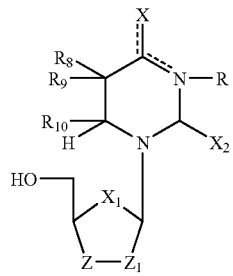

wherein:
X is =O, =S, N=CH—N(CH$_3$)$_2$, hydroxyl, alkoxy, thiol, acyloxy, amino, substituted amino, aminoacyl, or aminoacyloxy;
X$_1$ is O or S;
X$_2$ is =O, =S, hydroxyl, thiol, alkoxy, amino or substituted amino;
R is H, alkyl, substituted alkyl, acyl, acylamino, or alkylcarboxy with the provisio that R is not present when X is hydroxyl, thio, alkoxy, amino or substituted amino;
R$_8$ is H, halogen, or hydroxyl;
R$_9$ is H, halogen, or C$_1$-C$_6$ alkyl, C$_1$-C$_6$ substituted alkyl;
R$_{10}$ is H, halogen, hydroxy, alkoxy (preferably C$_1$-C$_{18}$ alkoxy), acyloxy, or azido; and
Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, and phosphoesters.

Another aspect of the invention provides the use of a compound of formula 1C:

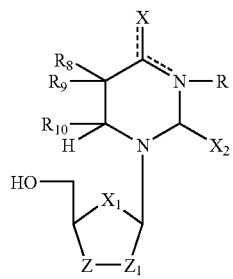

wherein:
X is =O, =S, N=CH—N(CH$_3$)$_2$, hydroxyl, alkoxy, thiol, acyloxy, amino, substituted amino, aminoacyl, or aminoacyloxy;
X$_1$ is O or S;
X$_2$ is =O, =S, hydroxyl, thiol, alkoxy, amino or substituted amino;
R is H, alkyl, substituted alkyl, acyl, acylamino, or alkylcarboxy with the provisio that R is not present when X is hydroxyl, thiol, alkoxy, amino or substituted amino;
R$_8$ is H, halogen, or hydroxyl;
R$_9$ is H, halogen, or C$_1$-C$_6$ alkyl, C$_1$-C$_6$ substituted alkyl;
R$_{10}$ is H, halogen, hydroxy, alkoxy (preferably C$_1$-C$_{18}$ alkoxy), acyloxy, or azido; and
Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, and phosphoesters;
or a pharmaceutically acceptable salt, ester, prodrug or metabolite thereof; for preparing a medicament for treating a viral infection caused by a hepatitis B virus in a mammal.

Another aspect of the invention provides a method of treating a viral infection caused by a herpes simplex virus in a mammal, the method comprising administering to the mammal in need thereof, a therapeutically effective amount of a compound of formula 1C:

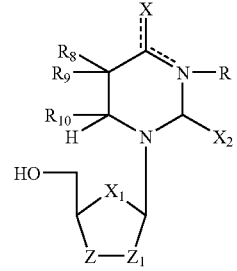

wherein:
X is =O, =S, N=CH—N(CH$_3$)$_2$, hydroxyl, alkoxy, thiol, acyloxy, amino, substituted amino, aminoacyl, or aminoacyloxy;
X$_1$ is O or S;
X$_2$ is =O, =S, hydroxyl, thiol, alkoxy, amino or substituted amino;
R is H, alkyl, substituted alkyl, acyl, acylamino, or alkylcarboxy, with the provisio that R is not present when X is hydroxyl, thiol, alkoxy, amino or substituted amino;
R$_8$ is H or halogen;
R$_9$ is H or halogen;
R$_{10}$ is hydroxy, alkoxy (preferably C$_1$-C$_{18}$ alkoxy), acyloxy, or azido; and
Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), and derivatives thereof wherein —OH and/or —NH$_2$ groups are protected with protecting groups, including esters, amides, phosphates, and phosphoesters.

Another aspect of the invention provides the use of a compound of formula 1C:

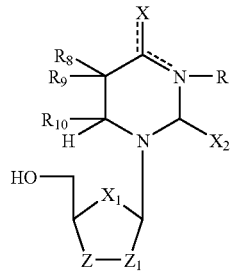

wherein:
X is =O, =S, N=CH—N(CH$_3$)$_2$, hydroxyl, alkoxy, thiol, acyloxy, amino, substituted amino, aminoacyl, or aminoacyloxy;
X$_1$ is O or S;
X$_2$ is =O, =S, hydroxyl, thiol, alkoxy, amino or substituted amino;
R is H, alkyl, substituted alkyl, acyl, acylamino, or alkylcarboxy, with the provisio that R is not present when X is hydroxyl, thiol, alkoxy, amino or substituted amino;
R$_8$ is H or halogen;
R$_9$ is H or halogen;
R$_{10}$ is hydroxy, alkoxy (preferably C$_1$-C$_{18}$ alkoxy), acyloxy, or azido; and
Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), and derivatives thereof wherein —OH and/or —NH$_2$ groups are protected with protecting groups, including esters, amides, phosphates, and phosphoesters;
or a pharmaceutically acceptable salt, ester, prodrug or metabolite thereof; for preparing a medicament for treating a viral infection caused by a herpes simplex virus (HSV) in a mammal.

Another aspect of the invention provides a compound of formula:

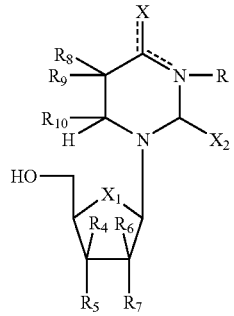

wherein:
X is =O, =S, N=CH—N(CH$_3$)$_2$, hydroxyl, alkoxy, thiol, acyloxy, amino, substituted amino, aminoacyl, or aminoacyloxy;
X$_1$ is O or S;
X$_2$ is =O, =S, hydroxyl, thiol, alkoxy, amino or substituted amino;
R is H, alkyl, substituted alkyl, acyl, acylamino, or alkylcarboxy, with the provisio that R is not present when X is hydroxyl, thiol, alkoxy, amino or substituted amino;
R$_8$ is H, halogen or hydroxy;
R$_9$ is H or halogen;
R$_{10}$ is H, halogen, hydroxy, alkoxy (preferably C$_1$-C$_{18}$ alkoxy), acyloxy, or azido; and
Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with protecting groups, including esters, amides, phosphates, and phosphoesters;
provided that when:
R, R$_4$, R$_6$, R$_7$ and R$_8$ are H; R$_9$ is Br, I, F or H; R$_{10}$ is OH; X is O NH$_2$; X$_1$ and X$_2$ are O; then R$_5$ is different from OH; and
R, R$_4$, R$_6$, R$_7$ and R$_8$ are H; R$_9$ is I; R$_{10}$ is OEt; X, X$_1$ and X$_2$ are O then R$_5$ is different from OH; and
R, R$_4$, R$_6$, R$_7$, R$_8$, and R$_{10}$ are H; R$_9$ is C(OCH$_3$—CH$_2$CF$_3$), Br, I, and Cl; X, X$_1$ and X$_2$ are O then R$_5$ is different from OH, OAc or O-acyloxy (C$_1$-C$_{12}$); and
R, R$_4$, R$_6$, R$_7$ and R$_8$, are H; R$_9$ is Br or I; R$_{10}$ N$_3$ or OMe; X, X$_1$ and X$_2$ are O then R$_5$ is different from OH, OAc; and
R, R$_4$, R$_6$, R$_7$ and R$_8$, are H; R$_9$ is OH; R$_{10}$ OH or OMe; X is O or NH; X$_1$ and X$_2$ are O then R$_5$ is different from OH, OAc; and
R, R$_4$, R$_6$, R$_7$ R$_8$ and R$_{10}$ are H; R$_9$ is F; X, X$_1$ and X$_2$ are O then R$_5$ is different from OCH$_2$Ph; and
R, R$_4$, R$_6$ and R$_7$ are H; R$_8$ is Br; R$_9$ is F; R$_{10}$ is OH, OMe, OEt, OBu or OAc; X, X$_1$ and X$_2$ are O then R$_5$ is different from OH or OAc; and
R, R$_4$, R$_6$ and R$_7$ are H; R$_8$ is Br; R$_9$ is F; R$_{10}$ is OMe; X is NH$_2$; X$_1$ and X$_2$ are O then R$_5$ is different from OH; and
R, R$_4$, R$_6$ and R$_7$ are H; R$_8$ is Cl; R$_9$ is F; R$_{10}$ is OMe or OBu; X, X$_1$ and X$_2$ are O then R$_5$ is different from OH; and
R, R$_4$, R$_6$ and R$_7$ are H; R$_8$ is F; R$_9$ is F; R$_{10}$ is OH or OAc; X, X$_1$ and X$_2$ are O then R$_5$ is different from OH; and
R, R$_4$, R$_6$ R$_7$ and R$_8$ are H; R$_9$ is F; R$_{10}$ is F, or OAc; X, X$_1$ and X$_2$ are O then R$_5$ is different from COOEt; and
R, R$_4$, R$_6$ and R$_7$ are H; R$_8$, is Br; R$_9$ is F; R$_{10}$ is OMe; X is NH$_2$; X$_1$ and X$_2$ are O then R$_5$ is different from OH; and
R, R$_4$, R$_6$, R$_7$ and R$_8$ are H; R$_9$ is F; R$_{10}$ is OMe; X is NH$_2$; X$_1$ and X$_2$ are O then R$_5$ is different from OH; and
R, R$_4$, R$_6$, and R$_8$ are H; R$_7$ is OH; R$_9$ is halogen, SH or OH; R$_{10}$ is OH, H, C$_1$-C$_6$ alkoxy or C$_1$-C$_6$ O-alkanoyl; X is O or NH$_2$; X$_1$ and X$_2$ are O then R$_5$ is different from OH and OAc; and
R, R$_4$, R$_6$, and R$_8$ are H; R$_7$ is OAc; R$_9$ is OH; R$_{10}$ is OH; X, X$_1$ and X$_2$ are O then R$_5$ is different from OAc; and
R, R$_4$ and R$_6$ are H; R$_7$ is OH; R$_8$ and R$_9$ are Br; R$_{10}$ is OH; X is O or NH$_2$; X$_1$ and X$_2$ are O then R$_5$ is different from OH; and
R, R$_4$ and R$_6$ are H; R$_7$ is OH or OAc; R$_8$ and R$_9$ are F; R$_{10}$ is OH or OAc; X is O or NH$_2$; X$_1$ and X$_2$ are O then R$_5$ is different from OH; and R, $R_4$ $R_6$, $R_8$ and $R_9$ are H; $R_7$ is OH or OAc; $R_{10}$ is H or OMe; X is O, NHAc, S or $NH_2$; $X_1$ is O; $X_2$ is O, NH, $NCH_3$ or S then $R_5$ is different from OH; and R, $R_4$ $R_6$, $R_9$ and $R_{10}$ are H; $R_7$ is OH; $R_8$ is $NO_2$; X, $X_1$ and $X_2$ are O then $R_5$ is different from OH; and R, $R_4$ $R_7$, and $R_8$ are H; $R_6$ is OH; $R_9$ is F; $R_{10}$ or OH, OMe, OEt or OAc; X, $X_1$ and $X_2$ are O then $R_5$ is different from OH; and R, $R_4$ and $R_7$, are H; $R_6$ is OH; $R_8$ and $R_9$ are F; $R_{10}$ is OH or OAc; X is O or $NH_2$; $X_1$ and $X_2$ are O then $R_5$ is different from OH; and R, $R_4$ and $R_7$, are H; $R_6$ is OOAc; $R_8$ is Br; $R_9$ is F; $R_{10}$ is OAc; X, $X_1$ and $X_2$ are O then $R_5$ is different from H; and R, $R_6$ and $R_7$, are H; $R_4$ is OH; $R_8$ is F; $R_9$ is Br or Cl; $R_{10}$ is $O(CH_3)_3$; X, $X_1$ and $X_2$ are O then $R_5$ is different from H; and R, $R_4$ $R_6$ and $R_8$, are H; $R_7$ is Br or Cl; $R_9$ is Br, I or F; $R_{10}$ is OMe or OEt; X, $X_1$ and $X_2$ are O then $R_5$ is different from OH; and R, $R_4$ $R_6$ and $R_8$, are H; $R_7$ is Br or I; $R_9$ is F; $R_{10}$ is F or OAc; X, $X_1$ and $X_2$ are O then $R_5$ is different from OAc or COOEt; and R, $R_4$ $R_6$ $R_8$ and $R_{10}$, are H; $R_7$ is F; $R_9$ is Br, Cl or F; X, $X_1$ and $X_2$ are O then $R_5$ is different from OH; and R, $R_4$ $R_6$ $R_8$, $R_9$ and $R_{10}$, are H; $R_7$ is SH, OAc, OH or $N_3$; X, $X_1$ and $X_2$ are O then $R_5$ is different from OH; and R, $R_4$ $R_6$ $R_8$ and $R_9$, are H; $R_7$ is F; $R_{10}$ is OH; X, $X_1$ and $X_2$ are O then $R_5$ is different from OH; and Another aspect of the invention provides a method of treating a viral infection caused by a virus selected from the group consisting of Hepatitis B (HBV) and Epstein-Barr (EBV) viruses in a mammal, the method comprising administering to the mammal in need thereof, a therapeutically effective amount of a compound of formula:

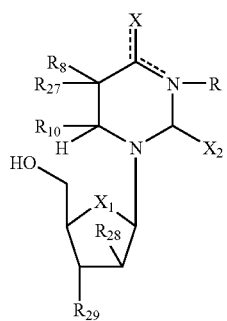

wherein:

X is =O, =S, N=CH—$N(CH_3)_2$, hydroxyl, alkoxy, thiol, acyloxy, amino, substituted amino, aminoacyl, or aminoacyloxy;

$X_1$ is O or S;

$X_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

$R_8$ is H, halogen, or hydroxyl;

$R_{10}$ is hydroxy, alkoxy (preferably $C_1$-$C_{18}$ alkoxy), acyloxy, or azido;

$R_{27}$ is $C_1$-$C_6$ alkyl, or $C_1$-$C_6$ substituted alkyl;

$R_{28}$ is halogen, hydroxyl, azido or cyano; and $R_{29}$ is hydroxy, $C_1$-$C_3$ alkoxy, amino, or substituted amino.

Another aspect of the invention provides the use of a compound of formula:

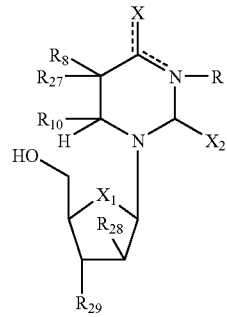

wherein:

X is =O, =S, N=CH—$N(CH_3)_2$, hydroxyl, alkoxy, thiol, acyloxy, amino, substituted amino, aminoacyl, or aminoacyloxy;

$X_1$ is O or S;

$X_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

$R_8$ is H, halogen, or hydroxyl;

$R_{10}$ is H, halogen, hydroxy, alkoxy (preferably $C_1$-$C_{18}$ alkoxy), acyloxy, or azido;

$R_{27}$ is $C_1$-$C_6$ alkyl, or $C_1$-$C_6$ substituted alkyl;

$R_{28}$ is halogen, hydroxyl, azido or cyano; and $R_{29}$ is hydroxy, $C_1$-$C_3$ alkoxy, amino, or substituted amino;

or a pharmaceutically acceptable salt, ester, prodrug or metabolite thereof, for preparing a medicament for treating a viral infection selected from the group consisting of hepatitis B (HBV) and Epstein-Barr (EBV) viruses in a mammal.

Another aspect of the invention provides a compound of the formula:

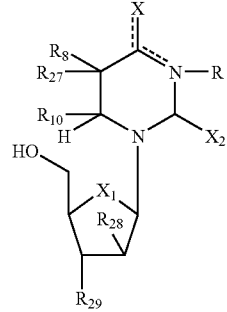

wherein:

X is =O, =S, N=CH—$N(CH_3)_2$, hydroxyl, alkoxy, thiol, acyloxy, amino, substituted amino, aminoacyl, or aminoacyloxy;

$X_1$ is O or S;

$X_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

$R_8$ is H, halogen, or hydroxyl;

$R_{10}$ is H, halogen, hydroxy, alkoxy (preferably $C_1$-$C_{18}$ alkoxy), acyloxy, or azido;

$R_{27}$ is $C_1$-$C_6$ alkyl, or $C_1$-$C_6$ substituted alkyl;

$R_{28}$ is halogen, hydroxyl, azido or cyano; and $R_{29}$ is hydroxy, $C_1$-$C_3$ alkoxy, amino, or substituted amino.

Another aspect of the invention provides a method of treating a viral infection caused by a virus selected from the group consisting of Hepatitis B (HBV) and Epstein-Barr (EBV) viruses in a mammal, the method comprising administering to the mammal in need thereof, a therapeutically effective amount of a compound of formula 1D:

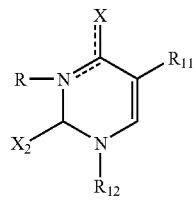

wherein:

X is =O, =S, N=CH—N(CH$_3$)$_2$, hydroxyl, alkoxy, thiol, acyloxy, amino, substituted amino, aminoacyl, or aminoacyloxy;

$X_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

$R_{11}$ is halogen, hydroxyl, carboxy, formyl, nitro, cyano, azido, alkyl (preferably a linear or branched, unsubstituted or substituted $C_2$-$C_6$ alkyl), alkaryl, —CHR$^{21}$—CH$_2$R$^{22}$, —(CH$_2$)$_n$CHR$^{21}$—CH$_2$R$^{22}$ (wherein R$^{21}$ and R$^{22}$ are, independently of each other, selected from H, OH, $C_1$-$C_6$ alkyl, alkoxy, substituted alkoxy, halogen, —CF$_3$, azido, nitrato, cyano, —NHCH$_3$, amino, nitro, cyanamido, carboxy, CON$_3$, and aryl, and wherein n=0-3), thiol, thioalkyl, substituted thioalkyl, thioaryl, alkoxyalkyl, alkoxy, substituted alkoxy, acyl, acylamino, aminoacyl, aryl, aryloxy, alkylcarboxy, amino, substituted amino, alkenyl, substituted alkenyl including —CR$^{23}$=CR$^{24}$—R$^{25}$ and —(CH$_2$)$_n$CR$^{23}$=CR$^{24}$—R$^{25}$ (wherein R$^{23}$, R$^{24}$ and R$^{25}$ are, independently of each other, selected from H, —C$_{1-6}$ substituted or unsubstituted alkyl, —CF$_3$, —CH$_2$OH, alkoxy, substituted alkoxy, nitro, cyano, cyanamido, azido, amino, amido, —CON$_3$, —CON-alkyl, —COOH, alkylcarboxy, aryl and halogen, and wherein n=0-3), alkynyl, substituted alkynyl, including C=CR$^{26}$ and —(CH$_2$)$_n$C=CR$^{26}$, $R_{12}$ is:

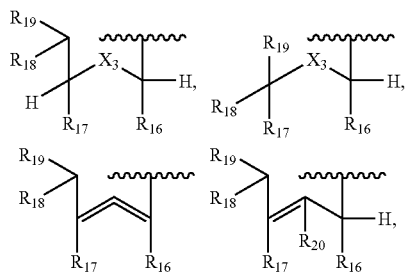

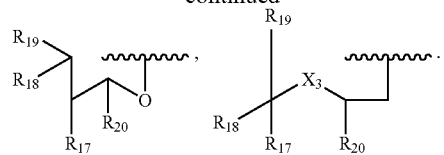

$R_{16}$ is H, $C_1$-$C_3$ alkyl, (CH$_2$)$_n$—N$_3$, (CH$_2$)$_n$-halogen, (CH$_2$)$_n$-amino, $C_1$-$C_3$ (CH$_2$)$_n$-alkoxy, or (CH$_2$)$_n$OH (wherein n=0 or 1-3)

$R_{17}$ is H, (CH$_2$)$_n$—OH, COOH, $C_1$-$C_3$ alkyl, $C_1$-$C_3$ substituted alkyl, CHOH—CH$_2$OH, $C_1$-$C_3$ CHOH-alkyl, CHOH—CH$_2$-halogen, CH-halogen-CH$_2$OH, benzyloxyalkyl, (CH$_2$)$_n$—CHO, (CH$_2$)$_n$-aryl, (CH$_2$)$_n$-aryloxy, (CH$_2$)$_n$—N$_3$, (CH$_2$)$_n$-halogen, (CH$_2$)$_n$-amino, (CH$_2$)$_n$-substituted amino, (CH$_2$)$_n$-acyl, (CH$_2$)$_n$-acyloxy, (CH$_2$)$_n$-acylamino, (CH$_2$)$_n$-aminoacyl, (CH$_2$)$_n$-thiol, or (CH$_2$)$_n$-aminoacyloxy (n=0 or 1-3);

$R_{18}$ is H, —OH, —PO(OH)$_2$ or $C_1$-$C_6$ alkyl;

$R_{19}$ is H, —(CH$_2$)$_n$—OH, —(CH$_2$)$_n$—N$_3$, alkyl, substituted alkyl, straight, branched or cyclic alkyl, hydroxyalkyl, OCH$_2$PO$_3$, —(CH$_2$)$_n$P(O)(OH)$_2$, —(CH$_2$)$_n$-halogen, —(CH$_2$)$_n$—OCHO, —(CH$_2$)$_n$-alkoxy, —(CH$_2$)-substituted alkoxy, —(CH$_2$)$_n$ aryloxy, —(CH$_2$)$_n$-aryl, —(CH$_2$)$_n$-thiol, —(CH$_2$)$_n$-acyl, —(CH$_2$)$_n$-acyloxy-(CH$_2$)$_n$-acylamino, —(CH$_2$)$_n$-aminoacyl, —(CH$_2$)$_n$-aminoacyloxy, —(CH$_2$)$_n$amino, or —(CH$_2$)$_n$-substituted amino, (n=0 or 1-12); and $R_{20}$ is H, alkyl, COOH, CONH$_2$, CHO, (CH$_2$)$_n$OH, NHCONH$_2$, OH or halogen, wherein n=0 or 1-3;

$R_{26}$ is H, $C_1$-$C_3$ substituted and unsubstituted alkyl, CF$_3$, $C_1$-$C_3$ alkoxy, CH$_2$OH, nitro, cyano, NHCN, amido, amino, alkylamino, aryl, or halo; and $X_3$ is O, S, C=CH$_2$, or CHR$_{20}$.

Another aspect of the invention provides the use of a compound of formula 1D:

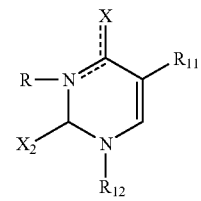

wherein:

X is =O, =S, N=CH—N(CH$_3$)$_2$, hydroxyl, alkoxy, thiol, acyloxy, amino, substituted amino, aminoacyl, or aminoacyloxy;

$X_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

$R_{11}$ is halogen, hydroxyl, carboxy, formyl, nitro, cyano, azido, alkyl (preferably a linear or branched, unsubstituted or substituted $C_2$-$C_6$ alkyl), alkaryl, —CHR$^{21}$—CH$_2$R$^{22}$, —(CH$_2$)$_n$CHR$^{21}$—CH$_2$R$^{22}$ (wherein R$^{21}$ and R$^{22}$ are, independently of each other, selected from H, OH, $C_1$-$C_6$ alkyl, alkoxy, substituted alkoxy, halogen, —CF$_3$, azido, nitrato, cyano, —NHCH$_3$, amino, nitro, cyanamido, carboxy, CON$_3$, and aryl, and wherein n=0-3), thiol, thioalkyl, substituted thioalkyl, thioaryl, alkoxyalkyl, alkoxy, substituted alkoxy, acyl, acylamino, aminoacyl, aryl, aryloxy, alkylcarboxy, amino, substituted amino, alkenyl, substituted alkenyl including —CR$^{23}$=CR$^{24}$—R$^{25}$ and —(CH$_2$)$_n$CR$^{23}$=CR$^{24}$—R$^{25}$ (wherein R$^{23}$, R$^{24}$ and R$^{25}$ are, independently of each other, selected from H, —C$_{1-6}$ substituted or unsubstituted alkyl, —CF$_3$, —CH$_2$OH, alkoxy, substituted alkoxy, nitro, cyano, cyanamide, azido, amino, amido, —CON$_3$, —CON-alkyl, —COOH, alkylcarboxy, aryl and halogen, and wherein n=0-3), alkynyl, substituted alkynyl, including C≡CR$^{26}$ and —(CH$_2$)$_n$C≡CR$^{26}$;

R$_{12}$ is:

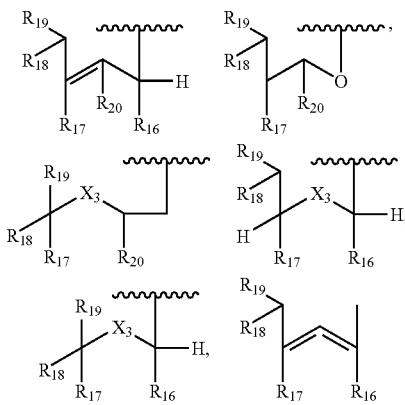

R$_{16}$=H, C$_1$-C$_3$ alkyl, (CH$_2$)$_n$—N$_3$, (CH$_2$)$_n$-halogen, (CH$_2$)$_n$-amino, C$_1$-C$_3$ (CH$_2$)$_n$-alkoxy, or (CH$_2$)$_n$OH (wherein n=0 or 1-3)

R$_{17}$=H, (CH$_2$)$_n$—OH, COOH, C$_1$-C$_3$ alkyl, C$_1$-C$_3$ substituted alkyl, CHOH—CH$_2$OH, C$_1$-C$_3$ CHOH-alkyl, CHOH—CH$_2$-halogen, CH-halogen-CH$_2$OH, benzyloxyalkyl, (CH$_2$)$_n$—CHO, (CH$_2$)$_n$-aryl, (CH$_2$)$_n$-aryloxy, (CH$_2$)$_n$—N$_3$, (CH$_2$)$_n$-halogen, (CH$_2$)$_n$-amino, (CH$_2$)$_n$-substituted amino, (CH$_2$)$_n$-acyl, (CH$_2$)$_n$-acyloxy, (CH$_2$)$_n$-acylamino, (CH$_2$)$_n$-aminoacyl, (CH$_2$)$_n$-thiol, or (CH$_2$)$_n$-aminoacyloxy (n=0 or 1-3);

R$_{18}$=H, —OH, —PO(OH)$_2$ or C$_1$-C$_6$ alkyl;

R$_{19}$=H, —(CH$_2$)$_n$—OH, —(CH$_2$)$_n$—N$_3$, alkyl, substituted alkyl, straight, branched or cyclic alkyl, hydroxyalkyl, OCH$_2$PO$_3$, —(CH$_2$)$_n$P(O)(OH)$_2$, —(CH$_2$)$_n$-halogen, —(CH$_2$)$_n$—OCHO, —(CH$_2$)$_n$-alkoxy, —(CH$_2$)$_n$-substituted alkoxy, —(CH$_2$)$_n$ aryloxy, —(CH$_2$)$_n$-aryl, —(CH$_2$)$_n$-thiol, —(CH$_2$)$_n$-acyl, —(CH$_2$)$_n$-acyloxy-(CH$_2$)$_n$-acylamino, —(CH$_2$)$_n$-aminoacyl, —(CH$_2$)$_n$-aminoacyloxy, —(CH$_2$)$_n$amino, or —(CH$_2$)$_n$-substituted amino, (n=0 or 1-12); and R$_{20}$=H, alkyl, COOH, CONH$_2$, CHO, (CH$_2$)$_n$OH, NHCONH$_2$, OH or halogen, wherein n=0 or 1-3;

R$_{26}$ is H, C$_1$-C$_3$ substituted and unsubstituted alkyl, CF$_3$, C$_1$-C$_3$ alkoxy, CH$_2$OH, nitro, cyano, NHCN, amido, amino, alkylamino, aryl, or halo; and X$_3$ is O, S, C=CH$_2$, or CHR$_{20}$;

or a pharmaceutically acceptable salt, ester, prodrug or metabolite thereof; for preparing a medicament for treating a viral infection caused by a virus selected from the group of hepatitis B virus (HBV) and Epstein-barr virus (EBV) in a mammal.

Another aspect of the invention provides a compound of formula:

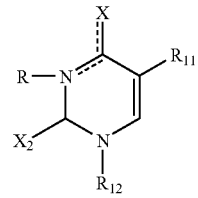

wherein:

X is =O, =S, N=CH—N(CH$_3$)$_2$, hydroxyl, alkoxy, thiol, acyloxy, amino, substituted amino, aminoacyl, or aminoacyloxy;

X$_2$ is =O, =S, hydroxyl, thiol, alkoxy, amino or substituted amino;

R is H, alkyl, substituted alkyl, acyl, acylamino, or alkylcarboxy, with the provisio that R is not present when X is hydroxyl, thiol, alkoxy, amino or substituted amino;

R$_{11}$ is hydroxyl, carboxy, formyl, nitro, cyano, azido, alkyl (preferably a linear or branched, unsubstituted or substituted C$_2$-C$_6$ alkyl), alkaryl, —CHR$^{21}$—CH$_2$R$^{22}$, —(CH$_2$)$_n$CHR$^{21}$—CH$_2$R$^{22}$ (wherein R$^{21}$ and R$^{22}$ are, independently of each other, selected from H, OH, C$_1$-C$_6$ alkyl, alkoxy, substituted alkoxy, halogen, —CF$_3$, azido, nitrato, cyano, —NHCH$_3$, amino, nitro, cyanamido, carboxy, CON$_3$, and aryl, and wherein n=0-3), thiol, thioalkyl, substituted thioalkyl, thioaryl, alkoxyalkyl, alkoxy, substituted alkoxy, acyl, acylamino, aminoacyl, aryl, aryloxy, alkylcarboxy, amino, substituted amino, alkenyl, substituted alkenyl including —CR$^{23}$=CR$^{24}$—R$^{25}$ and —(CH$_2$)$_n$CR$^{23}$=C R$^{24}$—R$^{25}$ (wherein R$^{23}$, R$^{24}$ and R$^{25}$ are, independently of each other, selected from H, —C$_{1-6}$ substituted or unsubstituted alkyl, —CF$_3$, —CH$_2$OH, alkoxy, substituted alkoxy, nitro, cyano, cyanamido, azido, amino, amido, —CON$_3$, —CON-alkyl, —COOH, alkylcarboxy, aryl and halogen, and wherein n=0-3), alkynyl, substituted alkynyl, including C≡CR$^{26}$ and —(CH$_2$)$_n$C≡CR$^{26}$;

R$_{12}$ is

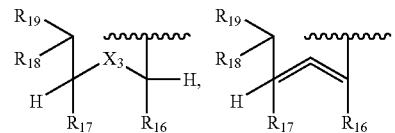

R$_{16}$ is H, C$_1$-C$_3$ alkyl, (CH$_2$)$_n$—N$_3$, (CH$_2$)$_n$-halogen, (CH$_2$)$_n$-amino, C$_1$-C$_3$ (CH$_2$)$_n$-alkoxy, or (CH$_2$)$_n$OH (wherein n=0 or 1-3)

R$_{17}$ is H, (CH$_2$)$_n$—OH, COOH, C$_1$-C$_3$ alkyl, C$_1$-C$_3$ substituted alkyl, CHOH—CH$_2$OH, C$_1$-C$_3$ CHOH-alkyl, CHOH—CH$_2$-halogen, CH-halogen-CH$_2$OH, benzyloxyalkyl, (CH$_2$)$_n$—CHO, (CH$_2$)$_n$-aryl, (CH$_2$)$_n$-aryloxy, (CH$_2$)$_n$—N$_3$, (CH$_2$)$_n$-halogen, (CH$_2$)$_n$-amino, (CH$_2$)$_n$-substituted amino, (CH$_2$)$_n$-acyl, (CH$_2$)$_n$-acyloxy, (CH$_2$)$_n$-acylamino, (CH$_2$)$_n$-aminoacyl, (CH$_2$)$_n$-thiol, or (CH$_2$)$_n$-aminoacyloxy (n=0 or 1-3);

R$_{18}$ is H, —OH, —PO(OH)$_2$ or C$_1$-C$_6$ alkyl;

R$_{19}$ is H, —(CH$_2$)$_n$—OH, —(CH$_2$)$_n$—N$_3$, alkyl, substituted alkyl, straight, branched or cyclic alkyl, hydroxyalkyl, OCH$_2$PO$_3$, —(CH$_2$)$_n$P(O)(OH)$_2$, —(CH$_2$)$_n$-halogen, —(CH$_2$)$_n$—OCHO, —(CH$_2$)$_n$-alkoxy, —(CH$_2$)$_n$-substituted alkoxy, —(CH$_2$)$_n$ aryloxy, —(CH$_2$)$_n$-aryl, —(CH$_2$)$_n$-thiol, —(CH$_2$)$_n$-acyl, —(CH$_2$)$_n$-acyloxy- $(CH_2)_n$-acylamino, $-(CH_2)_n$-aminoacyl, $-(CH_2)_n$-aminoacyloxy, $-(CH_2)_n$amino, or $-(CH_2)_n$-substituted amino, (n=0 or 1-12);

$R_{26}$ is H, $C_1$-$C_3$ substituted and unsubstituted alkyl, $CF_3$, $C_1$-$C_3$ alkoxy, $CH_2OH$, nitro, cyano, NHCN, amido, amino, alkylamino, aryl, or halo; and $X_3$ is O, S, C=$CH_2$, or $CHR_{20}$.

provided that when:

R is H, X is NH, $X_2$ is O, $R_{11}$ is $NH_2$, halogen, $NO_2$, $NH_2CH_3$, isopropyl, $C_2H_5$, $CH_2-CH=CH_2$, CH=CH—COOMe, CH=CHBr, and $X_3$ is different from O, R is H, X is O, $X_2$ is O, $R_{11}$ is alkyl, substituted alkyl, $CF_3$, $NH_2$, then $X_3$ is different from O, Another aspect of the invention provides a method of treating a viral infection caused by a vacirella zoster virus (VZV) in a mammal, the method comprising administering to the mammal in need thereof, a therapeutically effective amount of a compound of formula 1E:

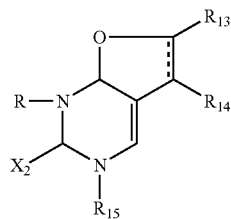

wherein:

$X_2$ is =O, =S, hydroxyl, thiol, alkoxy, amino or substituted amino;

R is H, alkyl, substituted alkyl, acyl, acylamino, or alkylcarboxy, with the proviso that R is not present when X is hydroxyl, thiol, alkoxy, amino or substituted amino;

$R_{13}$ and $R_{14}$ can be independently selected from H, OH, halogen, a branched, straight, unsubstituted or substituted alkyl containing 1-16 carbon atoms, aminoacyl, acyloxy, alkoxy, alkylalkoxy, substituted alkoxy, or azido, wherein the dashed line between $R_{13}$ and $R_{14}$ represents a facultative double bond;

$R_{15}$ is

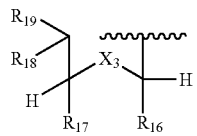

and derivatives thereof wherein —OH and/or —$NH_2$ groups are protected with protecting groups, including esters, amides, phosphates, phosphoesters and phosphamides;

$R_{16}$ is H, $C_1$-$C_3$ alkyl, $(CH_2)_n$—$N_3$, $(CH_2)_n$-halogen, $(CH_2)_n$-amino, $C_1$-$C_3$ $(CH_2)_n$-alkoxy, or $(CH_2)_n$OH (wherein n=0 or 1-3)

$R_{17}$ is H, $(CH_2)_n$—OH, COOH, $C_1$-$C_3$ alkyl, $C_1$-$C_3$ substituted alkyl, CHOH—$CH_2OH$, $C_1$-$C_3$ CHOH-alkyl, CHOH—$CH_2$-halogen, CH-halogen-$CH_2OH$, benzyloxyalkyl, $(CH_2)_n$—CHO, $(CH_2)_n$-aryl, $(CH_2)_n$-aryloxy, $(CH_2)_n$—$N_3$, $(CH_2)_n$-halogen, $(CH_2)_n$-amino, $(CH_2)_n$-substituted amino, $(CH_2)_n$-acyl, $(CH_2)_n$-acyloxy, $(CH_2)_n$-acylamino, $(CH_2)_n$-aminoacyl, $(CH_2)_n$-thiol, or $(CH_2)_n$-aminoacyloxy (n=0 or 1-3);

$R_{18}$ is H, —OH, —$PO(OH)_2$ or $C_1$-$C_6$ alkyl; and $R_{19}$ is H, $-(CH_2)_n$—OH, $-(CH_2)_n$—$N_3$, alkyl, substituted alkyl, straight, branched or cyclic alkyl, hydroxyalkyl, $OCH_2PO_3$, $-(CH_2)_nP(O)(OH)_2$, $-(CH_2)_n$-halogen, $-(CH_2)_n$—OCHO, $-(CH_2)_n$-alkoxy, $-(CH_2)_n$-substituted alkoxy, $-(CH_2)_n$ aryloxy, $-(CH_2)_n$-aryl, $-(CH_2)_n$-thiol, $-(CH_2)_n$-acyl, $-(CH_2)_n$-acyloxy-$(CH_2)_n$-acylamino, $-(CH_2)_n$-aminoacyl, $-(CH_2)_n$-aminoacyloxy, $-(CH_2)_n$amino, or $-(CH_2)_n$-substituted amino, (n=0 or 1-12); and $X_3$ is O, S, C=$CH_2$, or $CHR_{20}$.

Another aspect of the invention provides the use of a compound of formula 1E:

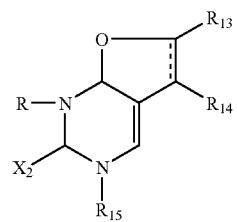

wherein:

$X_2$ is =O, =S, hydroxyl, thiol, alkoxy, amino or substituted amino;

R is H, alkyl, substituted alkyl, acyl, acylamino, or alkylcarboxy, with the proviso that R is not present when X is hydroxyl, thiol, alkoxy, amino or substituted amino;

$R_{13}$ and $R_{14}$ can be independently selected from H, OH, halogen, a branched, straight, unsubstituted or substituted alkyl containing 1-16 carbon atoms, aminoacyl, acyloxy, alkoxy, alkylalkoxy, substituted alkoxy, or azido, wherein the dashed line between $R_{13}$ and $R_{14}$ represents a facultative double bond;

$R_{15}$ is

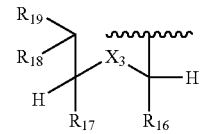

and derivatives thereof wherein —OH and/or —$NH_2$ groups are protected with protecting groups, including esters, amides, phosphates, phosphoesters and phosphamides;

$R_{16}$ is H, $C_1$-$C_3$ alkyl, $(CH_2)_n$—$N_3$, $(CH_2)_n$-halogen, $(CH_2)_n$-amino, $C_1$-$C_3$ $(CH_2)_n$-alkoxy, or $(CH_2)_n$OH (wherein n=0 or 1-3)

$R_{17}$ is H, $(CH_2)_n$—OH, COOH, $C_1$-$C_3$ alkyl, $C_1$-$C_3$ substituted alkyl, CHOH—$CH_2OH$, $C_1$-$C_3$ CHOH-alkyl, CHOH—$CH_2$-halogen, CH-halogen-$CH_2OH$, benzyloxyalkyl, $(CH_2)_n$—CHO, $(CH_2)_n$-aryl, $(CH_2)_n$-aryloxy, $(CH_2)_n$—$N_3$, $(CH_2)_n$-halogen, $(CH_2)_n$-amino, $(CH_2)_n$-substituted amino, $(CH_2)_n$-acyl, $(CH_2)_n$-acyloxy, $(CH_2)_n$-acylamino, $(CH_2)_n$-aminoacyl, $(CH_2)_n$-thiol, or $(CH_2)_n$-aminoacyloxy (n=0 or 1-3);

$R_{18}$ is H, —OH, —$PO(OH)_2$ or $C_1$-$C_6$ alkyl; and $R_{19}$ is H, $-(CH_2)_n$—OH, $-(CH_2)_n$—$N_3$, alkyl, substituted alkyl, straight, branched or cyclic alkyl, hydroxyalkyl, $OCH_2PO_3$, $-(CH_2)_nP(O)(OH)_2$, $-(CH_2)_n$-halogen, $-(CH_2)_n$—OCHO, $-(CH_2)_n$-alkoxy, $-(CH_2)_n$-substituted alkoxy, $-(CH_2)_n$ aryloxy, $-(CH_2)_n$-aryl, —(CH$_2$)$_n$-thiol, —(CH$_2$)$_n$-acyl, —(CH$_2$)$_n$-acyloxy-(CH$_2$)$_n$-acylamino, —(CH$_2$)$_n$-aminoacyl, —(CH$_2$)$_n$-aminoacyloxy, —(CH$_2$)$_n$amino, or —(CH$_2$)$_n$-substituted amino, (n=0 or 1-12); and X$_3$ is O, S, C=CH$_2$, or CHR$_{20}$.

or a pharmaceutically acceptable salt, ester, prodrug or metabolite thereof for preparing a medicament for treating a viral infection caused by a vacirella zoster virus (VZV) in a mammal.

Another aspect of the invention provides a compound of formula 1E:

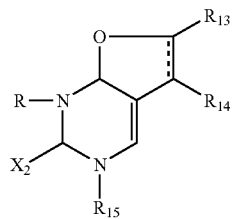

wherein:

X$_2$ is =O, or =S;

R is H, alkyl, substituted alkyl, acyl, acylamino, or alkylcarboxy, with the provisio that R is not present when X is hydroxyl, thiol, alkoxy, amino or substituted amino;

R$_{13}$ and R$_{14}$ can be independently selected from H, OH, halogen, a branched, straight, unsubstituted or substituted alkyl containing 1-16 carbon atoms, aminoacyl, acyloxy, alkoxy, alkylalkoxy, substituted alkoxy, or azido, wherein the dashed line between R$_{13}$ and R$_{14}$ represents a facultative double bond;

R$_{15}$ is

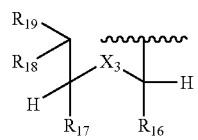

and derivatives thereof wherein —OH and/or —NH$_2$ groups are protected with protecting groups, including esters, amides, phosphates, phosphoesters and phosphamides;

R$_{16}$ is H, C$_1$-C$_3$ alkyl, (CH$_2$)$_n$—N$_3$, (CH$_2$)$_n$-halogen, (CH$_2$)$_n$-amino, C$_1$-C$_3$ (CH$_2$)$_n$-alkoxy, or (CH$_2$)$_n$OH (wherein n=0 or 1-3)

R$_{17}$ is H, (CH$_2$)$_n$—OH, COOH, C$_1$-C$_3$ alkyl, C$_1$-C$_3$ substituted alkyl, CHOH—CH$_2$OH, C$_1$-C$_3$ CHOH-alkyl, CHOH—CH$_2$-halogen, CH-halogen-CH$_2$OH, benzyloxyalkyl, (CH$_2$)$_n$—CHO, (CH$_2$)$_n$-aryl, (CH$_2$)$_n$-aryloxy, (CH$_2$)$_n$—N$_3$, (CH$_2$)$_n$-halogen, (CH$_2$)$_n$-amino, (CH$_2$)$_n$-substituted amino, (CH$_2$)$_n$-acyl, (CH$_2$)$_n$-acyloxy, (CH$_2$)$_n$-acylamino, (CH$_2$)$_n$-aminoacyl, (CH$_2$)$_n$-thiol, or (CH$_2$)$_n$-aminoacyloxy (n=0 or 1-3);

R$_{18}$ is H, —OH, —PO(OH)$_2$ or C$_1$-C$_6$ alkyl; and

R$_{19}$ is H, —(CH$_2$)$_n$—OH, —(CH$_2$)$_n$—N$_3$, alkyl, substituted alkyl, straight, branched or cyclic alkyl, hydroxyalkyl, OCH$_2$PO$_3$, —(CH$_2$)$_n$P(O)(OH)$_2$, —(CH$_2$)$_n$-halogen, —(CH$_2$)$_n$—OCHO, —(CH$_2$)$_n$-alkoxy, —(CH$_2$)$_n$-substituted alkoxy, —(CH$_2$)$_n$ aryloxy, —(CH$_2$)$_n$-aryl, —(CH$_2$)$_n$-thiol, —(CH$_2$)$_n$-acyl, —(CH$_2$)$_n$-acyloxy-(CH$_2$)$_n$-acylamino, —(CH$_2$)$_n$-aminoacyl, —(CH$_2$)$_n$-aminoacyloxy, —(CH$_2$)$_n$amino, or —(CH$_2$)$_n$-substituted amino, (n=0 or 1-12); and X$_3$ is O.

In a preferred embodiment of Formula IA, R$_1$ is methyl, R$_2$ is bromo, R and R$_3$ are H, X, X$_1$, X$_2$ and Y are O, and Z—Z$_1$ is —CH(N$_3$)—CH$_2$. These compounds show excellent anti-HBV and anti-EBV activities, as shown in tables of the examples section of the application.

In a preferred embodiment of Formula IC, R$_1$ is halogen or H, R$_2$ is halogen, R$_8$ is OH, methoxy, ethoxy, or acetoxy, and Z—Z$_1$ is —CH(F-down)-CH$_2$. These compounds show excellent anti-HBV, anti-EBV and anti-herpes activities.

The compounds of Formula 1C as described herein possess unexpectedly high anti-EBV properties, particularly with respect to the following preferred compounds. In a preferred embodiment of Formula 1C, R$_2$ and R$_6$ are F, R$_1$ is ethyl, R$_8$ is methoxy, R, R$_4$, R$_7$ are H, R$_5$ is OH, R$_9$ is CH$_2$OH, X, X$_1$ and X$_2$ are O. This compound shows excellent anti EBV activity with an EC$_{50}$<0.08 µg/mL and EC$_{90}$<0.08 µg/mL, which is significantly lower than that of acyclovir EC$_{50}$=1.0 µg/mL and EC$_{90}$>50 µg/mL.

In a preferred embodiment of Formula ID, R$_{10}$ is CH(N$_3$)=CH$_2$ or I, and R$_{11}$ is

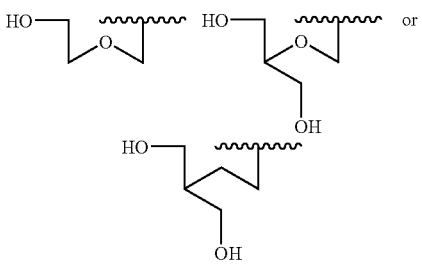

These compounds have shown excellent anti-HBV activity, as shown in Table 1-3 in the Examples section of the application.

The compounds of formulas IA, and 1C, can exist as one or more of the four possible diastereomers. The four possible diastereomers of formula IA are shown below.

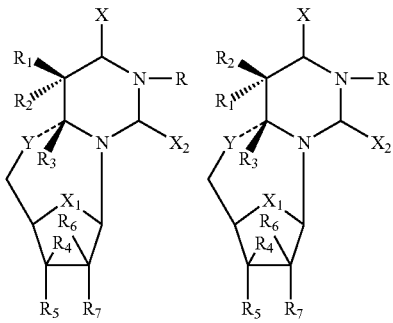

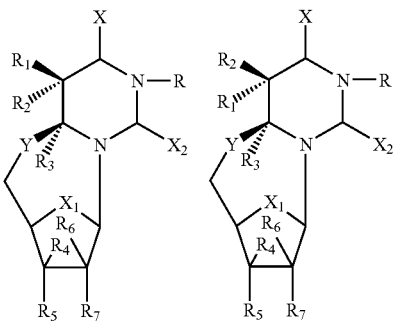

DETAILED DESCRIPTION OF THE INVENTION

This invention is directed to antiviral nucleosides, and methods of preparation and use thereof. The compounds are useful for treating and diagnosing viral infections. Examples of such infections include infections caused by viruses such as hepatitis B virus, and herpes viruses such as Epstein Barr virus. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents at any carbon atom, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxyl, carboxylalkyl, thioaryloxy, thiol, thioalkoxy, substituted thioalkoxy, and nitro. This term is exemplified by groups such as hydroxymethyl, hydroxymethyl, haloethyl, azidomethyl, benzyl, trifluoromethyl, trifluoroethyl, 1-methoxyethyl, 1-azido-2-haloethyl, and the like.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, and nitro. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "aralkyl" refers to the groups -aryl-alkylene and -substituted aryl-alkylene, where the alkylene can be substituted.

The term "alkoxy" refers to the groups alkyl-O—, substituted alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Examples of suitable alkoxy groups include alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of suitable alkylalkoxy groups include alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Examples of suitable alkylthioalkoxy groups include alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms, and having at least 1 and preferably from 1-6 sites of vinyl unsaturation. Examples of alkenyl groups include ethenyl (—CH=CH$_2$), n-propenyl (—CH$_2$CH=CH$_2$), iso-propenyl (—C(CH$_3$)=CH$_2$), 1-propenyl (—CH=CHCH$_3$), allene (—CH=C=CH$_2$), butenyl, and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, and nitro.

The term "alkenylene" refers to a diradical of a branched or unbranched, unsaturated hydrocarbon group preferably having from 2 to 40 carbon atoms, more preferably 2 to 10 carbon atoms and even more preferably 2 to 6 carbon atoms, and having at least 1 and preferably from 1-6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino and nitro.

The term "alkynyl" refers to a monoradical of an unsaturated hydrocarbon preferably having from 2 to 40 carbon atoms, more preferably 2 to 20 carbon atoms and even more preferably 2 to 6 carbon atoms, and having at least 1 and preferably from 1-6 sites of acetylene (triple bond) unsaturation. Examples of suitable alkynyl groups include ethynyl (—C≡CH), propargyl (—CH$_2$C≡CH), —C≡C—CH$_3$, and the like.

The term "substituted alkynyl" refers to an alkynyl group as defined above having from 1 to 5 substituents, and preferably 1 to 3 substituents, selected from the group consisting of alkyl, substituted alkyl, trifluoromethyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, nitro, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, and nitro. This term is exemplified by groups such as —C≡C-halogen, —C≡C-alkyl, —C≡C-amino, —C≡C-aryl, —C≡C-hydroxymethyl, CH$_2$—C≡C-halogen, and the like.

The term "alkynylene" refers to a diradical of an unsaturated hydrocarbon preferably having from 2 to 40 carbon atoms, more preferably 2 to 10 carbon atoms and even more preferably 2 to 6 carbon atoms, and having at least 1 and preferably from 1-6 sites of acetylene (triple bond) unsaturation. Examples of suitable alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino and nitro.

The term "acyl" refers to the groups HC(O)—, alkyl-C(O)—, substituted alkyl-C(O)—; aryl-C(O)—, aralkyl-C(O)—, heteroaryl-C(O)—, and pyrazine-C(O)—, where alkyl, substituted alkyl, aryl, and heteroaryl are as defined herein. Examples of suitable acyl groups include formyl (HCO), acetyl, propionyl (CH$_3$CH$_2$CO) and i-butyryl, benzoyl (C$_6$H$_5$CO).

The term "acylamino" or "aminocarbonyl" refers to the group —C(O)NRR where each R is independently hydrogen, alkyl, substituted alkyl, aryl, aralkyl, amino, heteroaryl, wherein alkyl, substituted alkyl, aryl, and heteroaryl are as defined herein.

The term "aminoacyl" refers to the group —NRC(O)R where each R is independently hydrogen, alkyl, substituted alkyl, amino, substituted amino, aryl, or heteroaryl wherein alkyl, substituted alkyl, aryl, and heteroaryl are as defined herein.

The term "aminothioacyl" refers to the group —NRC(S)R where each R is independently hydrogen, alkyl, substituted alkyl, amino, substituted amino, aryl, or heteroaryl, wherein alkyl, substituted alkyl, aryl, and heteroaryl are as defined herein The term "aminoacyloxy" or "alkoxycarbonylamino" refers to the group —NRC(O)OR where each R is independently hydrogen, alkyl, substituted alkyl, aryl, or heteroaryl, wherein alkyl, substituted alkyl, aryl, and heteroaryl are as defined herein.

The term "acyloxy" refers to the groups alkyl-C(O)O—, substituted alkyl-C(O)O—, alkynyl-C(O)O—, substituted alkynyl-C(O)O—, cycloalkyl-C(O)O—, substituted cycloalkyl-C(O)O—, amino-C(O)O—, substituted amino-C(O)O—, aryl-C(O)O—, alkaryl-C(O)O—, and heteroaryl-C(O)O— wherein alkyl, substituted alkyl, cycloalkyl, substituted cycloalkyl, aryl, alkaryl-C(O)O—, heteroaryl, amino and substituted amino are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Examples of suitable aryl groups include phenyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, substituted alkyl, substituted alkoxy, substituted alkenyl, substituted alkynyl, amino, substituted amino, aminoacyl, acylamino, azido, carboxyl, carboxylalkyl, cyano, halo, nitro, nitroso, aminoacyloxy, oxyacylamino and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

"Alkaryloxy", alone or in combination, means an alkoxy radical as defined above in which at least one hydrogen atom, preferably 1-2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, hydroxyl, amino, cyano, nitroso, acyl, acyloxy, acylamino, alkyl, substituted alkyl, alkoxy, aryloxy, alkenyl, substituted alkenyl, cycloalkenyl, substituted cycloalkenyl, alkynyl, substituted alkynyl, aryl, alkaryl, heteroaryl and heterocyclic provided that both R's are not hydrogen.

The term "alkylcarboxyl" or "alkoxycarbonyl" refers to the groups "—C(O)O-alkyl," "—C(O)O-substituted alkyl," "—C(O)O-cycloalkyl," "—C(O)O-substituted cycloalkyl," "C(O)O-aryl, "—C(O)O-alkenyl," —C(O)O-substituted alkenyl," "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring. Such cycloalkyl groups include, by way of example, single ring structures such as cyclopropyl, cyclobutyl, cyclopentyl, cyclooctyl, and the like.

The term "substituted cycloalkyl" refers to cycloalkyl groups having from 1 to 5 substituents, and preferably 1 to 3 substituents, selected from the group consisting of alkoxy, acyl, amino, azido, cyano, halogen, hydroxyl, carboxyl, carboxyalkyl, aryl, nitro.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclopropenyl, cyclobut-2-enyl, cyclopent-3-enyl, cyclooct-3-enyl, cyclopropenyl and the like.

The term "substituted cycloalkenyl" refers to cycloalkenyl groups having from 1 to 5 substituents, and preferably 1 to 3 substituents, selected from the group consisting of alkoxy, acyl, acyloxy, amino, azido, cyano, halogen, hydroxyl, carboxyl, carboxylalkyl, aryl, nitro.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, and trihalomethyl. Preferred aryl substituents include alkyl, alkoxy, halo, cyano, nitro, trihalomethyl, heteroaryl and thioalkoxy. Such heteroaryl groups can have a single ring (e.g., pyridyl or furyl) or multiple condensed rings (e.g., indolizinyl or benzothienyl). Examples of suitable heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridinylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Examples of suitable heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, pyrrolidine, pyrazolidine, azirine, aziridine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, imidazolidine, imidazoline, piperidine, piperazine, indoline, morpholino, piperidinyl, tetrahydrofuranyl, and the like, as well as N-alkoxy-nitrogen containing heterocycles.

Examples of oxygen heterocycles and heteroaryls include, but are not limited to, oxirane, furane, pyrane, and the like.

Examples of sulphur heterocycles and heteroaryls include, but are not limited to, thiophene, thienyl, parathiazine, and the like.

The term "heterocyclooxy" refers to the group heterocyclic-O—.

The term "thioheterocyclooxy" refers to the group heterocyclic-S—.

The term "heteroocycloalkyl" refers to the group heterocyclic-alkyl-, as exemplified by the groups —(CH$_2$)n-azirine, —(CH$_2$)n-aziridine, —(CH$_2$)n-oxirane, —(CH$_2$)n-O-oxirane, —(CH$_2$)n-O—CH$_2$-oxirane, —(CH$_2$)n-pyrrolidine, where n=0-12.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, amino, substituted amino, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds. It is appreciated by those skilled in the art that the compounds of the present invention include all pharmaceutically acceptable derivatives, prodrugs and analogs thereof.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Examples of other salts include, but are not limited to, the following: adipate, alginate, aspartate, benzenesulfonate, bisulfate, butyrate, camphorate, camphorsulphonate, digluconate, cyclopentanepropionate, dodecylsulfate, ethanesulfonate, glucoheptanoate, glycerophosphate, hemisulfate, heptanoate, hexanoate, hydroiodide, 2-hydroxy-ethanesulfonate, lactate, nicotinate, 2-naphthalenesulfonate, palmoate, pectinate, persulfate, 2-phenylpropionate, picrate, pivalate, propionate, thiocyanate, tosylate, mesylate, and undecanoate. Also, the basic nitrogen-containing groups can be quaternised with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The term "pharmaceutically-acceptable cation" refers to the cation of a pharmaceutically-acceptable salt.

The term "protecting group" or "blocking group" refers to any group which, when bound to one or more hydroxyl, thiol, amino or carboxyl groups of the compounds (including intermediates thereof), prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Examples of suitable removable thiol blocking groups include disulfide groups, acyl groups, benzyl groups, and the like.

Examples of suitable removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC), and the like which can be removed by conventional conditions compatible with the nature of the product.

Examples of suitable carboxyl protecting groups include esters such as methyl, ethyl, propyl, t-butyl, etc., which can be removed by mild conditions compatible with the nature of the product.

The term "optional" or "optionally" means that the subsequently described event, circumstance or substituent may or may not occur, and that the description includes instances where said event or circumstance occurs and instances where it does not.

"Prodrugs" of the compounds of this invention are also contemplated by this invention. A "prodrug" is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives, which are cleaved by esterases in vivo releasing the free drug arid formaldehyde (Bungaard J. Med. Chem. 2503 (1989). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Examples also include lipid prodrugs, which can be hydrolyzed with lipases to form lipids and drugs.

Compounds of formula 1A-1E, in addition to their own activity, metabolites of these compounds may also have antiviral activities.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition" covers all disease states (i.e., pathologic conditions) which are generally acknowledged in the art to be usefully treated.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pseudohalide" refers to functional groups which react in displacement reactions in a manner similar to a halogen. Such functional groups include, by way of example, mesyl, tosyl, azido and cyano groups.

Also within the scope of this invention is the use of ancillary groups which result in the nucleosides being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Examples of suitable lipids include phosphoglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidylethanolamine, dipalmitoylphosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The term "amino acid" as employed herein includes and encompasses all of the naturally occurring amino acids, those amino acids in their D- and L-configurations, and the known non-native, synthetic, and modified amino acids, such as homocysteine, ornithine, norleucine, and valine. A list of non-natural amino acids may be found in "The Peptides", vol. 5, 1983 Academic Press, by D. C. Roberts.

The term "nucleoside" refers to a compound composed of any pentose or modified pentose moiety attached to the natural position of a pyrimidine (1-position) or to the equivalent position in an analog.

The invention comprises both α-anomers as well as β-anomers of the compounds of the formula 1A-1C.

The term "nucleotide" refers to a phosphate ester substituted on the 5'- and/or 3'-position of a nucleoside. A nucleotide can have one, two or three phosphoryl groups. Thus for any given nucleoside, there can be a monophosphate, diphosphate and triphosphate esters. Further, the mono-phosphoryl moiety may be linked to two positions of the pentose for making the 3',5'-cyclic phosphate.

Compounds of formula 1A-1E may contain one or more chiral (asymmetric) centers and exist in different optically active forms. When a compound of formula 1A-1E or a salt thereof contains a single chiral centre it may exist in two enantiomeric forms. The scope of the invention as described and claimed encompasses the individual optical isomers and non-racemic mixtures thereof as well as the racemic forms of the compounds of formula 1A-1E. The enantiomers may be obtained by methods known to those skilled in the art. The optical isomers can be obtained by resolution of the racemice mixtures according to conventional processes e.g., by formation of diastereoisomeric salts, by treatment with an optically active acid or base. Examples of appropriate acids are tartaric, diacetyltartaric, dibenzoyltartaric, ditoluyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, at least one further step will subsequently be required to liberate the desired enantiomeric form. Alternatively, specific enantiomers may be synthesized by asymmetric synthesis using optically active reagents, substrates, catalysts or solvents, or by converting one enantiomer into the other by asymmetric trans formation.

When a compound of formula 1A-1E or a salt thereof contains more than one chiral centre it may exist in diastereoisomeric forms. The diastereoisomeric pairs may be separated by methods known to those skilled in the art, for example, chromatography, sublimation, distillation or crystallization and the individual enantiomers within each pair may be separated as described above. The present invention includes each diastereoisomer of compounds of formula 1A-1E and mixtures thereof.

Some compounds of formula 1A-1E may exist in the form of solvates, for example, hydrates, which also fall within the scope of the present invention.

The term "isomers" refers to different compounds that have the same formula. "Stereoisomers" are isomers that differ only in the way the atoms are arranged in space.

The term "enantiomers" refers to a pair of stereoisomers that are non-superimposable mirror images of each other. A mixture of a pair of enantiomers, in a 1:1 ratio, is a "racemic" mixture.

The "diastereomers" are stereoisomers, which are not mirror-images of each other.

"Epimers" are diastereomers, which differ only in the configuration of one asymmetric center.

One skilled in the art can anticipate that by varying the isomer, enantiomer, stereoisomer, epimer and/or diastereomers of a given compound, their biological activities can be altered, thereby altering their potential use.

The present invention provides composition and method of preparation of novel compounds. The invention also provides unexpected antiviral properties of novel compounds as well as of some known compounds, for which demonstration of antiviral activity against hepatitis B virus and Epstein Barr virus is unexpected. It has been surprisingly found that compounds of the present invention possess potent activity against viruses such as hepatitis B virus and Epstein Barr virus.

It is contemplated that by making a lipophilic and/or pro-drug derivative of the invented compounds by covalently or non-covalently attaching it to moieties such as lipid, fatty acids, alkyl esters, phosphate esters, polyethylene glycol etc., their respective biological properties can be further optimized. In addition, other advantageous properties such as cellular uptake, sustained activity, rapid and efficient absorption from the gastro-intestinal tract, cell membrane penetration, blood brain barrier penetration, higher intracellular concentration, improved dose/effect ratio, sustained release of active compound permitting long intervals between doses, can be obtained.

Nucleosides

The nucleosides are independently selected from a compound of formula IA-IF

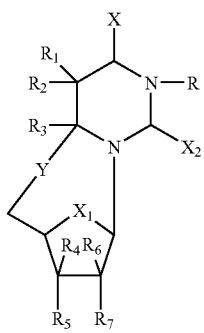

1A

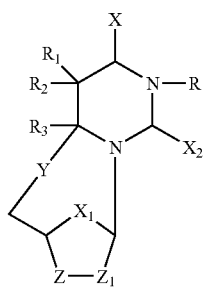

1AA

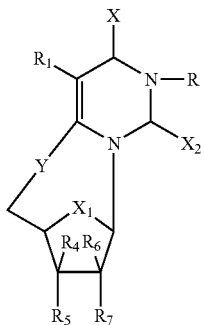

1B

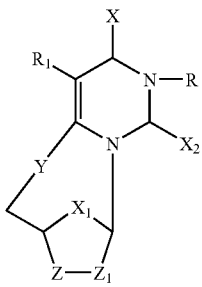

1BB

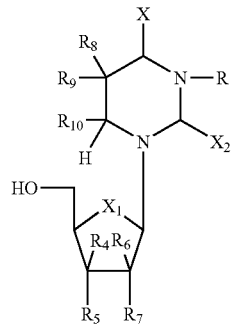

1C

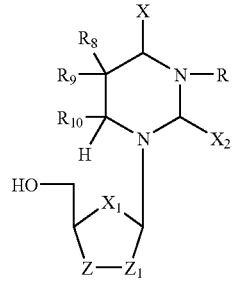

1CC

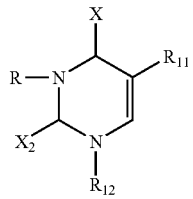

1D wherein:
X is =O, =S, N=CH—N(CH$_3$)$_2$, hydroxyl, alkoxy, =N—OMe, thiol, acyloxy, amino, substituted amino, aminoacyl, or aminoacyloxy, $X_1$ is O or S, $X_2$ is =O, =S, hydroxyl, thiol, amino or substituted amino, $X_3$=O, S, C=CH$_2$, or CHR$_{20}$, Y is O, S, NH or NAc, R is H, alkyl, substituted alkyl, alkaryl, acyl, acylamino, or alkylcarboxyl, $R_1$ is H, halogen, alkyl (linear or branched, unsubstituted or substituted $C_1$-$C_6$ alkyl residue), alkoxy, substituted alkoxy, hydroxyl, amino, substituted amino, aminoacyl, thiol, thioalkoxy, carboxy, alkylcarboxyl, acylamino, acyl, aryl, alkaryl, nitro, cyano, thiocyano, azido, —CH$_2$OCHO or formyl, $R_2$ is H, —OH, —OAc, OMe or halogen, $R_3$ is H, $R_4$, $R_5$, $R_6$, and $R_7$ are independently selected from H, OH, halogens, cyano, N$_3$, CH$_2$OH, COOH, COOalkyl ($C_{1-4}$), NH$_2$, CH$_2$NH$_2$, CH$_2$COOH, thioalkoxy ($C_1$-$C_3$), thiol, ONO$_2$, ONH$_2$, CF$_3$, NO$_2$, CNS, NHCN, CH$_2$N$_3$, NH—($C_{1-4}$ alkyl), CHO, C=CH, alkoxy($C_{1-4}$), or OCH$_2$aryl, and versions thereof wherein —OH and/or —NH$_2$ groups are protected with protecting groups, including esters, amides, phosphates, phosphoesters and phosphamides etc., $R_8$ is H, halogen, or hydroxyl, $R_9$ is H or halogen, $R_{10}$ is H, halogen, hydroxy, alkoxy (preferably $C_{1-18}$ alkoxy), acyloxy, or azido, $R_{11}$ is halogen, hydroxyl, carboxy, formyl, nitro, cyano, azido, alkyl (preferably a linear or branched, unsubstituted or substituted $C_{2-6}$ alkyl residue), alkaryl, —CHR$^{21}$—CH$_2$R$^{22}$, —(CH$_2$)$_n$CHR$^{21}$—CH$_2$R$^{22}$ (wherein R$^{21}$ and R$^{22}$ are, independently of each other, selected from H, OH, $C_{1-6}$ alkyl, alkoxy, substituted alkoxy, halogen, —CF$_3$, azido, nitrato, cyano, —NHCH$_3$, amino, nitro, cyanamido, carboxy, CON$_3$, and aryl, and wherein n=0-3), thiol, thioalkoxy, substituted thioalkoxy, thioaryloxy, alkylalkoxy, alkoxy, substituted alkoxy, acyl, acylamino, aminoacyl, aryl, aryloxy, alkylcarboxyl, amino, substituted amino, alkenyl, substituted alkenyl including —CR$^{23}$=CR$^{24}$—R$^{25}$ and —(CH$_2$)$_n$CR$^{23}$=CR$^{24}$—R$^{25}$ (wherein R$^{23}$, R$^{24}$ and R$^{25}$ are, independently of each other, selected from H, —$C_{1-6}$ substituted or unsubstituted alkyl, —CF$_3$, —CH$_2$OH, alkoxy, substituted alkoxy, nitro, cyano, cyanamido, azido, amino, amido, —CON$_3$, —CON-alkyl, —COOH, —COO-alkyl, aryl and halogen, and wherein n=0-3), alkynyl, substituted alkynyl, including C≡CR$^{26}$ and —(CH$_2$)$_n$C≡CR$^{26}$ $R_{12}$ is and derivatives thereof wherein —OH and/or —NH$_2$ groups are protected with protecting groups, including esters, amides, phosphates, phosphoesters and phosphamides etc., $R_{13}$ and $R_{14}$ can be independently selected from H, OH, halogen, a branched, straight, unsubstituted or substituted alkyl containing 1-16 carbon atoms, aminoacyl, acyloxy, alkoxy, alkylalkoxy, substituted alkoxy, or azido, wherein the dashed line between $R_{13}$ and $R_{14}$ represents a facultative double bond.

$R_{15}$ is and versions thereof wherein —OH and/or —NH$_2$ groups are protected with protecting groups, including esters, amides, phosphates, phosphoesters and phosphamides etc., $R_{16}$=H, alkyl ($C_{1-3}$), (CH$_2$)$_n$—N$_3$, (CH$_2$)$_n$-halogen, (CH$_2$)$_n$-amino, (CH$_2$)$_n$-alkoxy, ($C_{1-3}$), or (CH$_2$)$_n$OH (wherein n=0 or 1-3)

$R_{17}$=H, (CH$_2$)$_n$—OH, COOH, alkyl ($C_{1-3}$), substituted alkyl ($C_{1-3}$), CHOH—CH$_2$OH, CHOH-alkyl ($C_{1-3}$), CHOH—CH$_2$-halogen, CH-halogen-CH$_2$OH, benzyloxy alkyl, (CH$_2$)$_n$—CHO, (CH$_2$)$_n$-aryl, (CH$_2$)$_n$-aryloxy, (CH$_2$)$_n$—N$_3$, (CH$_2$)$_n$-halogen, (CH$_2$)$_n$-amino, (CH$_2$)$_n$-substituted amino, (CH$_2$)$_n$-acyl, (CH$_2$)$_n$-acyloxy, (CH$_2$)$_n$-acylamino, (CH$_2$)$_n$-aminoacyl, (CH$_2$)$_n$-thiol, or (CH$_2$)$_n$-aminoacyloxy (n=0 or 1-3), $R_{18}$=H, —OH, —PO(OH)$_2$ or alkyl ($C_{1-6}$), $R_{19}$=H, —(CH$_2$)$_n$—OH, —(CH$_2$)$_n$—N$_3$, alkyl, substituted alkyl, straight, branched or cyclic alkyl, hydroxyalkyl, OCH$_2$PO$_3$, —(CH$_2$)$_n$P(O)(OH)$_2$, —(CH$_2$)$_n$-halogen, —(CH$_2$)$_n$—OCHO, —(CH$_2$)$_n$-alkoxy, —(CH$_2$)$_n$-substituted alkoxy, —(CH$_2$)$_n$ aryloxy, —(CH$_2$)$_n$-aryl, —(CH$_2$)$_n$-thiol, —(CH$_2$)$_n$-acyl, —(CH$_2$)$_n$-acyloxy-(CH$_2$)$_n$-acylamino, —(CH$_2$)$_n$-aminoacyl,  —(CH$_2$)$_n$-aminoacyloxy,  —(CH$_2$)$_n$ amino, or  —(CH$_2$)$_n$-substituted amino, (n=0 or 1-12), R$_{20}$=H, alkyl, COOH, CONH$_2$, CHO, (CH$_2$)$_n$OH, NHCONH$_2$, OH or halogen, wherein n=0 or 1-3, R$_{26}$ is H, C$_{1-3}$ unsubstituted or substituted alkyl, CF$_3$, alkoxy, CH$_2$OH, nitro, cyano, —NHCN, azido, amino, amido, alkylamino, aryl or halo, and n=0 or 1-3, R$_{27}$ is alkyl (C$_{1-6}$), or substituted alkyl (C$_{1-6}$), R$_{28}$ is halogen, hydroxyl, azido or cyano, R$_{29}$ is OH, acyloxy, alkoxy, amino, substituted amino, alkylcarboxyl, aminoacyl, aminoacyloxy, or mono, di or tri phosphate esters, Z—Z$_1$ is selected from the groups consisting of —CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido).

In a preferred embodiment of Formula IA, R$_1$ is methyl, R$_2$ is bromo, R and R$_3$ are H, X, X$_1$, X$_2$ and Y are O, and Z—Z$_1$ is —CH(N$_3$)—CH$_2$. These compounds show excellent anti-HBV and anti-EBV activities, as shown in tables of the examples section of the application.

In a preferred embodiment of Formula IC, R$_1$ is halogen or H, R$_2$ is halogen, R$_8$ is OH, methoxy, ethoxy, or acetoxy, and Z—Z$_1$ is —CH(F-down)-CH$_2$. These compounds show excellent anti-HBV, anti-EBV and anti-herpes activities.

The compounds of Formula 1C as described herein possess unexpectedly high anti-EBV properties, particularly with respect to the following preferred compounds. In a preferred embodiment of Formula 1C, R$_2$ and R$_6$ are F, R$_1$ is ethyl, R$_8$ is methoxy, R, R$_4$, R$_7$ are H, R$_5$ is OH, R$_9$ is CH$_2$OH, X, X$_1$ and X$_2$ are O. This compound shows excellent anti EBV activity with an EC$_{50}$<0.08 μg/mL and EC$_{90}$<0.08 μg/mL, which is significantly lower than that of acyclovir EC$_{50}$=1.0 μg/mL and EC$_{90}$>50 μg/mL.

In a preferred embodiment of Formula ID, R$_{10}$ is CH(N$_3$)=CH$_2$ or I, and

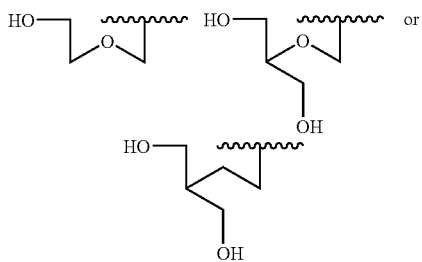

These compounds have shown excellent anti-HBV activity, as shown in Table 1-3 in the Examples section of the application.

Preparation of the Nucleosides

The compounds described herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Suitable reaction conditions for preparing the various nucleoside compounds are either well known in the art or are disclosed in the working examples below.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, N.Y., 1991, and references cited therein.

Protected intermediates can then be deprotected using conventional procedures and reagents to afford deprotected intermediates. For example, tert-butyl esters are readily hydrolyzed with 95% trifluoroacetic acid in dichloromethane; methyl ester can be hydrolyzed with lithium hydroxide in tetrahydrofuran/water; benzyl esters can be removed by hydrogenolysis in the presence of a catalyst, such as palladium on carbon; and 9-fluorenylmethyl esters are readily cleaved using 20% piperidine in DMF. If desired, other well-known protecting groups and deprotecting procedures may be employed in these reactions to form deprotected intermediates.

As will be readily apparent to those of ordinary skill in the art, the synthetic procedures described herein or those known in the art may be readily modified to afford a wide variety of compounds within the scope of this invention.

Compounds of this invention may also be made by the combinatorial and solid phase procedures by a skilled artisan.

The invention is further defined by reference to the following preparative examples, which are intended to be illustrative and not limiting. It will be understood by one of ordinary skill in the art that these examples are in no way limiting and that variations of detail can be made without departing from the spirit and scope of the present invention.

Acylated derivatives of pyrimidine nucleosides are synthesized by reacting a pyrimidine nucleoside or congener with an activated carboxylic acid. An activated carboxylic acid is one that has been treated with appropriate reagents to render its carboxylate carbon more susceptible to nucleophilic attack than is the case in the original carboxylic acid. Examples of useful activated carboxylic acids for synthesis of the compounds of the invention are acid chlorides, acid anhydrides, n-hydroxysuccinimide, esters, or carboxylic acids activated with BOP-UC. Carboxylic acids may also be linked to pyrimidine nucleosides or congeners with coupling reagents like dicyclohexylcarbodiimide (DCC).

During preparation of the acyl compounds of the invention, when the acid source of the desired acyl derivative has groups which interfere with the acylation reactions, e.g., hydroxyl or amino groups, these groups are blocked with protecting groups, e.g., t-butyldimethylsilyl ethers or t-BOC groups, respectively, before preparation of the anhydride. For example, lactic acid is converted to 2-t-butyldimethylsiloxypropionic acid with t-butyldimethylchlorosilane, followed by hydrolysis of the resulting silyl ester with aqueous base. The anhydride is formed by reacting the protected acid with DCC with amino acids, the N-t-BOC derivative is prepared, using standard techniques, which is then converted to the anhydride with DCC. With acids containing more than one carboxylate group (e.g., succinic, fumaric, or adipic acid) the acid anhydride of the desired dicarboxylic add is reacted with a pyrimidine nucleoside in pyridine or pyridine plus dimethylformamide or dimethylacetamide.

Amino acids are coupled to the exocyclic amino, and to hydroxyl groups on the pyrimidine nucleosides or their congeners, by standard methods using DCC in a suitable solvent, particularly a mixture of (i) methylene chloride and (ii) dimethylacetamide or dimethylformamide.

Carbyloxycarbonyl derivatives of non-methylated pyrimidine nucleosides are prepared by reacting the nucleoside with the appropriate carbylchloroformate in a solvent such as pyridine or pyridine plus dimethylformamide under anhydrous conditions. The solvent is removed under vacuum, and the residue is purified by column chromatography.

It will be obvious to the person stilled in the art that other methods of synthesis can be used to prepare the compounds of the invention.

Pharmaceutical Formulations

It is contemplated that compounds according to the present invention will be administered in any appropriate pharmaceutical formulations and under any appropriate protocol.

When used in the treatment, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat immune disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed, the duration of the treatment; drugs used in combination or coincidental with the specific compound employed; and like factors well known in the medical arts. For example, it is well within the skill of the an to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 1000 mg/kg/day of body weight. For purposes of oral administration, more preferable doses may be in the range of from about 0.005 to about 3 mg/kg/day, if desired, the effective daily dose may be divided into multiple doses for purposes of administration; consequently, single dose compositions may contain such amounts or submultiples thereof to make up the daily dose.

In general, a therapeutically effective amount of the present compound in dosage form usually ranges from slightly less than 1 mg/kg to 25 mg/kg of the patient, depending upon the compound used, the condition or infection treated and the route of administration. This dosage range generally produces effective blood level concentrations of active compound ranging from about (0.04 to about 100 micrograms/cc of blood in the patient. It is contemplated, however, that an appropriate regimen will he developed by administering a small amount, and then increasing the amount until either the side effects become unduly adverse, or the intended effect is achieved.

The pharmaceutical compositions of the present invention comprise a compound of the invention and a pharmaceutically acceptable carrier or excipient, which may be administered by a variety of routes including orally, rectally, parenterally, intranasally intracisternally, intravaginally, intraperitoneally, topically (as by powders, ointments, drops, liquid, lotion, cream, paste, gel or transdermal patch), buccally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration, which include intravenous, intramuscular, intraperitoneal, intrasternal, subcutaneous and intraarticular injection and infusion. One skilled in the art of preparing formulations can readily select the proper form and mode of administration depending upon the particular characteristics of the compound selected, the disease state to be treated, the stage of the disease, and other relevant circumstances.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the as required particle size in the case of dispersions, and by the use of surfactants.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula 1A-1E above is employed at no more than about 20 weight percent of the pharmaceutical composition, more preferably no more than about 15 weight percent, with the balance being pharmaceutically inert carrier(s).

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, granules, lozenges, sachets, cachets, and elixirs. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethyl cellulose, alginates, gelatin, polyvinyl pyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, wafers, chewing gums and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions, which can be used include polymeric substances and waxes.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung eye, nose, and ear. Compositions for topical administration, including those for inhalation, may be prepared as a dry powder which may be pressurized or non-pressurized. In nonpressurized powder compositions, the active ingredient in finely divided form may be used in admixture with a larger-sized pharmaceutically acceptable inert carder comprising particles having a size, for example, of up to 100 micrometers in diameter. Suitable inert carders include sugars such as lactose. Deskably, at least 95% by weight of the particles of the active ingredient have an effective particle size in the range of 0.01 to 10 micrometers.

The daily topical dosage regimen will preferably be from 0.1 mg to 150 mg, administered one to four times daily. The daily inhalation dosage regimen will preferably be from about 0.01 mg/kg to about 10 mg/kg per day. It will also be recognized by one of skill in the art that the optimal quantity and spacing of individual dosages of a compound of formula 1A-1E or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula 1A-1E or a pharmaceutically acceptable salt thereof given per day for a defined number of days, can be ascertained by those skilled in the art using conventional course of treatment determination tests.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for inhalation or insufflation include solutions, liposomes, microspheres and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices, which deliver the formulation in an appropriate manner.

Ointments are semi-solid preparations, which are typically based on petrolatum or other petroleum derivatives. The specific ointment base to be used, as will be appreciated by those skilled in the art, is one that will provide for optimum drug delivery, and, preferably, will provide for other desired/characteristics as well. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (WIO) emulsions or oil-in-water (OW) emulsions, and include, for example, cetyl alcohol, glyceryl monostearate, lanolin and stearic acid. Preferred water-soluble ointment bases are prepared from polyethylene glycols of varying molecular weight; again, reference may be Remington: The Science and Practice of Pharmacy, for further information.

Lotions are preparations to be applied to the skin surface without friction, and are typically liquid or semi liquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methyl cellulose, sodium carboxymethyl-cellulose, or the like. A particularly preferred lotion formulation for use in conjunction with the present invention contains propylene glycol mixed with a hydrophilic petrolatum such as that which may be obtained under the trademark Aquaphor® from Beiersdorf, Inc. (Norwalk, Conn.).

Creams containing the selected compounds of the invention are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil so phase in volume, and generally contains a humectant. The emulsifier in a cream formulation, as explained in Remington, supra, is generally a nonionic, anionic, cationic or amphoteric surfactant.

Gels formulations are preferred for application to the scalp. As will be appreciated by those working in the field of topical drug formulation, gels are semisolid, suspension-/type systems. Single-phase gels contain organic macromolecules distributed substantially uniformly throughout the carrier liquid, which is typically aqueous, but also, preferably, contain an alcohol and, optionally, an oil.

Shampoos for treating psoriasis and other skin conditions associated with hyper proliferation and/or an immunologically mediated disorder may be formulated with the selected compounds and standard shampoo components, i.e., cleansing agents, thickening agents, preservatives, and the like, with the cleansing agent representing the primary ingredient, typically an anionic surfactant or a mixture of an anionic and an amphoteric surfactant.

Various additives, known to those skilled in the art, may be included in the topical formulations of the invention. For example, solvents may be used to solubilize certain drug substances. Other optional additives include skin permeation enhancers, opacifiers, anti-oxidants, gelling agents, thickening agents, stabilizers, and the like. Other agents may also be added, such as antimicrobial agents, antifungal agents, antibiotics and anti-inflammatory agents such as steroids.

In the preferred topical formulations of the invention, the active agent is present in an amount which is generally less than 10% by weight of the total composition, preferably less than about 1% by weight, and most preferably less than about 0.1% by weight.

The topical compositions of the invention may also be delivered to the skin using conventional "transdermal"-type patches, wherein the drug composition is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysioxanes, polyisobutylenes, polyacrylates, polyurethanes, and the like. The particular polymeric adhesive selected will depend on the particular drug, vehicle, etc., i.e., the adhesive must be compatible with all components of the drug-containing composition. In an alternative embodiment, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

Compositions for rectal or vagina administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. Liposomes can be introduced by a variety of routes, oral, parenteral, trans-dermal, inhalation etc. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidylcholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

One skilled in the art may further formulate the compounds of this invention in any appropriate manner, and in accordance with accepted practices, such as those disclosed in Remington's Pharmaceutical Sciences, Gennarao, Ed. Mack Publishing Co., Easton, Pa., a standard reference text in this field.

One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulations, esterification etc., which are well within the ordinary skill in the art. It is also well within the ordinary skill of the art to modify the route of administration and dosage regimen of a particular compound in order to of manage the pharmacokinetics of the present compounds for maximum beneficial effect in patients.

In certain pharmaceutical dosage forms, the pro-drug form of the compounds, especially including acylated (acetylated or other), phosphorylated derivatives, pyridine esters and various salt forms of the present compounds are preferred. One of ordinary skill in the art will recognize how to readily modify the present compounds to prodrug forms to facilitate delivery of active compounds to a target site within the host organism or patient. One of ordinary skill in the art will also for take advantage of favorable pharmacokinetic parameters of the prodrug forms, where applicable, in delivering the present compounds to a targeted site within the host organism or patient to maximize the intended effect of the compound.

In addition compounds according to the present invention may be administered alone or in combination with other agents for the treatment of the above infections or conditions. Combination therapies according to the present invention comprise, the administration of at least one compound of the present invention, or a functional derivative thereof, and at least one other pharmaceutically active ingredient. The active ingredient(s) and pharmaceutically active agents may be administered separately or together and when separately in any order. The amounts of the active ingredient(s) and pharmaceutically active agent(s) and the relative timings of administration will be selected in order to achieve the desired combined therapeutic effect.

The pharmaceutical composition can also contain coloring agent and preservatives, as well as perfumes and flavoring additions (e.g., peppermint and eucalyptus oil), and sweetening agents (e.g., saccharine and aspartame).

It is further contemplated that by modification in the compounds of invention, one can achieve enhanced efficacy and/or lower toxicity and thus have a wider therapeutic range. The modification can be advantageous in that the administration of these compounds can be conducted continuously over a prolonged period of time.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |

| Ingredient | Quantity (mg/tablet) |
|---|---|
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

Utility

The compounds described herein are useful for treating or diagnosing viral infections. Examples of viral infections which can be treated using the compounds described herein include DNA viruses, such as, but not limited to HBV, HSV-1, HSV-2, VZV, EBV, HCMV, HHV-6, HHV-8. HHV-8, has similarity to EBV, and has been found to be associated with Kaposi's sarcoma in AIDS patients. The compounds of Formula 1A, 1B and 1C have particular utility with respect to hepatitis B viruses and Epstein Barr viruses. The compounds of Formula 1D have particular utility with respect to hepatitis B virus. The compounds of Formula IC have particular utility with respect to herpes viruses.

Some of the compounds described herein will be useful in gene therapy. Some non-limiting examples of potential use of compounds described here in gene therapy are as follows. Herpes virus encoded thymidine kinase, e.g., HSV-TK and VZV-TK can be used to transfect the tumor cells in the body that makes those transfected cells susceptible to compounds against HSV or VZV, thereby inducing selective inhibition of transfected/transduced tumor cells. Similarly, retroviral vectors are useful to transfer genes of interest for the treatment of various genetic disorders or cancers. Antiviral compounds active for these retroviruses can potentially be used to selectively eliminate the cells harboring these viruses.

In therapeutic applications, compositions are administered to a patient already suffering from, for example, viruses such as EBV, and HBV, in an amount sufficient to at least partially reduce the symptoms. Amounts effective for this use will depend on the judgment of the attending clinician depending upon factors such as the degree or severity of the disorder in the patient, the age, weight and general condition of the patient, and the like. The pharmaceutical compositions may contain more than one of the compounds described herein. The compositions may also include derivatives of the compounds, other known drugs, and combinations thereof.

In certain cases, the compounds can also be administered in prevention of an anticipated exposure risk, i.e., prophylaxis.

The present invention also provides compounds for enhancing the efficacy and/or reducing the toxicity of a therapeutic treatment, preferably treatment with an antiinfective or antiviral drug, anticancer, other immunostimulatory/modulatory compounds or a surgical treatment by administering to an individual, cells or tissues an effective.

The compounds of the present invention can also be used in combination with vitamins, minerals and nutraceuticals etc.

Compounds of formula 1A-1E of the present invention may also be administered in combination with other tumor inhibiting agents, such as 5-fluorouracil, for the treatment of tumors; antiviral such as AZT, 3-TC, ribavirin, acyclovir etc.; antibacterial; anti-parasitic; antifungal; antimycobacterial agents, immunomodulatory agents, vitamins, minerals, hormones, nutraceuticals, vaccines, adjuvants, other alternative treatments such as herbal, natural or traditional medicines.

The individual components of combinations may be administered either sequentially or simultaneously in separate or combined pharmaceutical formulations.

When the compounds of the present invention or a pharmaceutically acceptable derivative thereof is used in combination with a second therapeutic agent, the dose of each compound may be either the same or differ from that when the compound is used alone. Appropriate doses will be readily appreciated by those skilled in the art.

As noted above, the compounds administered to a patient are in the form of pharmaceutical compositions described above which can be administered by a variety of routes including oral, rectal, transdermal, subcutaneous, intravenous, intramuscular, etc. In certain cases, the compounds may be administered as a topical treatment or treatment via inhalation. These compounds are effective as both injectable and oral deliverable pharmaceutical compositions. Such compositions are prepared in a manner well known in the pharmaceutical art and comprise at least one active compound.

The compounds can also be administered in the form of pro-drugs, i.e., as derivatives which are converted into a biologically active compound in vivo, and thus prolong their sojourn in the body. Such pro-drugs will typically include compounds in which, for example, a carboxylic acid group, a hydroxyl group, an amine group or a thiol group is converted to a biologically liable group, such as an ester, lactone or thioester group, or other such group known in the art, which will hydrolyze in vivo to reinstate the respective group. The compounds can also serve as prodrugs of their respective analogs.

The following synthetic and biological examples are offered to illustrate this invention and are not to be construed in any way as limiting the scope of this invention. Unless otherwise stated, all temperatures are in degrees Celsius.

ANALYTICAL EXAMPLES

Example 1

Antiviral Screening Assays

The results are represented by examples shown in Tables 1-5.

Example 2

Anti-HBV Drug Screening Assay

A series of compounds were synthesized and assayed for activity against duck hepatitis B virus (DHBV). Primary cultures of duck hepatocytes were prepared from 9-14 day old DHBV infected ducklings using a modified method (Tuttleman et al., *J. Virol.*, 1986, 58, 17-25). Test compounds were added to the hepatocyte cultures on day 2 and maintained in culture with media changed every second day until day 12. Cell were harvested at day 14 and lysed with buffer containing 1% SDS. DNA was isolated from the lysate and dot blot hybridization was performed using a DHBV (32P) DNA probe. After an autoradiographic image was obtained, the filters were exposed in a phosphoimaging screen for 1-2 hours and samples were quantitated by a Fujix BAS1000 and the percentage density of phosphoimaging units were calculated (B. Lee et al. Antimicrobial agents and Chemotherapy, 1989. 33, 336-339). The test compounds were screened at 10 µg/ml final concentrations.

The compounds were assayed for a) their ability to inhibit DHBV DNA replication in duck hepatocytes, b) their ability to inhibit HBV DNA replication in HepG2 2.2.15 cells, c) the cell cytotoxicity in Vero cells, the cell viability in HFF cells, d) the cell proliferation in HFF cells, and e) the T cell proliferation (purified T cells, PHA stimulated). 3-TC was used as a control. The results are shown in Table 1. Additional compounds described below in the Preparative Examples section were also tested, and the results are shown in Tables 2-4 below. The reference numbers for the compounds are found in the Preparative Examples.

TABLE 1

Examples of anti-HBV activity

| Compd # | % Inhibition of DHBV DNA replication in duck hepatocytes @10 µg/ml | Cell cytotoxicity, Vero cells $CC_{50}$ µM | Cell viability, HFF cells, $CC_{50}$ µM | Cell proliferation (whole human PBLs), $IC_{50}$ µM |
|---|---|---|---|---|
| R-1 | 95.0 ($EC_{50}$ = 0.035 µg/ml) | 34-71 | 173.0 | 34.0 |
| R-13 | 36.0 | >700 | ND | ND |
| R-14 | 81.0 | 100-200 | >350 | >350 |

TABLE 2

| CMPD # | % Inh. of DHBV DNA in duck hepatocytes @ 10 µg/ml [$EC_{50}$, µg/ml] | % Inh. of human HBV DNA replication in HepG2 2.2.15 cells @ 0.1 µg/ml (left) @ 0.01 µg/ml (right) | | Cell Cytotoxicity, Vero cells $CC_{50}$, µg/ml | Cell viability HFF cells $CC_{50}$, µg/ml | Cell proliferation, HFF cells $IC_{50}$, µg/ml | VZV (Ellen) $EC_{50}$, µg/ml | HCMV (AD169) $EC_{50}$, µg/ml |
|---|---|---|---|---|---|---|---|---|
| 7 | 84.0 [0.01-0.1] | ND | ND | >100 | >100 | >100 | ND | ND |
| 8a | 84.1 | 40.0 | 89.4 | >200 | ND | ND | ND | ND |
| 9a | 82.0 [0.3-1.0] | ND | ND | >100 | ND | ND | ND | ND |
| 10b | 75.0 [1-5] | ND | ND | >200 | >100 | >100 | 5.0 | 10.0 |
| 10c | 75.0 [1-5] | ND | ND | >200 | >100 | >100 | 1.0 | 10.0 |
| 13 | 85.6 [0.01-0.1] | 75.4 | 17.0 | >200 | >100 | >100 | ND | ND |
| 19 | 65.2 | 69.1 | 18.1 | >200 | ND | ND | ND | ND |
| 20 | 80.0 [1-3] | ND | ND | >100 | ND | ND | ND | ND |
| 21b | 84.0 [0.1-0.5] | ND | ND | >200 | >100 | >100 | 6.0 | 1.0 |
| 26 | 93.0 [0.01-0.05] | ND | ND | >200 | >100 | >100 | ND | ND |
| 3-TC | 96.0 [0.01-0.05] | 90 | ND | ND | ND | ND | ND | ND |
| ACV | ND | ND | ND | ND | ND | ND | 0.6 | ND |
| GCV | ND | ND | ND | ND | ND | ND | ND | 0.06 |

ND = not determined at this time.
VZV is Varicella zoster virus,
HCMV is human cytomegalovirus,
ACV is acyclovir, and
GCV is ganciclovir.

TABLE 3a

| CMPD # | % Inhibition of DHBV DNA in duck hepatocytes $EC_{50}$ µM | % Inhibition of human HBV DNA replication in HepG2 2.2.15 cells $EC_{50}$ µM | Cell Cytotoxicity, CEM cells $CC_{50}$, µM | Cell Cytotoxicity Vero cells $CC_{50}$, µM | Cell viability HFF cells $CC_{50}$, µM | VZV (Ellen) $EC_{50}$, µg/ml | EBV $EC_{50}$, µg/ml |
|---|---|---|---|---|---|---|---|
| RB-1 & RB-3 | <0.003 | ND | >200 | 300-600 | >285 | ND | ND |
| RB-2 | ND | 2.8 | >200 | ND | >330 | 0.3 | 0.15-0.3 ($EC_{90}$ = 9.8) |
| RB-4 | >10 | 3.0 | ND | ND | ND | ND | ND |
| RB-5 | not active | 5.0 | ND | ND | ND | ND | ND |
| RB-6 & RB-7 | not active | 3.6 | ND | >350 | ND | ND | ND |
| 3-TC | 0.07 | ND | ND | ND | ND | ND | ND |
| Acyclovir | ND | ND | ND | ND | ND | 0.03 | 1.0 ($EC_{90}$ = >50) |

TABLE 3B

| CMPD # | HSV-1 (E-377) $EC_{50}$, µM | HSV-2 (MS) $EC_{50}$, µM | VZV (Ellen) $EC_{50}$, µM | Cell Cytotoxicity Vero cells $CC_{50}$, µM |
|---|---|---|---|---|
| *RB-10 | 0.33 | 1.6 | 9.8 | >327 |
| Acyclovir | 3.08 | 6.16 | 3.96 | >400 |

*5-Chloro-6-azido-5,6-dihydro-2'-deoxyuridine

Example 3

Cell Cytotoxicity Assay

Twenty-four hours prior to assay HFF cells were plated into 96 well plates at a concentration of $2.5 \times 10^4$ cells per well. After 24 h, the media was aspirated and 125 µL of drug was added to the first row of wells and then diluted serially 1:5 using the automated Cetus Liquid Handling System in a manner similar to that used in the CPE assay. The plates were incubated for 7 days in a $CO_2$ incubator at 37° C. At this time the media/drug was aspirated and 200 µL/well of 0.01% neutral red in Dulbecco's Phosphate Buffered Saline (DPBS) was added. This was incubated in the $CO_2$ incubator for 2 h, the dye was aspirated and the cells were washed using a Nunc Plate Washer. After removing the DPBS wash, 200 µg/well of 50% EtOH:1% glacial acetic acid in water was added. The plates were rotated for 15 min. and the optical densities were read at 550 nm on a plate reader. The results of the assays are shown in Tables 1-5.

Example 4

Cell Proliferation Assay

Twenty-four hours prior to assay, HFF cells were seeded in 6-well plates at a concentration of $2.5 \times 10^4$ cells per well in MEM containing 10% FBS. On the day of the assay, drugs were diluted serially in MEM containing 10% FBS at increments of 1:5 covering a range from 100 µg/mL to 0.03 µg/mL. For drugs that have to be solubilized in DMSO, control wells received MEM containing 10% DMSO. The media from the wells was then aspirated and 2 mL of each drug concentration was then added to each well. The cells were incubated in a $CO_2$ incubator at 37° C. for 72 h. At the end of this time, the media-drug solution was removed and the cells were washed. One mL of 0.25% trypsin was added to each well and incubated until the cells start to come off of the plate. The cell-media mixture was then pipetted up and down vigorously to break up the cell suspension and 0.2 mL of the mixture was added to 9.8 mL of isoton III and counted using a Coulter Counter. Each sample was counted three times with three replicate wells per sample. The results of the assays are shown in Tables 1-5.

Example 5A

In Vitro Anti-Herpes Virus Activity

Cytopathic effect (CPE) inhibition assays for HSV-1, HSV-2, HCMV and VZV were performed as follows: Low passage human foreskin fibroblasts (HFF) cells were seeded into 96 well tissue culture plates 24 h prior to use at a cell concentration of $2.5 \times 10^4$ cells per mL in 0.1 mL of minimal essential medium (MEM) supplemented with 10% fetal bovine serum (FBS). The cells were then incubated for 24 h at 37° C. in a $CO_2$ incubator. After incubation, the medium was removed and 100 µL of MEM containing 2% FBS was added to all but the first row. In the first row, 125 µL of experimental drug was added in triplicate wells. Medium alone was added to both cell and virus control 37° C. in $CO_2$ incubator. After incubation, the medium was removed and 100 µl of MEM containing 2% FBS was added to all but the first row. Medium alone was added to both cell and virus control wells. 125 µl of Experimental drug was added in triplicate wells. The drug in the first row of wells was then diluted serially 1:5 throughout the remaining wells by transferring 25 µL using the Cetus Liquid Handling Machine. After dilution of drugs, 100 µL of the appropriate virus concentration was added to each well, excluding the cell control wells which received 100 µL of MEM. For HSV-1 and HSV-2 assays, the virus concentration utilized was 1000 PFU's per well. For CMV and VZV assays, the virus concentration added was 2500 PFU's per well. The plates were then incubated at 37° C. in a $CO_2$ incubator for 3 days for HSV-1 and HSV-2, 10 days for VZV, or 14 days for CMV. After the incubation period, media was aspirated and the cells stained with a 0.1% crystal violet solution for 30 min. The stain was then removed and the plates were allowed to dry 24 h and then read on a Skatron Plate Reader at 620 nm.

The immunofluorescence assay, using monoclonal antibodies, for Epstein-Barr Virus (EBV) was performed as follows: DAUDI cells were infected with the P3HR-1 strain of EBV and the test drug was added after adsorption (45 min. at 37° C.) and washing of the cell cultures. These cultures were then incubated for 2 days in complete medium to allow viral gene expression. Following the 48 h incubation period, the number of cells in each sample were counted and smears were made. Monoclonal antibodies to the different early antigen (EA) components and VCA were than added to the cells, incubated and washed. This was followed by the addition of a fluorescein conjugated rabbit anti mouse Ig antibodies. The number of fluorescence positive cells in the smears were counted and the total number of cells in the cultures positive for EA or VCA were then calculated and compared. Data is shown in Tables 2-5.

TABLE 4

| | Examples of Anti-Herpes Activity | | | | | | |
|---|---|---|---|---|---|---|---|
| Cmpd # | HSV-1 (KOS) HSV-TK+ EC50, µg/ml | HSV-1 (KOSSB) HSV-TK− EC50, µg/ml | HSV-1 (E-377) EC50, µg/ml | HSV-2 (MS) EC50, µg/ml | VZV (Ellen) EC50, µg/ml | EBV EC50, µg/ml | HCMV (AD-169) EC50, µg/ml |
| R-1 | 10-25 | 1-10 | 20 | 20 | >100 | 1.4 | 20 |
| R-9 | 1-5 | 10-25 | 4.0 | 10 | ND | ND | ND |
| R-13 | >25 | >50 | ND | ND | ND | ND | ND |
| R-14 | >25 | >50 | >100 | >100 | >100 | <0.08 | >100 |
| R-23 | >25 | >50 | >100 | >100 | >100 | 0.1-1.4 ($EC_{90} = 7.3$) | >100 |
| R-24 | >25 | >50 | >100 | >100 | >100 | 0.6-2.8 ($EC_{90} = 3.8$) | >100 |
| R-25 | >25 | >50 | >100 | >100 | >100 | 0.6-3.0 | >100 |

TABLE 4-continued

Examples of Anti-Herpes Activity

| Cmpd # | HSV-1 (KOS) HSV-TK+ EC50, µg/ml | HSV-1 (KOSSB) HSV-TK− EC50, µg/ml | HSV-1 (E-377) EC50, µg/ml | HSV-2 (MS) EC50, µg/ml | VZV (Ellen) EC50, µg/ml | EBV EC50, µg/ml | HCMV (AD-169) EC50, µg/ml |
|---|---|---|---|---|---|---|---|
| Acyclovir | <1 | >100 | 0.2 | 0.6 | 0.08 | 1.4 ($EC_{90}$ = >50) | ND |
| Gancyclovir | ND | ND | ND | ND | 0.1 | ND | 0.1 |

HSV-1 is Herpes simplex virus type-1;
HSV-2 is Herpes simplex virus type-2;
HCMV is human cytomegalovirus;
VZV is varicella zoster virus;
EBV is Epstein Barr virus.

Example 5B

In Vitro Anti-EBV and Anti-HBV Activity

TABLE 5

| CMPD # | % Inhibition of DHBV DNA in duck hepatocytes @10.0 µg/ml | % Inhibition of DHBV DNA in duck hepatocytes @1.0 µg/ml | Cell Cytotoxicity Vero cells $CC_{50}$, µg/ml | Cell viability HFF cells $CC_{50}$, µg/ml | EBV $EC_{50}$, µg/ml |
|---|---|---|---|---|---|
| *RC-1 | ND | ND | >100 | >100 | <0.08 ($EC_{90}$ = <0.08) |
| **RC-2 | 100 | 96 | >100 | >100 | ND |
| ***RC-3 | 100 | 96 | >100 | >100 | ND |
| 3-TC | 100 | 95 | >100 | >100 | ND |
| Acyclovir | ND | ND | ND | ND | 1.0 ($EC_{90}$ = >50) |

*5-Ethyl-5-fluoro-6-methoxy-5,6-dihydro-2'-arabinofluoro-2'-deoxyuridine
**5-Ethyl-5-bromo-6-ethoxy-5,6-dihydro-2'-arabinofluoro-2'-deoxyuridine
***5-Ethyl-5-bromo-6-isopropyloxy-5,6-dihydro-2'-arabinofluoro-2'-deoxyuridine

PREPARATIVE EXAMPLES

In the examples which follow, the synthesis of various compounds described herein is provided.

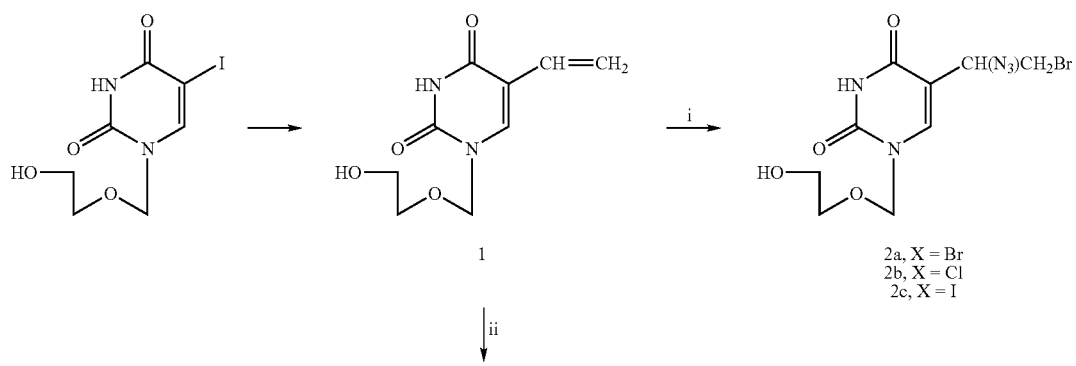

Scheme 1

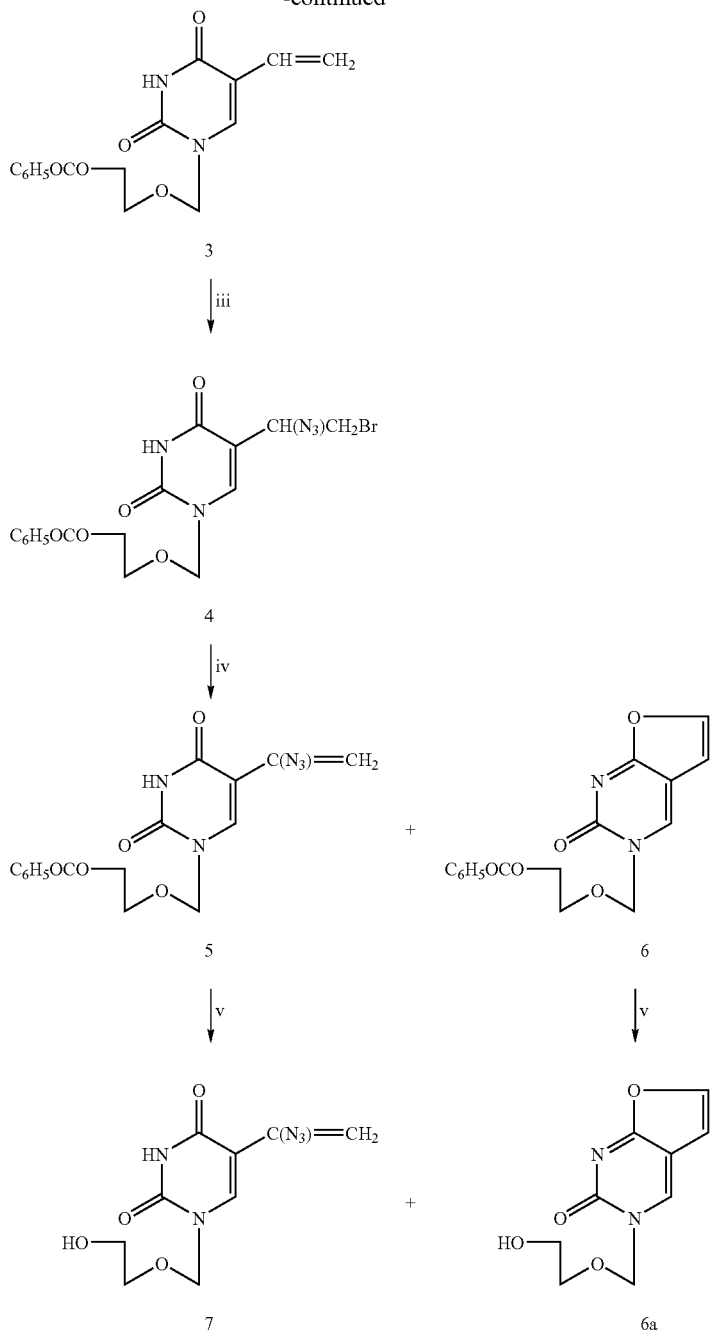

i, N-Bromosuccinimide (NBS), sodium azide, DME, water (2a); N-chlorosuccinimide, sodium azide, DME, water (2b); Iodine monochloride (ICl), sodium azide, acetonitrile, 0-5° C. (2c); ii, Benzoyl chloride, pyridine, 25° C., 6 h; iii, NBS, sodium azide, DME, water; iv, t-BuOK, THF, 0° C.; v, Ammonia, methanol, 25° C.

Example 6A

Preparation of 1-[(2-hydroxyethoxy)methyl]-5-vinyluracil (1)

A mixture of palladium (II) acetate (26 mg, 0.11 mmol), triphenylphosphine (57 mg, 0.21 mmol) and triethylamine (1.5 mL), (dried over calcium hydroxide) in dry DMF (25 mL) was maintained at 70° C. with stirring until an intense red color appeared. 1-[(2-hydroxyethoxy)methyl]-5-iodouracil (683 mg, 2.19 mmol) and vinyl acetate (10 mL, 110 mmol) were then added, and the reaction was allowed to proceed at 70° C. for 6 h with stirring. The solvent was removed in vacuo and the residue obtained was extracted with water (2×50 mL). The water layer was washed with dichloromethane (3×20 mL), evaporated in vacuo, and the residue obtained was purified by elution from a silica gel column using ethyl acetate-methanol (95:5, v/v) as eluent to give 1 as viscous oil (250 mg, 54%).

$^1$H-NMR (DMSO-$d_6$) δ 3.50 (m, 4H, OCH$_2$CH$_2$), 4.70 (br, 1H, OH), 5.15 (m, 3H, NCH$_2$, CH=CHH'), 5.98 (dd, J=18 Hz, J=2.1 Hz, 1H, CH=CHH'), 6.38 (dd, J=18 Hz, J=11 Hz, 1H, CH=CHH'), 7.95 (s, 1H, H-6), 11.48 (s, 1H, NH, exchanges with D$_2$O). Anal. (C$_9$H$_{12}$N$_2$O$_4$) C, H, N.

Example 6B

Preparation of 1-[(2-Hydroxyethoxy)methyl]-5-(1-Azido-2-bromoethyl)-uracil (2a)

N-bromosuccinimide (NBS, 110 mg, 0.61 mmol) was added in aliquots to a precooled (−5° C.) suspension prepared by mixing a solution of 1 (130 mg, 0.61 mmol) in 1,2-dimethoxyethane (10 ml) with a solution of sodium azide (160 mg, 2.46 mmol) in water (0.4 ml). The initial yellow color produced upon addition of each NBS aliquot quickly disappeared. When all the NBS had reacted, the reaction mixture was stirred for 15 min. at 0° C., poured onto ice-water (25 ml), and extracted with ethyl acetate (3×50 ml). The ethyl acetate extract was washed with cold water (10 ml), dried ($Na_2SO_4$), the solvent was removed in vacuo, and the residue obtained was purified by elution from a silica gel column using chloroform:methanol (97:3, v/v) as eluent to give 2a (71 mg, 35%) as a viscous oil.

$^1$H-NMR (DMSO-$d_6$) δ: 3.52 (m, 4H, OCH$_2$CH$_2$O), 3.85 (m, 2H, CH$_2$Br), 4.70 (br, 1H, OH), 4.85 (m, 1H, CHN$_3$), 5.15 (s, 2H, N—CH$_2$), 7.90 (s, 1H, H-6), 11.6 (br, 1H, NH). Anal. ($C_9H_{12}N_5O_5Br$) C,H,N.

Example 7

Preparation of 1-[(2-Hydroxyethoxy)methyl]-5-(1-Azido-2-chloroethyl)-uracil (2b)

N-Chlorosuccinimide (NCS, 88 mg, 0.65 mmol) was added slowly to a precooled (−5° C.) suspension prepared by mixing a solution of 1 (116 mg, 0.55 mmol) in 1,2-dimethoxyethane (20 ml) with a solution of sodium azide (143 mg, 2.2 mmol) in water (0.35 ml). The reaction was stirred for 3 h at 0° C. Completion of the reaction, as described for the isolation of 2a, gave a residue which was purified by silica gel column chromatography. Elution with chloroform:methanol (97:3, v/v) as eluent yielded 2b as a syrup (56 mg, 35%).

$^1$H-NMR (DMSO-$d_6$) δ: 3.52 (m, 4H, OCH$_2$CH$_2$O), 4.0 (m, 2H, CH$_2$Cl), 4.70 (br, 1H, OH), 4.80 (m, 1H, CHN$_3$), 5.18 (s, 2H, N—CH$_2$), 7.92 (s, 1H, H-6), 11.68 (br, 1H, NH). Anal. ($C_9H_{12}N_5O_5Cl$) C,H,N.

Example 8

Preparation of 1-[(2-Hydroxyethoxy)methyl]-5-(1-Azido-2-iodoethyl)-uracil (2c)

Iodine monochloride (92 mg, 0.56 mmol) was added slowly during a five minute period to a suspension of sodium azide (129 mg, 2.0 mmol) in dry acetonitrile (10 ml) at ice-bath temperature with stirring. This mixture was stirred for a further 5 min., a solution of 1 (105 mg, 0.49 mmol) in dry acetonitrile (15 ml) was added, the reaction mixture was stirred at 0° C. for 30 min. The resulting red-brown colored reaction mixture was poured onto ice cold water (25 ml), the mixture was extracted with ethyl acetate (3×50 ml) and the ethyl acetate extract was washed with 5% aqueous sodium thiosulfate (50 ml). Drying the colorless ethyl acetate fraction ($Na_2SO_4$), removal of the solvent in vacuo and purification of the residue obtained by elution from a silica gel column using chloroform:methanol (93:7, v/v) as eluent afforded 2c (65 mg, 34%) as a viscous oil.

$^1$H-NMR (DMSO-$d_6$) δ: 3.50 (m, 4H, OCH$_2$CH$_2$O), 3.65 (m, 2H, CH$_2$I), 4.70 (m, 2H, OH, CHN$_3$), 5.12 (s, 2H, N—CH$_2$), 7.90 (s, 1H, H-6), 11.70 (br, 1H, NH). Anal. ($C_9H_{12}N_5O_5I$) C,H,N.

Example 9

Preparation of 1-[(2-benzoyloxyethoxy)methyl]-5-vinyluracil (3)

Benzoylchloride (410 mg, 2.9 mmol) was added to a solution of 1 (614 mg, 2.89 mmol) in dry pyridine (30 ml) and the reaction was allowed to proceed at 25° C. with stirring for 6 h. Removal of the solvent in vacuo and purification of the product by elution from a silica gel column using chloroform-methanol (99:1, v/v) as eluent gave 3 as a viscous oil (615 mg, 67.3%) which was used directly in the next reaction step.

Example 10

Preparation of 1-[(2-benzoyloxyethoxy)methyl]-5-(1-Azido-2-bromoethyl)-uracil (4)

N-Bromosuccinimide (NBS, 350 mg, 1.96 mmol) was added in aliquots to a precooled (−5° C.) suspension prepared by mixing a solution of 3 (61 mg, 1.95 mmol) in 1,2-dimethoxyethane (25 ml) with a solution of sodium azide (510 mg, 7.84 mmol) in water (1.2 ml). The initial yellow color faded away after each addition. When all the NBS was consumed, the reaction mixture was allowed to stand at 0° C. for 30 min., prior to pouring onto ice-water (25 ml), and extraction with dichloromethane (3×50 ml). The dichloromethane extract was washed with cold water (25 ml), dried ($Na_2SO_4$), the solvent was removed in vacuo to yield a residue which was purified by elution from a silica gel column using chloroform:methanol (98:2, v/v) as eluent to yield 4 (388 mg, 45.5%) as a viscous oil which was used in the next reaction.

Example 11

Preparation of [(2-benzoyloxyethoxy)methyl]-5-(1-azidovinyl)uracil (5), and 5-[(2-benzoyloxyethoxy)methyl]-[2,3-d]pyrimidin-6-(5H)-one (6)

Potassium tert-butoxide (425 mg, 1.87 mmol) was added to a suspension of 4 (832 mg, 2.58 mmol) in dry THF (100 ml) at −5° C. with stirring. The cooling bath was removed and the reaction mixture was stirred at 0° C. for 3 h. Removal of the solvent in vacuo gave a residue which was dissolved in dichloromethane (50 ml), washed with cold water (25 ml), the dichloromethane fraction was dried ($Na_2SO_4$), and the solvent was removed in vacuo. The reaction mixture was separated by silica gel column chromatography using chloroform-methanol (95:5, v/v) as eluent to give two products which eluted in the following order:

Fraction 1; (5) (358 mg, 38.7%); m.p. 129° C.; $^1$H-NMR (CDCl$_3$) δ: 3.98 and 4.50 (2m, 4H, OCH$_2$CH$_2$O), 5.08 [d, J=2 Hz, 1H, C(N$_3$)=CHH'], 5.30 (s, 2H, OCH$_2$N), 6.33 [d, J=2 Hz, 1H, C(N$_3$)=CHH'], 7.40-8.10 (m, 6H, H-6, AraH), 8.65 (s, 1H, NH). Anal. ($C_{16}H_{15}N_5O_5$) C,H,N.

Fraction 2; (6) (80 mg, 9.8%); m.p. 180° C.; $^1$H-NMR (CDCl$_3$) δ: 4.08 and 4.50 (2m, 4H total, OCH$_2$CH$_2$O), 5.52 (s, 2H, N—CH$_2$O), 6.40 (d, J=2.5 Hz, 1H, OCH=CH), 7.32 (d, J=2.5 Hz, 1H, OCH=CH), 7.40-8.02(m, 5H, AraH), 8.10 (2, 1H, H6). Anal. ($C_{16}H_{14}N_2O_5$) C,H,N.

Example 12

Preparation of 1-[(2-hydroxyethoxy)methyl]-5-(1-azidovinyl)-uracil (7)

A solution of 5 (357 mg, 1.0 mmol) in a saturated solution of ammonia in methanol (50 ml) was stirred at 25° C. for 84 h. Removal of solvent in vacuo yielded a residue which was purified by silica gel column chromatography using chloroform-methanol (92:8, v/v) as eluent to yield 7 (154 mg, 60.8%) as a solid; m.p. 141-142° C.; $^1$H-NMR (DMSO-$d_6$) δ: 3.50 (m, 4H, OCH$_2$CH$_2$O), 4.72 (m, 1H, OH), 5.03 [d, J=2 Hz, 1H, C(N$_3$)=CHH'], 5.18 (s, 2H, N—CH$_2$O), 5.95 [d, J=2 Hz, 1H, C(N$_3$)=CHH'], 7.98 (s, 1H, H-6), 11.68 (br, 1H, NH). Anal. (C$_9$H$_{11}$N$_5$O$_4$) C,H,N.

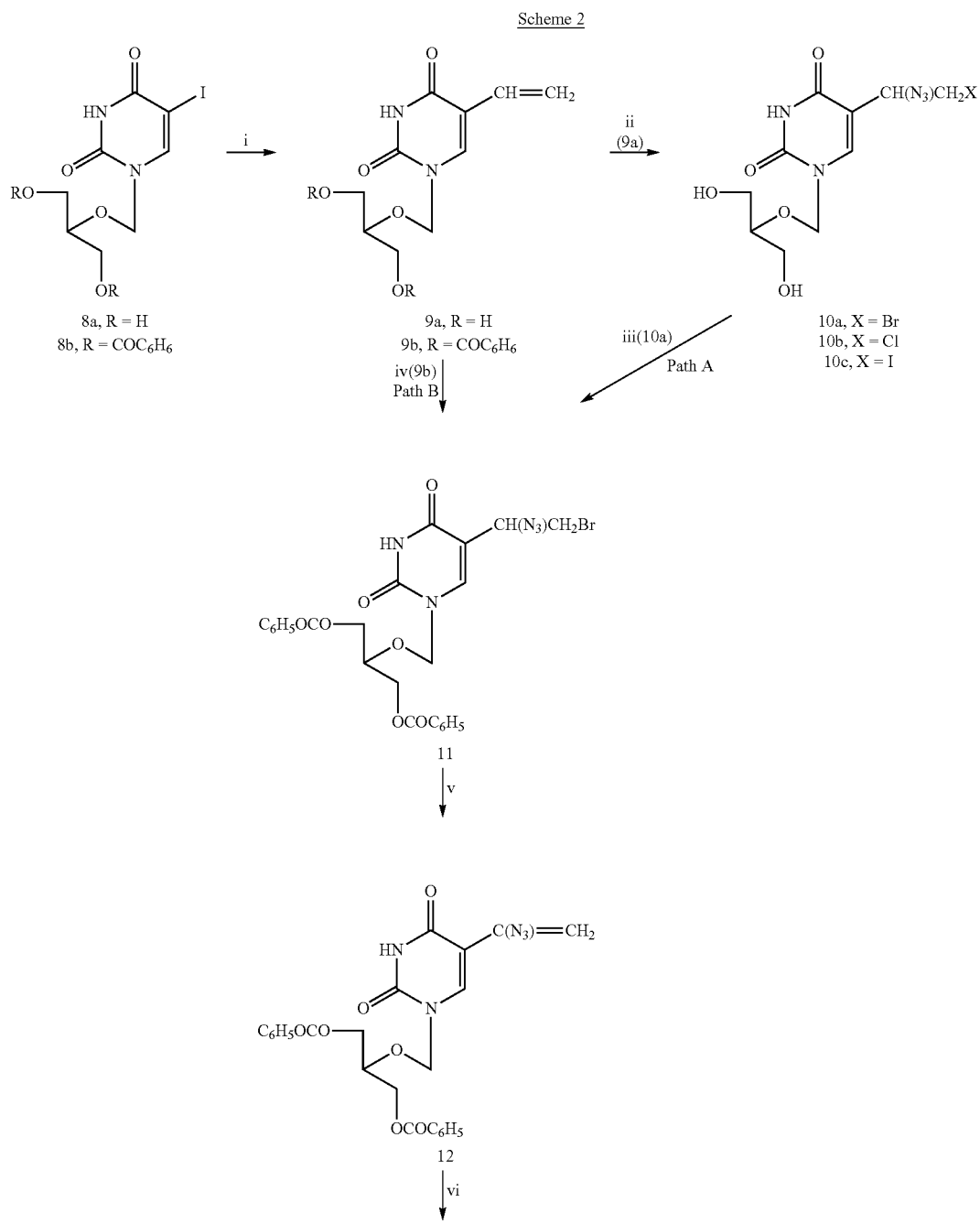

Scheme 2

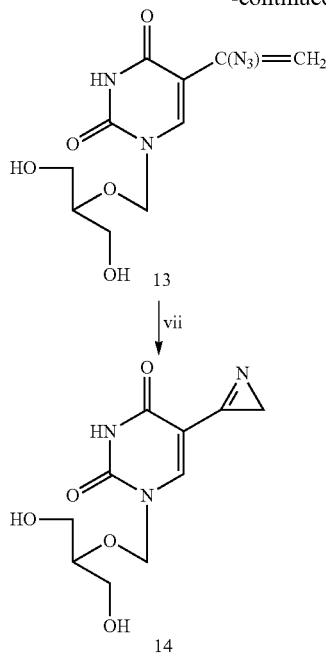

i, Vinyl acetate, palladium (II) acetate, triethylamine, triphenylphosphine, 70° C., 6 h; ii, NBS, sodium azide, DME, water (10a), NCS, sodium azide, DME, water, 0-25° C., 10 h (10b), ICl, sodium azide, acetonitrile (10c); iii, Benzoyl chloride, pyridine, 25° C.; iv, NBS, sodium azide, DME; v, t-BuOK, THF, 0° C.; vi, Ammonia, methanol, 25° C.; vii, Dioxane, 110° C

Example 13

Preparation of 1-[(2-Hydroxy-1-(hydroxymethyl)ethoxy)methyl]-5-vinyluracil (9a)

A mixture of palladium (II) acetate (26 mg, 0.11 mmol), triphenylphosphine (0.57 mg, 0.216 mmol) and triethylamine (1.5 ml), (dried over calcium hydroxide) in dry DMF (25 ml) was maintained at 70° C. with stirring until an intense red color appeared. Compound 8a (L. M. Beuchamp et al, *J. Med. Chem.*, 31, 144-1988) (750 mg, 2.19 mmol) and vinyl acetate (10 ml, 110 mmol) were then added, and the reaction was allowed to proceed at 70° C. for 6 h with stirring. The solvent was removed in vacuo and the residue obtained was purified by elution from a silica gel column starting with ethyl acetate and then changing to ethyl acetate-methanol (97:3, v/v). Removal of the solvent from the combined fractions containing the desired products yielded 9a (250 mg, 47%) as a syrup.

$^1$H-NMR (DMSO-$d_6$) δ: 3.40 (m, 4H, CH$_2$), 3.55 (m, 1H, CH), 4.65 (m, 2H, OH), 5.10 (dd, J=11 Hz, J=2.1 Hz, 1H, —CH=CHH'), 5.20 (s, 2H, NCH$_2$O), 5.95 (dd, J=18.0 Hz, J=2.1 Hz, 1H, —CH=CHH'), 6.35 (dd, J=18 Hz, J=11.0 Hz, 1H, —CH=CHH'), 7.90 (s, 1H, H-6), 11.40 (br s, 1H, NH, exchange with D$_2$O). Anal. (C$_{10}$H$_{14}$N$_2$O$_5$) C,H,N.

Example 14

Preparation of 1-[(2-Benzoyloxy-1-(benzoyloxymethyl)ethoxy)methyl]-5-vinyluracil (9b)

Reaction of 8b (L. M. Beuchamp et al, *J. Med. Chem.*, 31, 144-1988) (1.0 gm, 1.81 mmol) with vinyl acetate (8.0 ml, 88 mmol), using the procedure outlined for the preparation of 9a, and purification of the product by silica gel column chromatography using chloroform-methanol (98:2, v/v) as eluent afforded 9b as a viscous oil (480 mg, 59%).

$^1$H-NMR (CDCl$_3$) δ: 4.4-4.65 (m, 5H, CH, CH$_2$O), 5.20 (dd, J=11 Hz, J=2.1 Hz, 1H, —CH=CHH'), 5.38 (m, 2H, N—CH$_2$O), 5.86 (dd, J=18.0 Hz, J=2.1 Hz, 1H, —CH=CHH'), 6.28 (dd, J=18 Hz, J=11.0 Hz, 1H, —CH=CHH'), 7.30-8.05 (m, 11H, H-6, AraH), 8.26 (s, 1H, NH). Anal. (C$_{24}$H$_{22}$N$_2$O$_7$) C,H,N.

Example 15

Preparation of 1-[(2-Hydroxy-1-(hydroxymethyl)ethoxy)methyl]-5-(1-azido-2-bromoethyl)uracil (10a)

Reaction of 9a with N-bromosuccinimide, using the procedure outlined for the preparation of 2a, and purification of the product by silica gel column chromatography using chloroform-methanol (92:8, v/v) as eluent provided 10a as a syrup (92 mg, 31.4%).

$^1$H-NMR (DMSO-$d_6$) δ: 3.40-3.60 (m, 5H, CH, CH$_2$O), 3.85 (m, 2H, CH$_2$Br), 4.65 (m, 2H, OH), 4.80 (m, 1H, CHN$_3$), 5.20 (s, 2H, NCH$_2$), 7.90 (s, 1H, H-6), 11.65 (s, 1H, NH, exchange with D$_2$O). Anal. (C$_{10}$H$_{14}$N$_5$O$_5$Br) C,H,N.

Example 16

Preparation of 1-[(2-Hydroxy-1-(hydroxymethyl)ethoxy)methyl]-5-(1-azido-2-chloroethyl)uracil (10b)

Reaction of 9a with N-chlorosuccinimide, using the procedure outlined for the preparation of 2b, and purification of the product by silica gel column chromatography using dichloromethane-methanol (90:10, v/v) as eluent yielded 10b as a syrup (75 mg, 57%).

$^1$H-NMR (DMSO-$d_6$) δ: 3.38-3.58 (m, 5H, CH, CH$_2$O), 3.95 (m, 2H, CH$_2$Cl), 4.65 (m, 2H, OH), 4.78 (m, 1H, CHN$_3$), 5.20 (s, 2H, NCH$_2$), 7.90 (s, 1H, H-6), 11.60 (s, 1H, NH, exchange with D$_2$O). Anal. (C$_{10}$H$_{14}$N$_5$O$_5$Cl) C,H,N.

Example 17

Preparation of 1-[(2-Hydroxy-1-(hydroxymethyl) ethoxy)methyl]-5-(1-azido-2-iodoethyl)uracil (10c)

Reaction of iodine monochloride (72.0 mg, 0.44 mmol) with 9a (95 mg, 0.39 mmol), using the procedure described for the preparation of 2c, and purification of the product by silica gel column chromatography using chloroform-methanol (90:10, v/v) as eluent afforded 10c as a syrup (48 mg, 29.6%).
$^1$H-NMR (CD$_3$OD) δ: 3.5-3.74 (complex m, 7H, CH, CH$_2$O, CH$_2$I), 4.65 (m, 1H, CHN$_3$), 5.34 (s, 2H, NCH$_2$), 7.78 (s, 1H, H-6). Anal. (C$_{10}$H$_{14}$N$_5$O$_5$I) C,H,N.

Example 18

Preparation of 1-[(2-benzoyloxy-1-(benzoyloxymethyl)ethoxy]methyl)]-5-(1-azido-2-bromoethyl) uracil (11). Path A Benzoylchloride (15 mg, 0.11 mmol) was added to a solution of 10a (18.2 mg, 0.05 mmol) in dry pyridine (5 ml) at 0-5° C. with stirring. The reaction mixture was allowed to proceed at 25° C. with stirring for 6 h, ice-water (5 ml) was added and the solvent was removed in vacuo. The residue obtained was purified by PTLC using dichloromethane-methanol (98:2, v/v) as development solvent to yield 11 (15 mg, 52%) as a viscous oil.
$^1$H-NMR (CDCl$_3$) δ: 3.45 (m, 1H, CHH'Br), 3.65 (m, 1H, CHH'Br), 4.40-4.65 (complex m, 6H, CH, CH$_2$O, CHN$_3$), 5.35 (m, 2H, NCH$_2$), 7.38-8.04 (m, 11H, H-6, AraH), 8.30 (s, 1H, NH). Anal. (C$_{24}$H$_{22}$N$_5$O$_7$Br) C,H,N.

Example 19

Preparation of 1-[(2-benzoyloxy-1-(benzoyloxymethyl)ethoxy]methyl)]-5-(1-azido-2-bromoethyl) uracil (11). Path B Reaction of 9b (30.0 mg, 0.066 mmol) with N-bromosuccinimide (13.0 mg, 0.073 mmol), using the procedure described for the preparation of 4, and purification of the product by silica gel column chromatography using dichloromethane-methanol (97:3, v/v) as eluent afforded 11 as a viscous oil (32 mg, 84.8%). $^1$H-NMR spectrum was identical to that of 11 synthesized by path A.

Example 20

Preparation of 1-[(2-benzoyloxy-1-(benzoyloxymethyl)ethoxy]methyl)]-5-(1-azidovinyl)uracil (12)

Potassium tert-butoxide (243 mg, 2.16 mmol) was added to a suspension of 11 (620 mg, 1.08 mmol) in dry THF (250 ml) at −5° C. with stirring. The cooling bath was removed and the reaction mixture was stirred at 5° C. for 3 h. Removal of the solvent in vacuo gave a residue which was dissolved in dichloromethane and washed with cold water (25 ml). The dichloromethane fraction was dried (Na$_2$SO$_4$), and the solvent was removed in vacuo. The purification of the residue by elution from a silica gel column using dichloromethane-methanol (96:4, v/v) as eluent yielded 12 as a viscous oil.
$^1$H-NMR (CDCl$_3$) δ: 4.40-4.65 (m, 5H, CH, OCH$_2$), 5.0 [d, J=2 Hz, 1H, C(N$_3$)=CHH'], 5.38 (s, 2H, N—CH$_2$), 6.25 [d, J=2 Hz, 1H, C(N$_3$)=CHH'], 7.40-8.08 (m, 11H, H-6, AraH), 8.185 (s, 1H, NH). Anal. (C$_{24}$H$_{21}$N$_5$O$_7$) C,H,N.

Example 21

Preparation of 1-[(2-Hydroxy-1-(hydroxymethyl) ethoxy]methyl)]-5-(1-azidovinyl)uracil (13)

A solution of 12 (350 mg, 0.71 mmol) in a saturated solution of ammonia in methanol (25 ml) was stirred at 25° C. for 48 h. Removal of solvent in vacuo yielded a residue which was purified by silica gel column chromatography using chloroform-methanol (90:10, v/v) as eluent to yield 13 (120 mg, 58.4%) as a solid; m.p. 129-130° C.
$^1$H-NMR (DMSO-d$_6$) δ: 3.30-3.50 (m, 4H, OCH$_2$), 3.55 (m, 1H, CH), 4.65 (m, 2H, OH), 5.02 [d, J=2 Hz, 1H, C(N$_3$)=CHH'], 5.25 (s, 2H, N—CH$_2$), 5.92 [d, J=2 Hz, 1H, C(N$_3$)=CHH'], 7.98-(s, 1H, H-6), 11.60 (s, 1H, NH). Anal. (C$_{10}$H$_{13}$N$_5$O$_5$) C,H,N.

Example 22

Preparation of 1-[(2-Hydroxy-1-(hydroxymethyl) ethoxy]methyl)]-5-[2-(1-azirinyl)]uracil (14)

A solution of 13 (82 mg, 0.28 mmol) in dry dioxane (45 ml) was heated at 110° C. for 3 h. Removal of the solvent in vacuo gave a viscous oil which was purified by silica gel column chromatography. Elution with chloroform-methanol (82:18, v/v) gave 14 as a dark brown oil (26 mg, 35.7%).
$^1$H-NMR (DMSO-d$_6$) δ: 1.30 (d, 2H, azirinyl hydrogens), 3.30-3.55 (m, 4H, OCH$_2$), 3.62 (m, 1H, CH), 4.70 (br, 2H, OH), 5.30 (s, 2H, N—CH$_2$), 8.45 (s, 1H, H-6). Anal. (C$_{10}$H$_{13}$N$_3$O$_5$ ½ H$_2$O)

Scheme 3

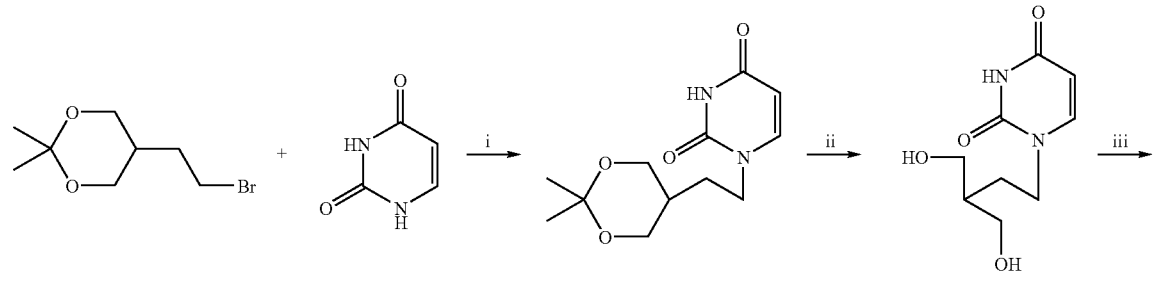

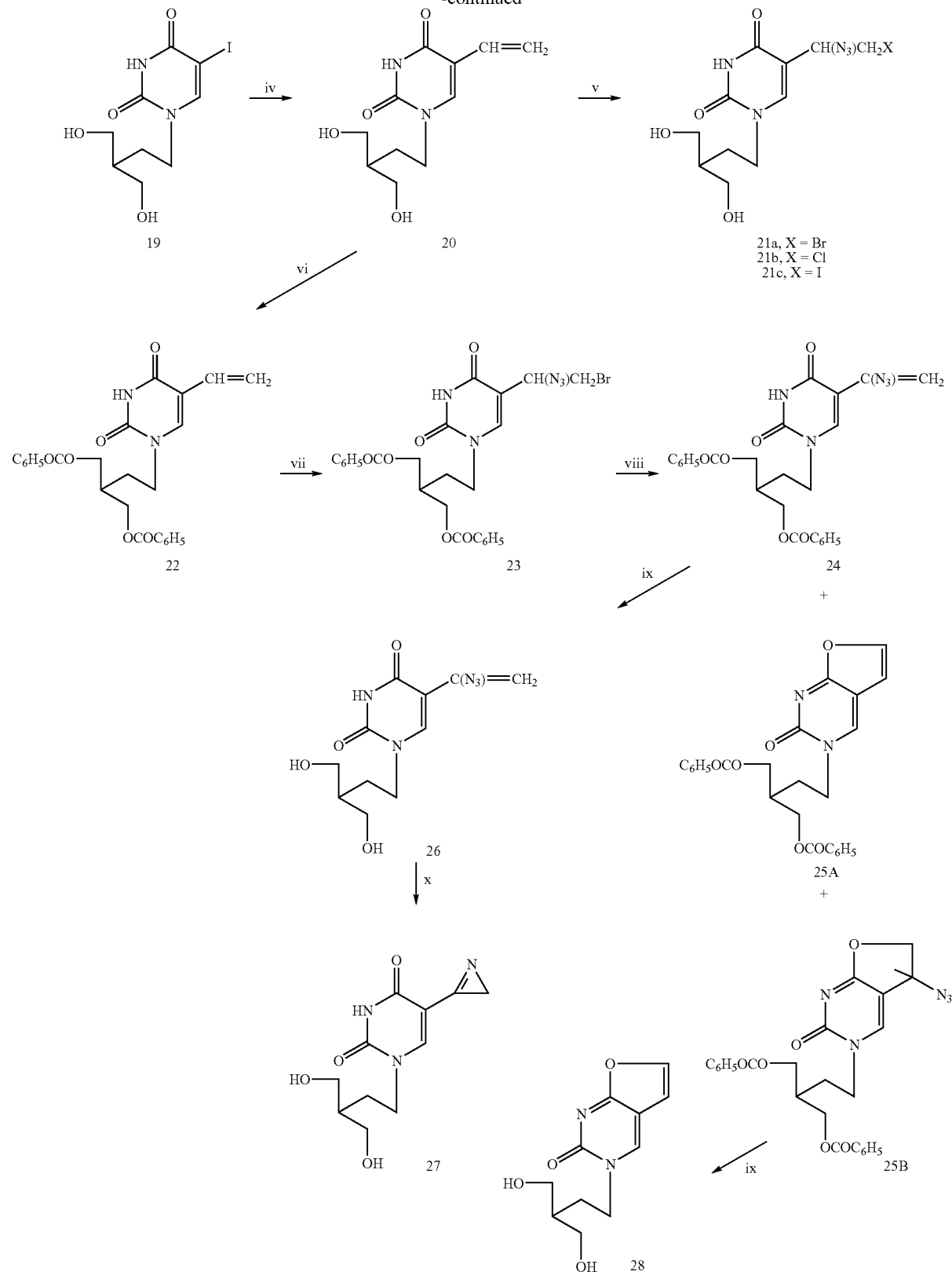
i, potassium carbonate, dry DMF, 25° C.; ii, 1M HCl, 25° C.; iii, ICl, methanol 50° C.; iv, Vinyl acetate, palladium (II) acetate, triethylamine, triphenylphosphine, 70° C., 6 h; v, NBS, sodium azide, DME, water (21a), NCS, sodium azide, DME, water, 0-25° C., (21b), ICl, sodium azide, acetonitrile (21c); vi, Benzoyl chloride, pyridine, 25° C.; vii, NBS, sodium azide, DME, water; viii, t-BuOK, dry THF, 0° C.; ix, Ammonia, methanol, 25° C.; x, Dioxane, 110° C.

Example 23

Preparation of 1-[2-(2,2-Dimethyl-1,3-dioxan-5-yl)ethyl]uracil (17)

To a solution of 5-(2-bromoethyl)-2,2-dimethyl-1,3-dioxane (15) (M. R. Hamden et al, J. Med. Chem., 30, 1636, 1987) (12.0 gm, 53.81 mmol) in dry DMF (150 ml) were added uracil (7.0 gm, 62.4 mmol) and potassium carbonate (14.0 gm). The reaction mixture was stirred at 25° C. for 5 days. The resulting solution was filtered and the solvent removed. The residue obtained was purified by column chromatography on silica gel eluting with chloroform-methanol (90:10, v/v) to afford 17 (4.0 gm, 25.2%).
$^1$H-NMR (DMSO-$d_6$) δ: 1.28 and 1.34 (2s, 3H each, $CH_3$), 1.48-1.70 (m, 3H, $CHCH_2CH_2N$), 3.55 (m, 2H, $CH_2O$), 3.68 (t, J=7.0 Hz, 2H, $CH_2N$), 3.80 (m, 2H, $CH_2O$), 5.55 (d, J=7.5 Hz, 1H, H-5), 7.70 (d, J=7.5 Hz, 1H, H-6). Anal. $C_{12}H_{18}N_2O_4$) C,H,N.

Example 24

Preparation of 1-[4-Hydroxy-3-(hydroxymethyl)-1-butyl]-uracil (18)

A solution of 17 (7.75 gm, 30.5 mmol) in 1M HCl (25 ml) was stirred at 25° C. for 30 min. The solution was neutralized by addition of 10% aq. NaOH. The resulting solution was filtered and evaporated under vacuo. The solid residue obtained was chromatographed on a silica gel column using dichloromethane-methanol (88:12, v/v) as eluent to yield 18 (2.3 gm, 35.2%), which was used in the next reaction step.

Example 25

Preparation of 1-[4-Hydroxy-3-(hydroxymethyl)-1-butyl]-5-iodouracil (19)

Iodine monochloride (500 mg, 3.08 mmol) was added to a solution of 18 (360 mg, 1.68 mmol) in dry methanol (25 ml) and the reaction mixture was stirred at 50° C. for 90 min. and then the methanol was removed in vacuo. The dry residue was treated with 5.0 ml of conc. ammonium hydroxide in 25 ml of methanol with stirring at 50° C. for 1 h. The crude reaction mixture was purified by elution from a column of silica gel by using dichloromethane-methanol (92:8, v/v) as eluent. The product 19 was obtained in 59.2% yield as a colorless gum.
$^1$H-NMR (DMSO-$d_6$) δ: 1.42-1.62 (m, 3H, $CHCH_2CH_2N$), 3.18-3.40 (m, 4H, $CH_2O$, $CH_2O$+DMSO), 3.72 (t, J=7.2 Hz, 2H, $CH_2N$), 4.45 (t, J=5.0 Hz, 2H, OH), 8.20 (s, 1H, H-6), 11.55 (br, 1H, NH). Anal. ($C_9H_{13}N_2O_4I$) C,H,N.

Example 26

Preparation of 1-[4-Hydroxy-3-(hydroxymethyl)-1-butyl]-5-vinyluracil (20)

A mixture of palladium (II) acetate (79 mg, 0.35 mmol), triphenylphosphine (185 mg, 0.7 mmol) and triethylamine (5 ml), (dried over calcium hydroxide) in dry DMF (80 ml) was maintained at 70° C. with stirring until an intense red color appeared. Compound 19 (2.36 gm, 6.95 mmol) and vinyl acetate (30 ml, 330 mmol) were then added, and the reaction was allowed to proceed at 70° C. for 6 h with stirring. The solvent was removed in vacuo and the residue obtained was extracted with water (2×50 ml). The water layer was washed with dichloromethane, evaporated in vacuo, and the residue obtained was purified by elution from a silica gel column using ethyl acetate-methanol (95:5, v/v) as eluent to give 20 as a viscous oil (800 mg, 48%).
$^1$H-NMR (DMSO-$d_6$) δ: 1.42-1.62 (m, 3H, $CHCH_2CH_2N$), 3.32-3.45 (m, 4H, $CH_2O$, $CH_2O$+DMSO), 3.72 (t, J=7.2 Hz, 2H, $CH_2N$), 4.42 (t, J=5.0 Hz, 2H, OH), 5.10 (dd, J=11 Hz, J=2.1 Hz, 1H, CH=CHH'), 5.94 (dd, J=18 Hz, J=2.1 Hz, 1H, CH=CHH'), 6.35 (dd, J=18 Hz, J=11 Hz, 1H, CH=CHH'), 7.88 (s, 1H, H-6), 11.34 (s, 1H, NH). Anal. ($C_{19}H_{16}N_2O_4$) C,H,N.

Example 27

Preparation of 1-[4-Hydroxy-3-(hydroxymethyl)-1-butyl]-5-(1-azido-2-bromoethyl)uracil (21a)

N-Bromosuccinimide (46 mg, 0.26 mmol) was added in aliquots with stirring to a precooled (−5° C.) suspension, prepared by mixing a solution of 20 (63 mg, 0.262 mmol) in 1,2-dimethoxyethane (25 ml) with a solution of sodium azide (68 mg, 1.04 mmol) in water (0.19 ml). The initial yellow color produced upon addition of each NBS aliquot quickly disappeared. After all of the NBS had been added, the reaction mixture was allowed to proceed for 30 min. at 0° C. with stirring. Removal of the solvent in vacuo gave a residue which was purified by silica gel column chromatography using chloroform:methanol (90:10, v/v) as eluent to afford 21a (66 mg, 69%) as a viscous oil.
$^1$H-NMR (DMSO-$d_6$) δ: 1.42-1.62 (m, 3H, $CHCH_2CH_2N$), 3.20-3.48 (m, 4H, $CH_2O$, $CH_2O$+DMSO), 3.75 (t, J=7.2 Hz, 2H, $CH_2N$), 3.88 (m, 2H, $CH_2Br$), 4.45 (t, J=5.0 Hz, 2H, OH), 4.70 (m, 1H, $CHN_3$), 7.85 (s, 1H, H-6), 11.55 (s, 1H, NH). Anal. ($C_{11}H_{16}N_5O_4Br$) C,H,N.

Example 28

Preparation of 1-[4-Hydroxy-3-(hydroxymethyl)-1-butyl]-5-(1-azido-2-chloroethyl)uracil (21b)

N-Chlorosuccinimide (50 mg, 0.37 mmol) was added slowly with stirring to a precooled (−5° C.) suspension, prepared by mixing a solution of 20 (75 mg, 0.31 mmol) in 1,2-dimethoxyethane (25 ml) with a solution of sodium azide (81 mg, 1.24 mmol) in water (0.23 ml). The reaction mixture was allowed to proceed for 2 h at 0° C. with stirring and the solvent was removed in vacuo. The resulting residue was purified by silica gel column chromatography using chloroform:methanol (90:10, v/v) as eluent to afford 21b (46 mg, 47%) as a viscous oil.
$^1$H-NMR (DMSO-$d_6$) δ: 1.45-1.60 (m, 3H, $CHCH_2CH_2N$), 3.30-3.46 (m, 4H, $CH_2O$, $CH_2O$+DMSO), 3.78 (t, J=7.2 Hz, 2H, $CH_2N$), 3.95 (m, 2H, $CH_2Cl$), 4.45 (t, J=5.0 Hz, 2H, OH), 4.80 (m, 1H, $CHN_3$), 7.85 (s, 1H, H-6), 11.55 (s, 1H, NH). Anal. ($C_{11}H_{16}N_5O_4Cl$) C,H,N.

Example 29

Preparation of 1-[4-Hydroxy-3-(hydroxymethyl)-1-butyl]-5-(1-azido-2-iodoethyl)uracil (21c)

Iodine monochloride (50 mg, 0.3 mmol) was added slowly with stirring during a five minute period to a suspension of sodium azide (72 mg, 1.1 mmol) in dry acetonitrile (10 ml) at ice-bath temperature with stirring. This mixture stirred for a further 5 min., a solution of 20 (66 mg, 0.275 mmol) in dry acetonitrile (40 ml) was added, the reaction mixture was maintained at 0° C. for 30 min. with stirring. The resulting red-brown colored reaction mixture was poured onto ice cold water (25 ml), the mixture was extracted with ethyl acetate (3×50 ml) and the ethyl acetate extract was washed with 5% aqueous sodium thiosulfate (30 ml). Drying the colorless ethyl acetate fraction ($Na_2SO_4$), removal of the solvent in vacuo and purification of the residue obtained by elution from a silica gel column using chloroform:methanol (90:10, v/v) as eluent afforded 21c (24 mg, 21%) as a viscous oil.

$^1$H-NMR (DMSO-$d_6$) δ: 1.45-1.65 (m, 3H, CH$CH_2CH_2$N), 3.30-3.50 (m, 4H, $CH_2$O, $CH_2$O+DMSO), 3.62 (m, 2H, $CH_2$I), 3.80 (t, J=7.2 Hz, 2H, $CH_2$N), 4.45 (t, J=5.0 Hz, 2H, OH), 4.70 (m, 1H, $CHN_3$), 7.84 (s, 1H, H-6), 11.55 (s, 1H, NH). Anal. ($C_{11}H_{16}N_5O_4$I ¼$H_2$O) C,H,N.

Example 30

Preparation of 1-[4-Benzoyloxy-3-(benzoyloxymethyl)-1-butyl]-5-vinyluracil (22)

Benzoylchloride (600 mg, 4.2 mmol) was added to a solution of 20 (450 mg, 1.87 mmol) in dry pyridine (50 ml) and the reaction was allowed to proceed at 25° C. with stirring for 48 h. The reaction mixture was poured onto ice water (50 ml) and extracted with dichloromethane (3×50 ml). The dichloromethane extract was dried over sodium sulfate, the solvent was removed in vacuo and the residue obtained was purified by elution from a silica gel column using chloroform-methanol (97:3, v/v) as eluent to yield 22 as a viscous oil (550 mg, 65.4%) which was used directly in the next reaction step.

Example 31

Preparation of 1-[4-Benzoyloxy-3-(benzoyloxymethyl)-1-butyl]-5-(1-azido-2-bromoethyl)uracil (23)

A mixture of 22 (510 mg, 1.14 mmol), saturated solution of sodium azide in water (300 mg, 4.6 mmol), N-bromosuccinimide (223 mg, 1.25 mmol) and 1,2-dimethoxyethane (50 ml) was stirred at 0° C. for 30 min. Removal of the solvent in vacuo gave a viscous oil which was purified by silica gel column chromatography. Elution with chloroform-methanol (96:4, v/v) yielded 23 (530 mg, 81.5%) as a syrup.

$^1$H-NMR (CDCl$_3$) δ: 1.92 (m, 2H, CH$CH_2CH_2$N), 2.36 (m, 1H, CH$CH_2CH_2$N), 3.52-3.80 (m, 2H, $CH_2$N), 4.0 (m, 2H, $CH_2$Br), 4.48 (m, 4H, $CH_2$O), 4.82 (m, 1H, $CHN_3$), 7.36-8.0 (m, 11H, H-6, AraH), 9.38 (s, 1H, NH). Anal. ($C_{25}H_{24}N_5O_6$Br) C,H,N.

Example 32

Preparation of 1-[4-Benzoyloxy-3-(benzoyloxymethyl)-1-butyl]-5-(1-azidovinyl)uracil (24), 5-[4-Benzoyloxy-3-(benzoyloxymethyl)-1-butyl]-[2,3-d]pyrimidin-6-(5H)-one (25A) and 3-azido-2,3-dihydro-5-[4-Benzoyloxy-3-(benzoyloxymethyl)-1-butyl]furano-[2,3-d]pyrimidin-6-(5H)-one (25B)

Reaction of potassium tert-butoxide (208 mg, 1.84 mmol) with 23 (530 mg, 0.93 mmol), using the procedure described for the preparation of 5 and purification of the product using chloroform-methanol (97:3, v/v) as eluent yielded three products which eluted in the following order:

Fraction 1 (24): (235 mg, 51.6%), m.p. 111° C. dec.;

$^1$H-NMR (CDCl$_3$) δ: 1.95 (m, 2H, CH$CH_2CH_2$N), 2.406 (m, 1H, CH$CH_2CH_2$N), 4.0 (t, J=7.2 Hz, 2H, $CH_2$N), 4.50 (m, 4H, $CH_2$O), 5.05 [d, J=2.0 Hz, 1H, $C(N_3)$=CHH'], 6.32 [d, J=2.0 Hz, 1H, $C(N_3)$=CHH'], 7.40-8.08 (m, 11H, H-6, AraH), 8.26 (s, 1H, NH). Anal. ($C_{25}H_{23}N_5O_6$) C,H,N.

Fraction 2 (25A): (63 mg, 15%). $^1$H-NMR (CDCl$_3$) δ: 2.08 (m, 2H, CH$CH_2CH_2$N), 2.38 (m, 1H, CH$CH_2CH_2$N), 4.26 (t, J=7.2 Hz, 2H, $CH_2$N), 4.48 (m, 4H, $CH_2$O), 6.50 [d, J=2.6 Hz, 1H, OCH=CH], 7.32 [d, J=2.5 Hz, 1H, OCH=CH], 7.38-8.08 (m, 11H, H-6, AraH), Anal. ($C_{25}H_{22}N_2O_6$) C,H,N.

Fraction 3 (25B): (5 mg, 1.1%), $^1$H NMR (CDCl$_3$) δ: 1.92 (m, 2H, N$CH_2CH_2$), 2.38 (m, 1H, CH), 4.26 (m, 2H, $NCH_2$), 4.40 (m, 4H, $OCH_2$), 4.62-4.80 [m, 2H, furanyl $CH_2$], 4.90 [m, 1H, furanyl $CHN_3$], 7.38-8.08 (m, 11H, H-6, benzoyl hydrogens), Anal. ($C_{25}H_{22}N_2O_6$·¼$H_2$O) C,H,N.

Example 33

Preparation of 1-[4-Hydroxy-3-(hydroxymethyl)-1-butyl]-5-(1-azidovinyl)uracil (26)

A solution of 24 (220 mg, 0.45 mmol) in a saturated solution of ammonia and methanol (30 ml) was stirred at 25° C. for 5 days. Removal of the solvent in vacuo yielded a residue that was purified by silica gel column chromatography using chloroform-methanol (92:8, v/v) as eluent to yield 26 (100 mg, 79%) as a solid; m.p., 126-127° C.

$^1$H-NMR (CD$_3$OD) δ: 1.6-1.8 (m, 3H, CH$CH_2CH_2$N), 3.6 (m, 4H, $CH_2$O, $CH_2$O), 3.90 (t, J=7.2 Hz, 2H, $CH_2$N), 5.02 (d, J=2 Hz, 1H, $C(N_3)$=CHH'), 6.10 (d, J=2 Hz, 1H, $C(N_3)$=CHH'), 7.90 (s, 1H, H-6). Anal. ($C_{11}H_{15}N_5O_4$) C,H,N.

Example 34A

Preparation of 1-[4-Hydroxy-3-(hydroxymethyl)-1-butyl]-5-[2-(1-azirinyl)]uracil (27)

A solution of 24 (26 mg, 0.09 mmol) in dry dioxane (10 ml) was stirred at 110° C. for 4 h. Removal of the solvent in vacuo gave a dark brown residue which was purified by PTLC using chloroform-methanol (80:20, v/v) as development solvent to yield 27 (6 mg, 26%) as a dark yellow oil.

$^1$H-NMR (CD$_3$OD) δ: 1.30-1.50 (m, 2H, azirinyl hydrogens), 1.65-1.85 (m, 3H, CH$CH_2CH_2$N), 3.60 (m, 4H, $CH_2$O, $CH_2$O), 4.0 (t, J=7.2 Hz, 2H, $CH_2$N), 8.42 (s, 1H, H-6). Anal. ($C_{11}H_{15}N_3O_5$½$H_2$O) C,H,N.

Example 34B

Preparation of 5-[4-hydroxy-3-(hydroxymethyl)-1-butyl]furano-[2,3-d]pyrimidin-6-(5H)-one (28)

A solution of 25b (15 mg, 0.3 mmol) in a saturated solution of ammonia in methanol (1 mL) was stirred at 25° C. for 5 days. Removal of the solvent in vacuo and purification of the residue obtained on PTLC using chloroform-methanol (90:10 v/v) as a development solvent afforded 28 (4.3 mg, 60%) as a syrup.

$^1$H NMR (CD$_3$OD) δ 1.68-1.84 (m, 3H, CH, N$CH_2CH_2$), 3.58-3.64 (m, 4H, $OCH_2$), 2.75 (t, J=7.2 Hz, 2H, $NCH_2$), 6.75 (d, J=2.5 Hz, 1H, OCH=CH), 7.58 (d, J=2.5 Hz, 1H, OCH=CH), 8.58 (s, 1H, H-6); $^{13}$C NMR (CD$_3$OD) δ 29.3 (N$CH_2CH_2$), 42.13 (CH), 51.6 (N$CH_2$), 63.5 ($OCH_2$), 105.8 (C-3), 107.9 (C-3a), 145.0 (C-4), 146.3 (C-2), 157.5 (C-6), 173.1 (C-7a). Anal. ($C_{11}H_{14}N_2O_4$), C,H,N.

Example 35

Preparation of 5-bromo-$O^6$-5'-cyclo-5,6-dihydro-3'-azido-3'-deoxythymidine (Method A)

A solution of N-bromosuccinimide (230 mg, 1.35 mmol) and trifluoroacetic acid (0.5 ml, 6.2 mmol) in dry DMF (5 ml)

was added dropwise to a solution of 3'-azido-3'-deoxythymidine (315 mg, 1.18 mmol) in dry DMF (25 ml) at 25° C. with stirring. The reaction was allowed to proceed at 25° C. for 2 h. Removal of the solvent in vacuo, adsorption of the residue onto silica gel (1.0 g), removal of the solvent in vacuo, and application of this material to the top of a silica gel column (Merck 7734, 100-200 mM particle size) followed by elution with chloroform-methanol (98:2, v/v) afforded (5S,6S)-5-bromo-$O^6$-5'-cyclo-5,6-dihydro-3'-azido-3'-deoxythymidine (R-1) and (5R,6R)-5-bromo-$O^6$-5'-cyclo-5,6-dihydro-3'-azido-3'-deoxythymidine (R-2), respectively. Analysis: ($C_{10}H_{12}N_5O_4Br$) C,H,N.

Diastereomer R-1: $[\alpha]_D 25=(-) 40.68°$ (C 0.0029, MeOH); Rf 0.81 (5% MeOH/CHCl$_3$); solid; m.p. 172-175° C. dec.; yield (110 mg, 26.2%); $^1$H NMR (CD$_3$OD) (δ) 1.98 (s, 3H, 5-CH$_3$), 2.36 (m, 1H, H-2'), 2.80 (m, 1H, H-2"), 3.88 (dd, J=12.5, 2.5 Hz, 1H, H-5'), 4.08 (d, J=12.5 Hz, 1H, H-5"), 4.22 (m, 1H, H-3'), 4.48 (m, 1H, H-4'), 5.30 (s, 1H, H-6), 6.12 (d, J=6.5 Hz, 1H, H-1').

Diastereomer R-2: $[\alpha]_D 25=(+) 83.07°$ (C 0.0026, MeOH); Rf 0.74 (5% MeOH/CHCl$_3$); solid; m.p. 170-172° C.; yield (165 mg, 40.3%); $^1$H NMR (CD$_3$OD) (δ) 1.94 (s, 3H, 5-CH$_3$), 2.42 (m, 1H, H-2'), 2.58 (m, 1H, H-2"), 3.94 (d, J=12.5 Hz, 1H, H-5'), 4.04 (dd, J=12.5, 6.0 Hz, 1H, H-5"), 4.45 (m, 1H, H-4'), 4.62 (m, 1H, H-3'), 4.92 (s, 1H, H-6), 6.52 (d, J=7.5 Hz, 1H, H-1').

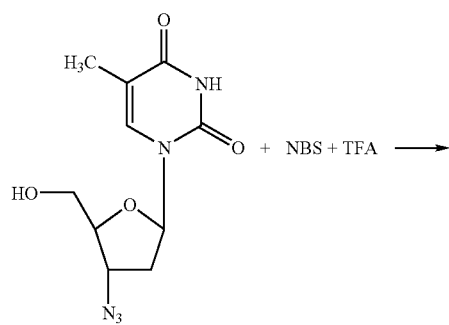

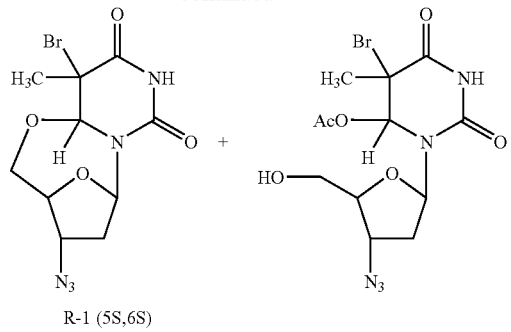

Bromine was added slowly to a precooled (−5° C.) suspension prepared by mixing a solution of 3'-azido-3'-deoxythymidine (945 mg, 3.54 mmol) in dioxane (10 ml) and a solution of sodium acetate (2.46 g, 30.0 mmol) in water (2.0 ml) with stirring until the light yellow color of the resulting solution persisted. The reaction was allowed to proceed at 0° C. for 20 min. After removal of the solvent in vacuo, the residue obtained was extracted with acetone (3×50 ml). From the acetone fraction, solvent was removed in vacuo and the residue obtained was purified by elution from a silica gel column using chloroform-methanol (97:3, v/v) as eluent to yield (5S, 6S)-5-bromo-$O^6$-5'-cyclo-5,6-dihydro-3'-azido-3'-deoxythymidine (R-1) as a solid (300 mg, 24.5%).

Rf, M.p. and $^1$H NMR spectrum were similar to that of R-1 shown in example 35.

Along with the diastereomer (5R,6R)-5-bromo-$O^6$-5'-cyclo-5,6-dihydro-3'-azido-3'-deoxythymidine (R-1), the method B provided two diastereomers of 5-bromo-6-acetoxy-5,6-dihydro-3'-azido-3'-deoxythymidine.

Example 37

Preparation of 5-iodo-$O^6$-5'-cyclo-5,6-dihydro-3'-azido-3'-deoxythymidine

Example 36

Preparation of 5-bromo-$O^6$-5'-cyclo-5,6-dihydro-3'-azido-3'-deoxythymidine (Method B)

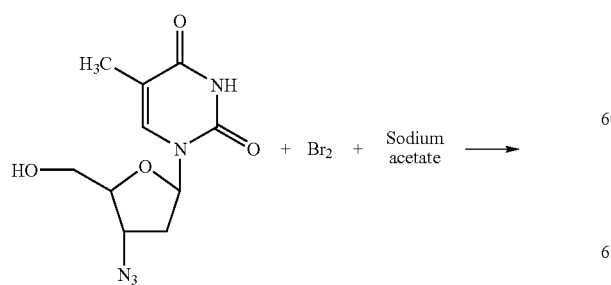

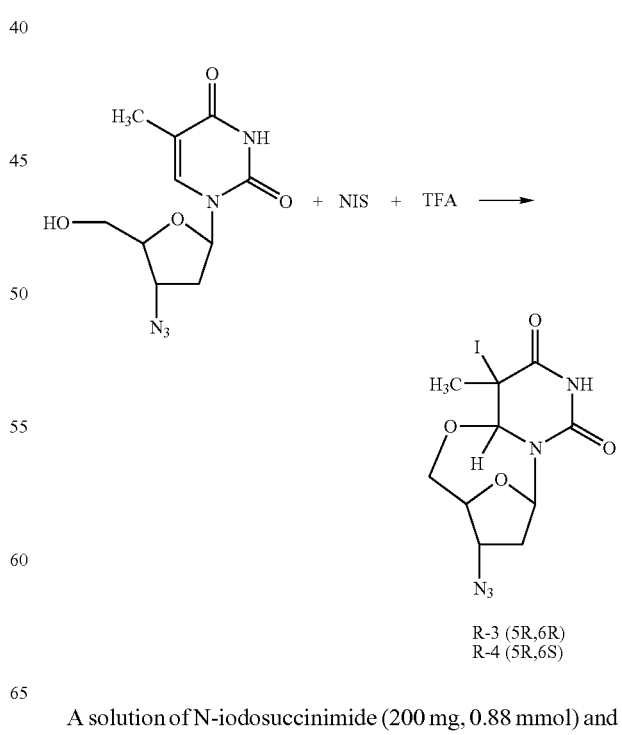

A solution of N-iodosuccinimide (200 mg, 0.88 mmol) and trifluoroacetic acid (0.32 ml, 4.0 mmol) in dry DMF (2 ml)

was added dropwise to a solution of 3'-azido-3'-deoxythymidine (210 mg, 0.78 mmol) in dry DMF (15 ml) at 25° C. with stirring. The reaction was allowed to proceed at 25° C. for 5 h. Removal of the solvent in vacuo, and purification of the residue as described in example 35 afforded (5R,6R)-5-iodo-$O^6$-5'-cyclo-5,6-dihydro-3'-azido-3'-deoxythymidine (R-3) and (5R,6S)-5-iodo-$O^6$-5'-cyclo-5,6-dihydro-3'-azido-3'-deoxythymidine (R-4), respectively. Analysis: ($C_{10}H_{12}N_5O_4I$) C,H,N.

Diastereomer R-3: $[\alpha]_D 25=(+)$ 62.0° (C 0.002, MeOH); Rf 0.73 (5% MeOH/CHCl$_3$); oil; yield (31 mg, 10%); $^1$H NMR (CD$_3$OD) (δ) 1.98 (s, 3H, 5-CH$_3$), 2.50 (m, 1H, H-2'), 2.60 (m, 1H, H-2"), 3.92 (d, J=12.5 Hz, 1H, H-5'), 4.0 (dd, J=12.5, 6.0 Hz, 1H, H-5"), 4.45 (m, 1H, H-4'), 4.65 (m, 1H, H-3'), 4.92 (s, 1H, H-6), 6.52 (d, J=7.5 Hz, 1H, H-1').

Diastereomer R-4: $[\alpha]_D 25=(-)$ 12.5° (C 0.0017, MeOH); Rf 0.67 (5% MeOH/CHCl$_3$); solid; m.p. 135-140° C. dec.; yield (75 mg, 24.3%); $^1$H NMR (CD$_3$OD) (δ) 2.0 (s, 3H, 5-CH$_3$), 2.48 (m, 1H, H-2'), 2.92 (m, 1H, H-2"), 3.70 (s, 1H, H-6), 3.92 (d, J=12.5 Hz, 1H, H-5'), 4.26-4.42 (m, 3H, H-3', H-4', H-5"), 6.65 (m, 1H, H-1').

Example 38

Additional Preparative Examples

Utilizing the general methodology (or variations thereof) described in the examples 35-37 and starting from the appropriately substituted compounds, the following compounds of the formula (IA) are prepared (Table 6).

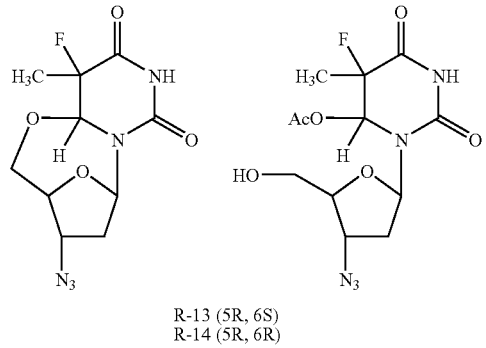

R-13 (5R, 6S)
R-14 (5R, 6R)

A solution of 3'-azido-3'-deoxythymidine (213 mg, 0.8 mmol) in acetonitrile (10 ml) containing acetic acid (1 ml) was treated with NFTH (256 mg, 0.8 mmol) and heated at 50° C. for 5 h. After removal of the solvent in vacuo, the residue was chromatographed on silica gel column using chloroform-methanol (97:3, v/v) as eluent to obtain (5R,6S) 5-fluoro-$O^6$-5'-cyclo-5,6-dihydro-3'-azido-3'-deoxythymidine (R-13) and (5R,6R) 5-fluoro-$O^6$-5'-cyclo-5,6-dihydro-3'-azido-3'-deoxythymidine (R-14), respectively. Analysis ($C_{10}H_{12}N_5O_4F$) C,H,N.

Diastereomer R-13: $[\alpha]_D 25=(-)$ 17.63° (C 0.0165, MeOH); Rf 0.63 (5% MeOH/CHCl$_3$); solid; m.p. 190-195° C. dec.; yield (80 mg, 35.0%); $^1$H NMR (CD$_3$OD) (δ) 1.56 (d, J=22.5 Hz, 3H, CH$_3$), 2.45-2.58 (m, 2H, H-2'), 3.80 (dd,

TABLE 6

5-Halo-$O^6$-5'-cyclo-5,6-dihydro diastereomers prepared according to Examples 35-37.

| Compd# | Chemical name | R$_1$ | R$_2$ | Z-Z$_1$ | R$_f^a$ | $[\alpha]_D 25$ (c,MeOH) | mp, ° C. |
|---|---|---|---|---|---|---|---|
| R-5 | (5S,6S) 5-Bromo-$O^6$-5'-cyclo-5,6-dihydro-3'-fluoro-3'-deoxythymidine | CH$_3$ | Br | CH(F)—CH$_2$ | 0.71 | (−) 30.8° (0.0025) | Oil |
| R-6 | (5R,6R) 5-Bromo-$O^6$-5'-cyclo-5,6-dihydro-3'-fluoro-3'-deoxythymidine | CH$_3$ | Br | CH(F)—CH$_2$ | 0.67 | (+) 51.42° (0.0042) | 153-54 |
| R-7 | (5S,6S)5-Bromo-$O^6$-5'-cyclo-5,6-dihydro-2',3'-dideoxythymidine | CH$_3$ | Br | CH$_2$—CH$_2$ | 0.8 | ND | Oil |
| R-8 | (5R,6R)5-Bromo-$O^6$-5'-cyclo-5,6-dihydro-2',3'-dideoxythymidine | CH$_3$ | Br | CH$_2$—CH$_2$ | 0.7 | (+) 70.52° (0.0038) | 180-82 dec. |
| R-9 | (5S,6S) 5-Bromo-$O^6$-5'-cyclo-5,6-dihydro-5-ethyl-2'-deoxyuridine | C$_2$H$_5$ | Br | CH(OH)CH$_2$ | 0.23 | (−) 30-.25° (0.004) | Oil |
| R-10 | (5S,6S) 5-Bromo-$O^6$-5'-cyclo-5,6-dihydro-5-ethyl-2'-arabinofluoro-2'-deoxyuridine | C$_2$H$_5$ | Br | CH(OH)CH(F) | 0.28 | (−) 55.38° (0.0039) | 175-76 |
| R-11 | (5S,6S)5-Bromo-$O^6$-5'-cyclo-5,6-dihydro-2'-deoxythymidine | CH$_3$ | Br | CH(OH)CH$_2$ | 0.24 | (−) 26.6° (0.00075) | 124-25 dec. |
| R-12 | (5R,6R)5-Bromo-$O^6$-5'-cyclo-5,6-dihydro-2'-deoxythymidine | CH$_3$ | Br | CH(OH)CH$_2$ | 0.21 | ND | Oil |

$^a$CHCl$_3$-MeOH (95:5, v/v), Macherey-Nagel 0.25 mm silica gel thin layer plates;
ND = Not determined;
dec. = decomposed.

Example 39

Preparation of 5-fluoro-$O^6$-5'-cyclo-5,6-dihydro-3'-azido-3'-deoxythymidine

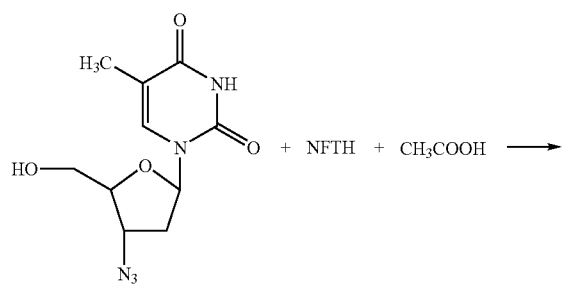

J=12.5, 2.2 Hz, 1H, H-5'), 4.28 (m, 2H, H-3', H-5"), 4.40 (d, J=2.1 Hz, 1H, H-4'), 5.10 (d, J$_{5F,6H}$=18.0 Hz, 1H, H-6), 6.52 (dd, J=7.5, 3.0 Hz, 1H, H-1').

Diastereomer R-14: $[\alpha]_D 25=(+)$ 49.14° (C 0.0035, CH$_2$Cl$_2$); Rf 0.55 (5% MeOH/CHCl$_3$); solid; m.p. 125-130° C. sublimed.; yield (40 mg, 17.5%); $^1$H NMR (CD$_3$OD) (δ) 1.60 (d, J=21.8 Hz, 3H, CH$_3$), 2.38 (m, 1H, H-2'), 2.58 (m, 1H, H-2"), 3.96 (dd, J=12.5, 1.0 Hz, 1H, H-5'), 4.10 (dd, J=12.5, 5.5 Hz, 1H, H-5"), 4.42 (d, J=5.5 Hz, 1H, H-4'), 4.50 (m, 1H, H-3'), 4.95 (d, J$_{5F,6H}$=5.8 Hz, 1H, H-6), 6.52 (d, J=7.8 Hz, 1H, H-1').

Along with the two diastereomers (5R,6S)-5-fluoro-$O^6$-5'-cyclo-5,6-dihydro-3'-azido-3'-deoxythymidine (R-13) and (5R,6R)-5-fluoro-$O^6$-5'-cyclo-5,6-dihydro-3'-azido-3'-deoxythymidine (R-14), this method provided three diastereomers of 5-fluoro-6-acetoxy-5,6-dihydro-3'-azido-3'-deoxythymidine.

Example 40

Preparation of 5-fluoro-$O^6$-5'-cyclo-5,6-dihydro-3'-fluoro-3'-deoxythymidine

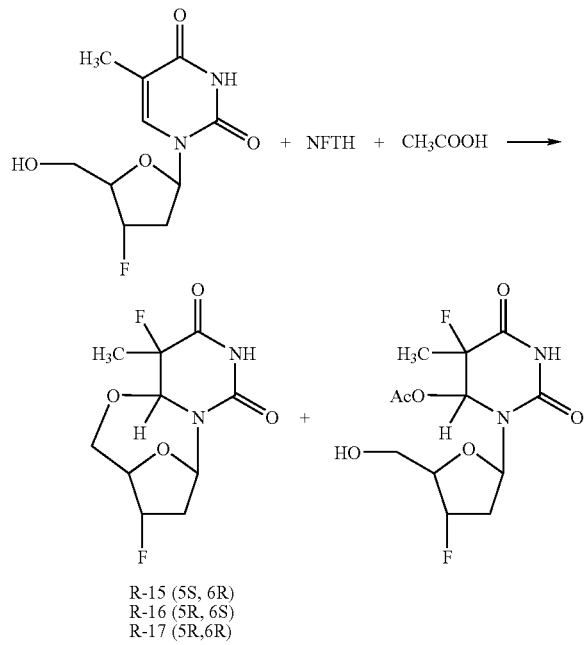

R-15 (5S, 6R)
R-16 (5R, 6S)
R-17 (5R,6R)

In contrast to the previous example 38, similar reaction with 3'-fluoro-3'-deoxythymidine, provided three cyclic diastereomers. NFTH (225 mg, 0.71 mmol) was added to a solution of 3'-fluoro-3'-deoxythymidine (175 mg, 0.71 mmol) in acetonitrile (10 ml) and glacial acetic acid (1 ml) with stirring and the reaction was allowed to proceed at 50° C. for 6 h. Removal of the solvent in vacuo gave a residue which was purified by elution from a silica gel column using chloroform-methanol (98:2, v/v) as eluent to yield (5S,6R)-5-fluoro-$O^6$-5'-cyclo-5,6-dihydro-3'-fluoro-3'-deoxythymidine (R-15), (5R,6S)-5-fluoro-$O^6$-5'-cyclo-5,6-dihydro-3'-fluoro-3'-deoxythymidine (R-16) and (5R,6R)-5-fluoro-$O^6$-5'-cyclo-5,6-dihydro-3'-fluoro-3'-deoxythymidine (R-17), respectively. Analysis ($C_{10}H_{12}N_2O_4F_2$) C,H,N.

Diastereomer R-15: $[\alpha]_D 25 = (+) 28.4°$ (C 0.0045, MeOH); Rf 0.73 (5% MeOH/CHCl$_3$); oil; yield (10.0 mg, 5.3%); $^1$H NMR (CD$_3$OD) ($\delta$) 1.52 (d, J=22.5 Hz, 3H, CH$_3$), 2.32-2.70 (m, 2H, H-2'), 3.82 (m, 1H, H-5'), 4.30 (d, J=12.8 Hz, 1H, H-5"), 4.52 (dd, J=20.0, 2.2 Hz, 1H, H-4'), 5.22 (d, $J_{5F,6H}$=10.0 Hz, 1H, H-6), 5.35 (ddd, J=55.0, 5.5, 0.5 Hz, 1H, H-3'), 6.62 (dt, J=1.8, 4.8, 8.0 Hz, 1H, H-1').

Diastereomer R-16: $[\alpha]_D 25 = (-) 28.26°$ (C 0.0093, MeOH); Rf 0.65 (5% MeOH/CHCl$_3$); oil; yield (75.0 mg, 40.3%); $^1$H NMR (CD$_3$OD) ($\delta$) 1.54 (d, J=22.5 Hz, 3H, CH$_3$), 2.38-2.68 (m, 2H, H-2'), 3.80 (m, 1H, H-5'), 4.30 (d, J=12.8 Hz, 1H, H-5"), 4.53 (dd, J=20.0, 2.2 Hz, 1H, H-4'), 5.08 (d, $J_{5F,6H}$=18.5 Hz, 1H, H-6), 5.36 (ddd, J=54.5, 5.5, 1.0 Hz, 1H, H-3'), 6.60 (dd, J=3.5, 7.5 Hz, 1H, H-1').

Diastereomer R-17: $[\alpha]_D 25 = (+) 27.38°$ (C 0.0084, MeOH); Rf 0.53 (5% MeOH/CHCl$_3$); oil; yield (45.0 mg, 24%); $^1$H NMR (CD$_3$OD) ($\delta$) 1.62 (d, J=22.0 Hz, 3H, CH3), 2.42-2.65 (m, 2H, H-2'), 3.96 (d, J=12.5 Hz, 1H, H-5'), 4.10 (dd, J=12.5, 6.2 Hz, 1H, H-5"), 4.54 (dd, J=25.0, 6.2 Hz, 1H, H-4'), 4.72 (d, $J_{5F,6H}$=4.5 Hz, 1H, H-6), 5.58 (ddd, J=55.2, 6.6, 2.0 Hz, 1H, H-3'), 6.55 (d, J=7.5 Hz, 1H, H-1').

Along with the three diastereomers (5S,6R)-5-fluoro-$O^6$-5'-cyclo-5,6-dihydro-3'-fluoro-3'-deoxythymidine (R-15), (5R,6S)-5-fluoro-$O^6$-5'-cyclo-5,6-dihydro-3'-fluoro-3'-deoxythymidine (R-16) and (5R,6R)-5-fluoro-$O^6$-5'-cyclo-5,6-dihydro-3'-fluoro-3'-deoxythymidine (R-17), this method provided two diastereomers of 5-fluoro-6-acetoxy-5,6-dihydro-3'-azido-3'-deoxythymidine.

Example 41

Utilizing the General Methodology (or Variations Thereof) Described in the Examples 39 and 40 and Starting from the Appropriately Substituted Compounds, the Following Compounds of the Formula (IA) are Prepared (Table 7)

TABLE 7

5-Fluoro-$O^6$-5'-cyclo-5,6-dihydro diastereomers prepared according to Examples 39 & 40.

| Compd# | Chemical name | $R_1$ | $R_2$ | $Z-Z_1$ | $R_f^a$ | $[\alpha]_D 25$ (c,MeOH) | mp, °C. |
|---|---|---|---|---|---|---|---|
| R-18 | (5S,6R) 5-fluoro-$O^6$-5'-cyclo-5,6-dihydro-2',3'-dideoxythymidine | CH$_3$ | F | CH$_2$—CH$_2$ | 0.73 | ND | Oil |
| R-19 | (5R,6S) 5-fluoro-$O^6$-5'-cyclo-5,6-dihydro-2',3'-dideoxythymidine | CH$_3$ | F | CH$_2$—CH$_2$ | 0.67 | (−) 21.25° (0.004) | 162-65 sublimed |
| R-20 | (5R,6S) 5-fluoro-$O^6$-5'-cyclo-5,6-dihydro-2',3'-dideoxythymidine | CH$_3$ | F | CH$_2$—CH$_2$ | 0.62 | (+) 37.33° (0.003) | Oil |
| R-21 | (5R,6S) 5-fluoro-$O^6$-5'-cyclo-5,6-dihydro-5-ethyl-2'-deoxyuridine | C$_2$H$_5$ | F | CH(OH)CH$_2$ | 0.20 | (−) 24.72° (0.011) | 237-39 |
| R-22 | (5R,6R) 5-fluoro-$O^6$-5'-cyclo-5,6-dihydro-5-ethyl-2'-deoxyuridine | C$_2$H$_5$ | F | CH(OH)CH$_2$ | 0.18 | (+) 22.05° (0.0078) | Oil |
| R-23 | (5S,6R) 5-fluoro-$O^6$-5'-cyclo-5,6-dihydro-2'-deoxythymidine | CH$_3$ | F | CH(OH)CH$_2$ | 0.23 | (+) 51.1° (0.0097) | Oil |
| R-24 | (5R,6S) 5-fluoro-$O^6$-5'-cyclo-5,6-dihydro-2'-deoxythymidine | CH$_3$ | F | CH(OH)CH$_2$ | 0.20 | (−) 36.08° (0.025) | 220-22 |
| R-25 | (5R,6R) 5-fluoro-$O^6$-5'-cyclo-5,6-dihydro-2'-deoxythymidine | CH$_3$ | F | CH(OH)CH$_2$ | 0.13 | (+) 38.86° (0.015) | 228-30 |

$^a$CHCl$_3$-MeOH (95:5, v/v), Macherey-Nagel 0.25 mm silica gel thin layer plates;
ND = Not determined;
dec. = decomposed.

Example 42

Preparation of 5-fluoro-O$^6$-5'-cyclo-5,6-dihydro-3'-fluoro-2',3'-dideoxyuridine

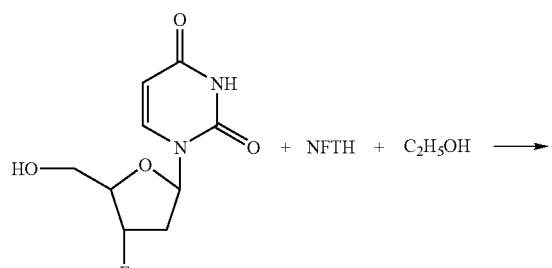

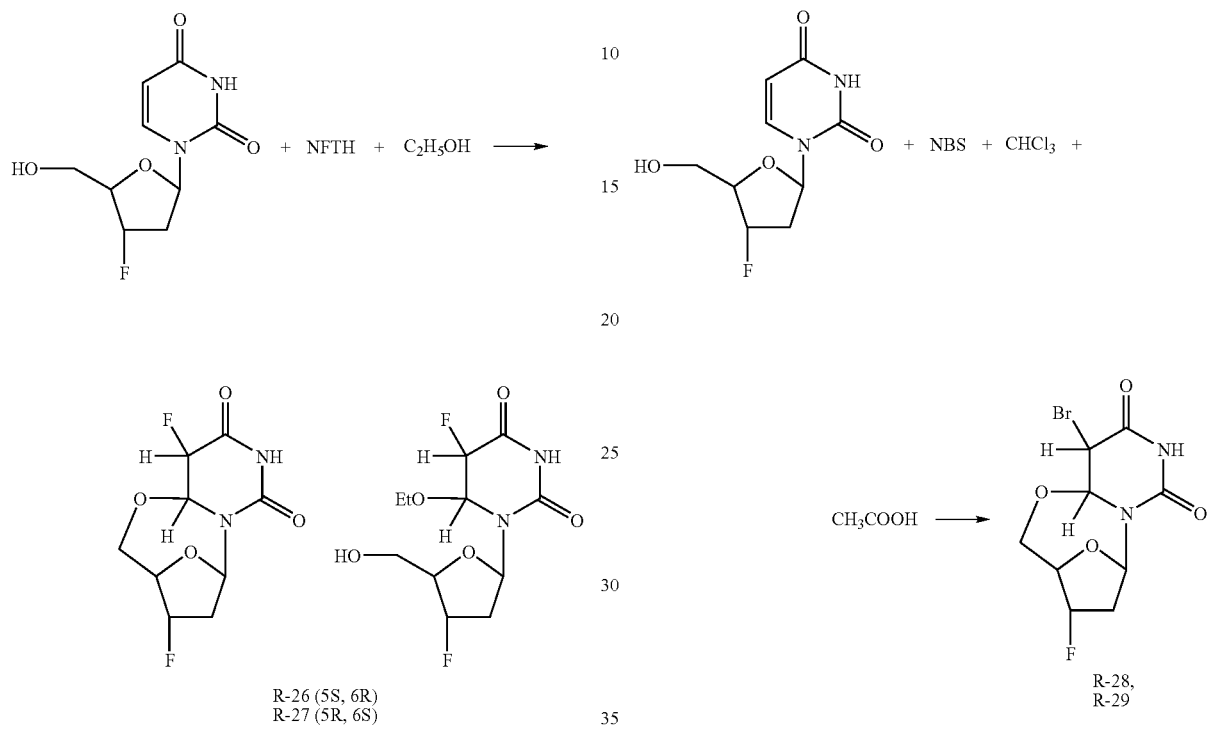

R-26 (5S, 6R)
R-27 (5R, 6S)

To a suspension of 3'-fluoro-2',3'-dideoxyuridine (250 mg, 1.08 mmol) in acetonitrile (25 ml) was added NFTH (400 mg, 1.25 mmol) and ethanol (10 ml). The reaction was allowed to proceed at 75° C. for 24 h with stirring. After removal of solvent the residue obtained was purified by silica gel column chromatography using chloroform-methanol (96:4, v/v) as eluent to afford a mixture of 5-fluoro-O$^6$-5'-cyclo-5,6-dihydro-3'-fluoro-2',3'-dideoxyuridine (R-26, R-27) and 5-fluoro-6-ethoxy-5,6-dihydro-3'-fluoro-2',3'-dideoxyuridine which was separated using Whatman PLK5F silica gel plates (1 mm thickness) using chloroform-methanol (95:5, v/v) as development solvent.

Diastereomer R-26: Rf 0.50 (5% MeOH/CHCl$_3$); oil; yield (40 mg, 15.0%); $^1$H NMR (CD$_3$OD) (δ) 2.50-2.65 (m, 2H, H-2'), 3.82 (m, 1H, H-5"), 4.28 (d, J=12.5 Hz, 1H, H-5'), 4.55 (m, 1H, H-4'), 5.18-5.46 (complex, 3H, H-5, H-6, H-3'), 6.54 (m, 1H, H-1').

Diastereomer R-27: Rf 0.47 (5% MeOH/CHCl$_3$); oil; yield (11.0 mg, 4.0%); $^1$H NMR (CD$_3$OD) (δ) 2.48-2.68 (m, 2H, H-2'), 3.82 (m, 1H, H-5"), 4.18 (d, J=12.5 Hz, 1H, H-5'), 4.62 (m, 1H, H-4'), 5.18-5.42 (complex, 3H, H-5, H-6, H-3'), 6.32 (m, 1H, H-1').

Along with the diastereomers (5S,6R)-5-fluoro-O$^6$-5'-cyclo-5,6-dihydro-3'-fluoro-2',3'-dideoxyuridine (R-26) and (5R,6S)-5-fluoro-O$^6$-5'-cyclo-5,6-dihydro-3'-fluoro-2',3'-dideoxyuridine (R-27), this method provided mixture of four diastereomers of 5-fluoro-6-ethoxy-5,6-dihydro-3'-fluoro-2',3'-dideoxyuridine.

Example 43

Preparation of 5-bromo-O$^6$-5'-cyclo-5,6-dihydro-3'-fluoro-2',3'-dideoxyuridine N-Bromosuccinimide (80 mg, 0.45 mmol) was added to a suspension of 3'-fluoro-2',3'-dideoxyuridine (100 mg, 0.43 mmol) and acetic acid (1.0 ml) in chloroform (25 ml) and the reaction mixture was stirred for 15 h at 25° C. Removal of solvent in vacuo and separation of the residue obtained by PTLC using chloroform-methanol (97:3, v/v) as development solvent gave two diastereomers 5-bromo-O$^6$-5'-cyclo-5,6-dihydro-3'-fluoro-2',3'-dideoxyuridine (R-28) and 5-bromo-O$^6$-5'-cyclo-5,6-dihydro-3'-fluoro-2',3'-dideoxyuridine (R-29), respectively. Analysis (C$_9$H$_{10}$N$_2$O$_4$BrF) C,H,N.

Example 44

Preparation of 5,5-dibromo-O$^6$-5'-cyclo-5,6-dihydro-3'-fluoro-2',3'-dideoxyuridine

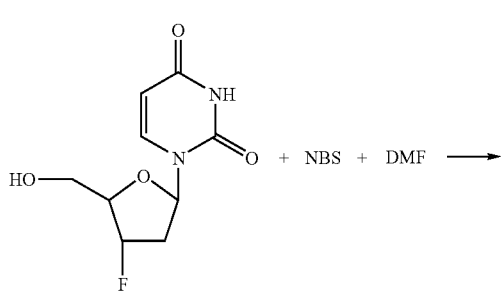

-continued

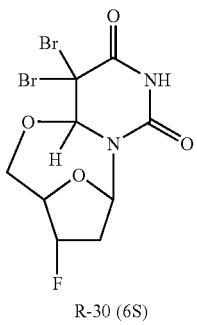

R-30 (6S)

A mixture of 3'-fluoro-2',3'-dideoxyuridine (100 mg, 0.43 mmol) and N-bromosuccinimide (216 mg, 1.21 mmol) in dry DMF (20 ml) was stirred at 25° C. for 1 h. After removal of the solvent in vacuo, the residue obtained was purified on a silica gel column using chloroform-methanol (98:2, v/v) as eluent to yield (6S)-5,5-dibromo-$O^6$-5'-cyclo-5,6-dihydro-3'-fluoro-2',3'-dideoxyuridine (R-30). Analysis ($C_9H_9N_2O_4Br_2F$) C,H,N.

Diastereomer R-30: $[\alpha]_D25=(-)$ 21.81° (C 0.0011, MeOH); Rf 0.71 (5% $MeOH/CHCl_3$); oil; yield (25.0 mg, 15.6%); $^1H$ NMR (DMSO-d6) (δ) 2.60 (m, 2H, H-2'), 3.82 (ddd, J=12.8, 2.5 Hz, 1H, H-5') 4.44 (d, J=12.8 Hz, 1H, H-5"), 4.58 (dd, J=19.8, 1.5 Hz, 1H, H-4'), 5.38 (s, 1H, H-6), 5.50 (ddd, J=54.5, 5.5, 1.0 Hz, 1H, H-3'), 6.58 (dd, J=7.5, 3.5 Hz, 1H, H-1').

Example 45

Preparation of 5,5-dichloro-$O^6$-5'-cyclo-5,6-dihydro-3'-fluoro-2',3'-dideoxyuridine

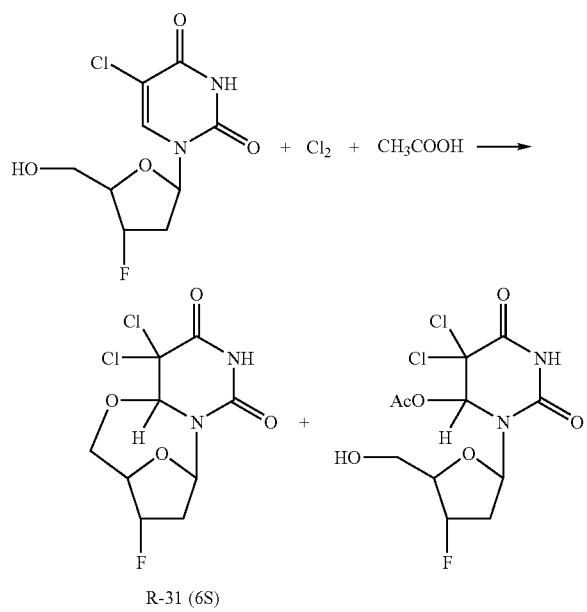

R-31 (6S)

Chlorine gas was bubbled slowly into a suspension of 5-chloro-3'-fluoro-2',3'-dideoxyuridine (75 mg, 0.28 mmol) in glacial acetic acid (5 ml) at 25° C. with stirring until the light yellow-green color of the resulting solution persisted. The reaction was allowed to proceed for 30 min. at 25° C., prior to evaporation. Purification of the residue obtained by PTLC using ethylacetate:hexanes (3:7, v/v) as development solvent afforded diastereomer (6S)-5,5-dichloro-$O^6$-5'-cyclo-5,6-dihydro-3'-fluoro-2',3'-dideoxyuridine (R-31) and one diastereomer of 5,5-dichloro-6-acetoxy-5,6-dihydro-3'-fluoro-2',3'-dideoxyuridine.

Diastereomer R-31: $[\alpha]_D25=(-)$ 26.66° (C 0.017, MeOH); Rf 0.58 (5% $MeOH/CHCl_3$); solid; m.p. 180-185° C. dec.; yield (25.0 mg, 30%); Analysis ($C_9H_9N_2O_4Cl_2F$) C,H,N; $^1H$ NMR ($CD_3OD$) (δ) 2.55 and 2.68 (2m, 2H, H-2'), 3.90 (ddd, J=12.8 Hz, 1H, H-5'), 4.40 (d, J=12.8 Hz, 1H, H-5"), 4.54 (dd, J=19.5, 2.2 Hz, 1H, H-4'), 5.38 (m, 2H, H-3', H-6), 6.65 (m, 1H, H-1').

Example 46

Preparation of 5-chloro-6-ethoxy-5,6-dihydro-3'-fluoro-2',3'-dideoxyuridine

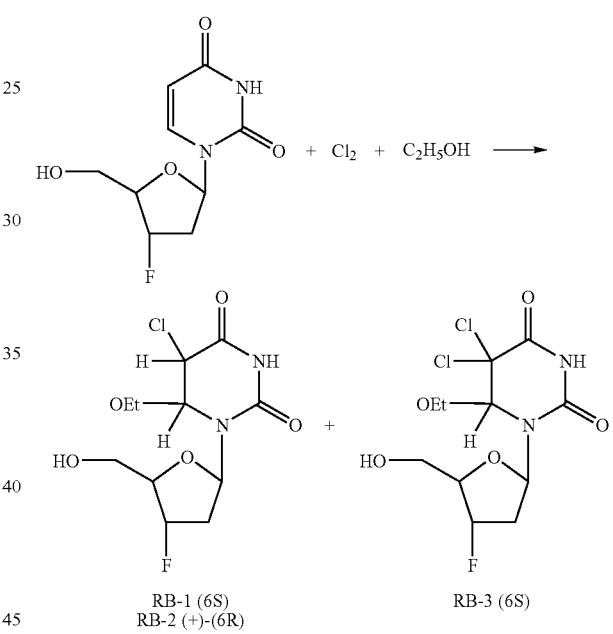

RB-1 (6S)
RB-2 (+)-(6R)

RB-3 (6S)

Chlorine gas was bubbled slowly into a suspension of 3'-fluoro-2',3'-dideoxyuridine (1.0 g, 4.34 mmol) in 98% ethanol (50 ml) at 0° C. with stirring until the light yellow-green color of the resulting solution persisted. The pH of this solution was adjusted to 6.5 using a solution of sodium hydroxide and ethanol and the mixture was filtered. Removal of the solvent from the filtrate in vacuo and separation of the residue obtained by elution from a silica gel column using chloroform:methanol (97:3, v/v) as eluent gave a mixture of (6S)-5-chloro-6-ethoxy-5,6-dihydro-3'-fluoro-2',3'-dideoxyuridine (RB-1) and (6S) 5,5-dichloro-6-ethoxy-5,6-dihydro-3'-fluoro-2',3'-dideoxyuridine (RB-3) in a ratio of 0.6:1, diastereomer [(+)-(6R)] 5-chloro-6-ethoxy-5,6-dihydro-3'-fluoro-2',3'-dideoxyuridine (RB-2) and 5-chloro-3'-fluoro-2',3'-dideoxyuridine.

RB-1 and RB-3: (mixture of two compounds in a ratio of 0.6:1 as determined by the integrals for the respective H-1' protons) Rf 0.44 (5% $MeOH/CHCl_3$); oil; $^1H$ NMR ($CD_3OD$) (δ) (RB-1) 1.2 (t, 3H, $OCH_2CH_3$), 2.26-2.48 (m, 2H, H-2'), 3.64-3.86 (m, 4H, $OCH_2CH_3$, H-5'), 4.15 (m, 1H, H-4'), 4.5

(d, J=2.2 Hz, 1H, H-5), 5.22 (m, 1H, H-3'), 5.32 (d, J 2.2 Hz, 1H, H-6), 6.08 (dd, J=6.3, 9.0 Hz, 1H, H-1').

(RB-3) 1.2 (t, 3H, OCH$_2$CH$_3$), 2.26-2.48 (m, 2H, H-2'), 3.64-3.86 (m, 4H, OCH$_2$CH$_3$, H-5'), 4.24 (m, 1H, H-4'), 5.55 (s, 1H, H-6), 6.2 (dd, J=6.2, 8.8 Hz, 1H, H-1').

Diastereomer RB-2: [α]$_D$25=(+) 52.0° (C 0.0122, MeOH); Rf 0.38 (5% MeOH/CHCl$_3$); oil; yield (200 mg, 15.0%); Analysis (C$_{11}$H$_{16}$N$_2$O$_5$ClF) C,H,N; $^1$H NMR (CD$_3$OD) (δ) 1.15 (t, 3H, OCH$_2$CH$_3$), 2.14-2.42 (m, 2H, H-2'), 3.60-3.90 (m, 4H, OCH$_2$CH$_3$, H-5'), 4.22 (m, 1H, H-4'), 4.40 (d, J=2.5 Hz, 1H, H-5), 5.20 (m, 1H, H-3'), 5.30 (d, J 2.5 Hz, 1H, H-6), 6.0 (m, 1H, H-1').

Example 47

Preparation of 5-bromo-6-ethoxy-5,6-dihydro-3'-fluoro-2',3'-dideoxyuridine

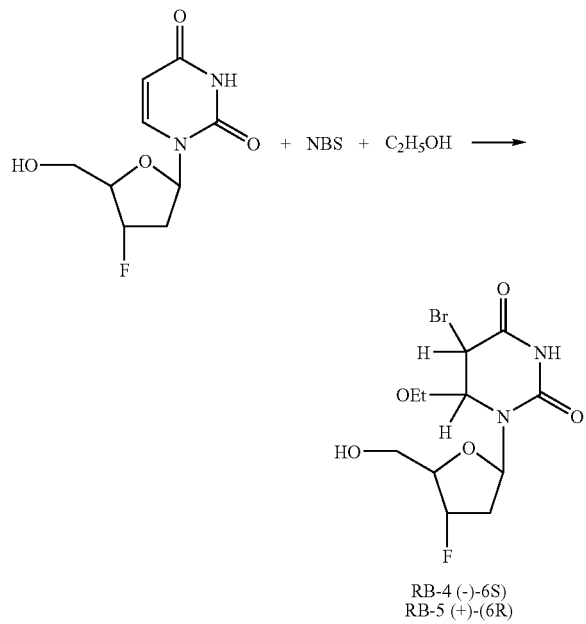

RB-4 (-)-6S)
RB-5 (+)-(6R)

N-Bromosuccinimide (80 mg, 0.44 mmol) was added in aliquots to a suspension of 3'-fluoro-2',3'-dideoxyuridine (100 mg, 0.43 mmol) in ethanol (10 ml) at 25° C. with stirring. The initial yellow color produced upon addition of each aliquot of NBS disappeared readily. After all of the NBS had been added, the reaction mixture was stirred at 25° C. for 6 h. Removal of the solvent in vacuo gave a residue which was separated by silica gel column chromatography using chloroform-methanol (96:4, v/v) as eluent to give a mixture of diastereomers [(−)-(6S)]-5-bromo-6-ethoxy-5,6-dihydro-3'-fluoro-2',3'-dideoxyuridine (RB-4) and [(+)-(6R)]-5-bromo-6-ethoxy-5,6-dihydro-3'-fluoro-2',3'-dideoxyuridine (RB-5), respectively. The two diastereomers RB-4 and RB-5 were separated using Whatman PLK5F silica gel plates (1 mm thickness) using ethylacetate:hexane (50:50, v/v) as development solvent.

Diastereomer RB-4: [α]$_D$25=(−) 40.83° (C 0.006, MeOH); Rf 0.52 (5% MeOH/CHCl$_3$); oil; yield (11 mg, 7.0%); $^1$H NMR (CD$_3$OD) (δ) 1.20 (t, 3H, OCH$_2$CH$_3$), 2.28-2.52 (m, 2H, H-2'), 3.62-3.78 (m, 4H, OCH$_2$CH$_3$, H-5'), 4.18 (m, 1H, H-4'), 4.54 (d, J=2.3 Hz, 1H, H-5), 5.20 (m, 1H, H-3'), 5.32 (d, J 2.5 Hz, 1H, H-6), 6.08 (dd, J=6.2, 9.2 Hz, 1H, H-1').

Diastereomer RB-5: [α]$_D$25=(+) 53.68° (C 0.0095, MeOH); Rf 0.45 (5% MeOH/CHCl$_3$); oil; yield (43 mg, 28.2%); $^1$H NMR (CD$_3$OD) (δ) 1.18 (t, 3H, OCH$_2$CH$_3$), 2.22-2.42 (m, 2H, H-2'), 3.62-3.88 (m, 4H, OCH$_2$CH$_3$, H-5'), 4.20 (m, 1H, H-4'), 4.48 (d, J=2.5 Hz, 1H, H-5), 5.20 (m, 1H, H-3'), 5.30 (d, J 2.5 Hz, 1H, H-6), 6.16 (dd, J=7.5, 8.0 Hz, 1H, H-1').

Example 48

Preparation of 5-fluoro-6-methoxy-5,6-dihydro-3'-fluoro-2',3'-dideoxyuridine

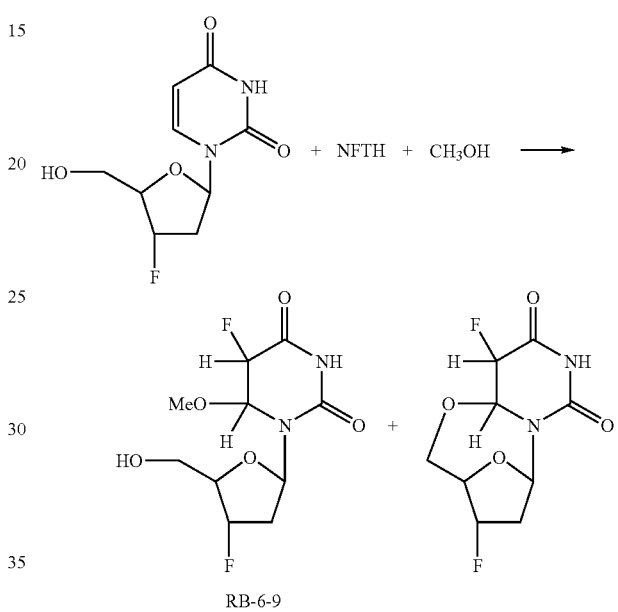

RB-6-9

To a suspension of 3'-fluoro-2',3'-dideoxyuridine (100 mg, 0.43 mmol) in acetonitrile (10 ml) was added NFTH (138 mg, 0.43 mmol) in methanol (1 ml). The reaction was allowed to proceed at 70° C. for 8 h with stirring. After removal of the solvent in vacuo, the residue was chromatographed on silica gel column using chloroform-methanol (94:6, v/v) as eluent to afford a mixture of four diastereomers of 5-fluoro-6-methoxy-5,6-dihydro-3'-fluoro-2',3'-dideoxyuridine (RB-6 to 9).

Along with the diastereomers of 5-fluoro-6-methoxy-5,6-dihydro-3'-fluoro-2',3'-dideoxyuridine (RB-6 to RB-9), this method provided mixture of two diastereomers of 5-fluoro-O$^6$-5'-cyclo-5,6-dihydro-3'-fluoro-2',3'-dideoxyuridine.

What is claimed is:

1. A compound of formula

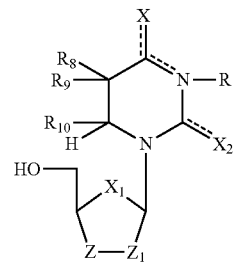

wherein:

X is =O, =S, N=CH—N(CH$_3$)$_2$, hydroxyl, alkoxy, thiol, acyloxy, substituted amino, aminoacyl, or aminoacyloxy;

85

$X_1$ is O or S;

$X_2$ is =O, =S, hydroxyl, thiol, alkoxy, amino or substituted amino;

R is H, alkyl, substituted alkyl, acyl, acylamino, or alkyl-carboxy, with the proviso that R is not present when X is hydroxyl, thiol, alkoxy, or substituted amino;

$R_8$ is H, halogen or hydroxy;

$R_9$ is H or halogen;

$R_{10}$ is halogen, hydroxy, $C_1$-$C_{18}$ alkoxy, acyloxy, or azido; and

Z—$Z_1$ is selected from the groups consisting of $CR_4R_5$—$CR_6R_7$ (wherein $R_4$, $R_5$, $R_6$, and $R_7$ are independently selected from H, OH, halogens, cyano, $N_3$, $CH_2OH$, COOH, $C_1$-$C_4$ alkyl substituted carboxy, $NH_2$, $CH_2NH_2$, $CH_2COOH$, $C_1$-$C_3$ thioalkyl, thiol, $ONO_2$, $ONH_2$, $CF_3$, $NO_2$, CNS, NHCN, $CH_2N_3$, NH—($C_1$-$C_4$ alkyl), CHO, C=CH, $C_1$-$C_4$ alkoxy, or $OCH_2$aryl), CH=CH, S—$CH_2$, O—$CH_2$, or $C(R^{27})=C(R^{28})$ (wherein $R^{27}$ and $R^{28}$ are, independently of each other, selected from H, OH, halogen, or azido), and derivatives thereof wherein —OH and/or —$NH_2$ groups are protected with phosphoesters; provided that when:

R, $R_4$ and $R_6$ are H; $R_7$ is H or OH, $R_8$ is H or halogen, $R_9$ is F, $R_{10}$ is OH, O-Alkyl, O-Acyl, or I, X, $X_1$, and $X_2$ are O, then $R_5$ is different from OH; and R, $R_4$, $R_6$, $R_7$ and $R_8$ are H; $R_9$ is Br, I, F or H; $R_{10}$ is OH; X is O or $NH_2$; $X_1$ and $X_2$ are O; then $R_5$ is different from OH; and R, $R_4$, $R_6$, $R_7$ and $R_8$ are H; $R_9$ is I; $R_{10}$ is OEt; X, $X_1$ and $X_2$ are O then $R_5$ is different from OH: and R, $R_4$, $R_6$, $R_7$ and $R_8$, are H; $R_9$ is Br or I; $R_{10}$ is $N_3$ or OMe; X, $X_1$, and $X_2$ are O then $R_5$ is different from OH or OAc; and R, $R_4$, $R_6$, $R_7$ and $R_8$, are H; $R_9$ is OH; $R_{10}$ is OH or OMe; X is O or NH; $X_1$ and $X_2$ are O then $R_5$ is different from OH or OAc; and R, $R_4$, $R_6$, $R_7$, and $R_8$ are H; $R_9$ is F; $R_{10}$ is F, or OAc; X, $X_1$, and $X_2$ are O then $R_5$ is different from COOEt; and R, $R_4$, $R_6$, and $R_8$ are H; $R_7$ is OH; $R_9$ is halogen, SH or OH; $R_{10}$ is OH, H, $C_1$-$C_6$ alkoxy or $C_1$-$C_6$ O-alkanoyl; X is O; $X_1$ and $X_2$ are O then $R_5$ is different from OH and OAc; and R, $R_4$, $R_6$, and $R_8$ are H; $R_7$ is OAc; $R_9$ is OH; $R_{10}$ is OH; X, $X_1$ and $X_2$ are O then $R_5$ is different from OAc; and R, $R_4$ and $R_6$ are H; $R_7$ is OH; $R_8$ and $R_9$ are Br; $R_{10}$ is OH; X is O; $X_1$ and $X_2$ are O then $R_5$ is different from OH; and R, $R_4$ and $R_6$ are H; $R_7$ is OH or OAc; $R_8$ and $R_9$ are F; $R_{10}$ is OH or OAc; X is O; $X_1$ and $X_2$ are O then $R_5$ is different from OH; and R, $R_4$, $R_6$, $R_8$, and $R_9$ are H; $R_7$ is OH or OAc; $R_{10}$ is OMe; X is O, NHAc, or S; $X_1$ is O, $X_2$ is O, NH, $NCH_3$ or S then $R_5$ is different from OH; and R, $R_4$, $R_7$, and $R_8$ are H; $R_6$ is OH; $R_9$ is F; $R_{10}$ is OH, OMe, OEt or OAc; X, $X_1$, and $X_2$ are O then $R_5$ is different from OH; and R, $R_4$, and $R_7$, are H; $R_6$ is OH; $R_8$ and $R_9$ are F; $R_{10}$ is OH or OAc; X is O; $X_1$ and $X_2$ are O then $R_5$ is different from OH; and R, $R_4$, and $R_7$ are H; $R_6$ is OAc; $R_8$ is Br, $R_9$ is F; $R_{10}$ is OAc; X, $X_1$, and $X_2$ are O then $R_5$ is different from H; and R, $R_6$ and $R_7$, are H; $R_4$ is OH; $R_8$ is F; $R_9$ is Br or Cl; $R_{10}$ is propyloxy; X, $X_1$, and $X_2$ are O then $R_5$ is different from H; and R, $R_4$, $R_6$, and $R_8$ are H; $R_7$ is Br or Cl; $R_9$ is Br, I or F; $R_{10}$ is OMe or OEt; X, $X_1$, and $X_2$ are O then $R_5$ is different from OH; and

86

R, $R_4$, $R_6$, and $R_8$ are H; $R_7$ is Br or I; $R_9$ is F; $R_{10}$ is F or OAc; X, $X_1$, and $X_2$ are O then $R_5$ is different from OAc or COOEt; and R, $R_4$, $R_6$, $R_8$, and $R_9$ are H; $R_7$ is F; $R_{10}$ is OH; X, $X_1$, and $X_2$ are O then $R_5$ is different from OH; and R, $R_4$, $R_6$, $R_7$, and $R_9$ are H; $R_8$ and $R_{10}$ are I; X, $X_1$, and $X_2$ are O then $R_5$ is different from OH;

R, $R_4$, $R_6$, and $R_7$ are H; $R_8$ and $R_9$ are Br, $R_{10}$ is OH; X, $X_1$, and $X_2$ are O then $R_5$ is different from OH;

R, $R_4$, $R_6$, $R_8$, and $R_9$ are H; $R_7$ and $R_{10}$ are OH; X, $X_1$, and $X_2$ are O then $R_5$ is different from OH.

2. The compound of claim 1, wherein the compound is combined with a pharmaceutically acceptable carrier or excipient.

3. A method of treating a viral infection caused by Epstein-Barr virus (EBV) in a mammal, the method comprising administering to the mammal in need thereof, a therapeutically effective amount of a compound of formula 1C:

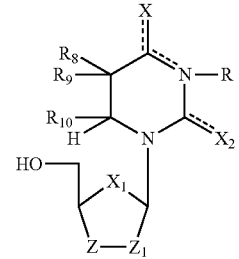

wherein:

X is =O, =S, N=CH—N($CH_3$)$_2$ hydroxyl, alkoxy, thiol, acyloxy, amino, substituted amino, aminoacyl, or aminoacyloxy;

$X_1$ is O or S;

$X_2$ is =O, =S, hydroxyl, thiol, alkoxy, amino or substituted amino;

R is H, alkyl, substituted alkyl, acyl, acylamino, or alkyl-carboxy with the proviso that R is not present when X is hydroxyl, thiol, alkoxy, amino or substituted amino;

$R_8$ is H, halogen, or hydroxyl;

$R_9$ is H, halogen, $C_1$-$C_6$ alkyl or $C_1$-$C_6$ substituted alkyl;

$R_{10}$ is halogen, hydroxy, $C_1$ $C_{18}$ alkoxy, acyloxy, or azido; and

Z—$Z_1$ is selected from the groups consisting of $CR_4R_5$—$CR_6R_7$ (wherein $R_4$, $R_5$, $R_6$, and $R_7$ are independently selected from H, OH, halogens, cyano, $N_3$, $CH_2OH$, COOH, $C_1$-$C_4$ alkyl substituted carboxy, $NH_2$, $CH_2NH_2$, $CH_2COOH$, $C_1$-$C_3$ thioalkyl, thiol, $ONO_2$, $ONH_2$, $CF_3$, $NO_2$, CNS, NHCN, $CH_2N_3$, NH—($C_1$-$C_1$ alkyl), CHO, C=CH, alkoxy, or $OCH_2$aryl), CR=CH, S—$CH_2$, O—CFH, or $C(R^{27})=C(R^2)$ (wherein $R^{27}$ and $R^{28}$ are, independently of each other, selected from H, OH, halogen, or azido), and derivatives thereof wherein —OH and/or —$NH_2$ groups are protected with phosphates or phosphoesters.

4. A method of treating a viral infection caused by hepatitis B virus (HBV) in a mammal, the method comprising administering to the mammal in need thereof, a therapeutically effective amount of a compound of formula 1 C:

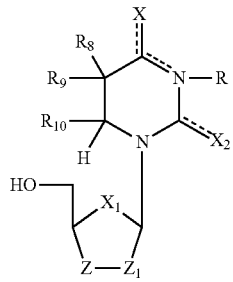

wherein:
X is =O, =S, N=CH—N(CH$_3$)$_2$, hydroxyl, alkoxy, thiol, acyloxy, amino, substituted amino, aminoacyl, or aminoacyloxy;

X$_1$ is O or S;

X$_2$ is =O, =S, hydroxyl, thiol, alkoxy, amino or substituted amino;

R is H, alkyl, substituted alkyl, acyl, acylamino, or alkylcarboxy with the proviso that R is not present when X is hydroxyl, thiol, alkoxy, amino or substituted amino;

R$_8$ is H, halogen, or hydroxyl;

R$_9$ is H, halogen, C$_2$-C$_6$ alkyl or C$_1$-C$_6$ substituted alkyl;

R$_{10}$ is halogen, hydroxy, C$_1$-C$_{18}$ alkoxy, acyloxy, or azido; and

Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-C$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), CH=CH, S—CH$_2$, O—CH$_2$, or C(R$^{27}$)=C(R$^{28}$) (wherein R$^{27}$ and R$^{28}$ are, independently of each other, selected from H, OH, halogen, or azido), and derivatives thereof wherein —OH and/or —NH$_2$ groups are protected with phosphates or phosphoesters.

5. The method according to claim 3 or 4, wherein the mammal is a human.

6. The method according to claim 5, wherein the compound is administered in combination with a pharmaceutically acceptable carrier or excipient.

7. The method according to claim 3 or 4, wherein X is =O, =S or aminoacyl; X$_1$ is O; X$_2$ is =O or =S, R is H, C$_1$-C$_6$ alkyl, R$_8$ is H or halogen, R$_9$ is H or halogen, R$_{10}$ is hydroxy, C$_1$-C$_{18}$ alkoxy, acyloxy or azido, Z—Z$_1$ is selected from the groups consisting of CR$_4$R$_5$—CR$_6$R$_7$ [wherein R$_4$, R$_8$, R$_6$, and R$_7$ are independently selected from H, OH, halogens, cyano, N$_3$, NH$_2$, NH—(C$_1$-C$_4$ alkyl), C$_3$-C$_2$ alkoxy, or OCH$_2$aryl], CH—CH, and derivatives thereof wherein —OH and/or —NH$_2$ groups are protected with phosphates or phosphoesters.

8. A method of treating a viral infection caused by a herpes simplex virus in a mammal, the method comprising administering to the mammal in need thereof, a therapeutically effective amount of a compound of formula 1C:

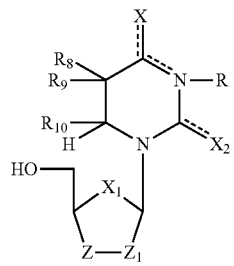

wherein:
X is =O, =S, N=CH—N(CH$_3$)$_2$, hydroxyl, alkoxy, thiol, acyloxy, amino, substituted amino, aminoacyl, or aminoacyloxy;

X$_1$ is O or S;

X$_2$ is =O, =S, hydroxyl, thiol, alkoxy, amino or substituted amino;

R is H, alkyl, substituted alkyl, acyl, acylamino, or alkylcarboxy, with the proviso that R is not present when X is hydroxyl, thiol, alkoxy, amino or substituted amino;

R$_8$ is H or halogen;

R$_9$ is H or halogen;

R$_{10}$ is hydroxy, alkoxy, acyloxy, or azido; and

Z—Z$_1$ is selected from the groups consisting of CR$_4$R$_5$—CR$_6$R$_7$ (wherein R$_4$, R$_5$, R$_6$, and R$_7$ are independently selected from H, OH, halogens, cyano, N$_3$, CH$_2$OH, COOH, C$_1$-C$_4$ alkyl substituted carboxy, NH$_2$, CH$_2$NH$_2$, CH$_2$COOH, C$_1$-O$_3$ thioalkyl, thiol, ONO$_2$, ONH$_2$, CF$_3$, NO$_2$, CNS, NHCN, CH$_2$N$_3$, NH—(C$_1$-C$_4$ alkyl), CHO, C=CH, C$_1$-C$_4$ alkoxy, or OCH$_2$aryl), and derivatives thereof wherein —OH and/or —NH$_2$ groups are protected with phosphates or phosphoesters.

9. The method according to claim 8, wherein the mammal is a human.

10. The method according to claim 9, wherein the compound is administered in combination with a pharmaceutically acceptable carrier or excipient.

11. A method of treating a viral infection caused by a virus selected from the group consisting of Hepatitis B (HBV) and Esptein-Barr (EBV) viruses in a mammal, the method comprising administering to the mammal in need thereof, a therapeutically effective amount of a compound of formula:

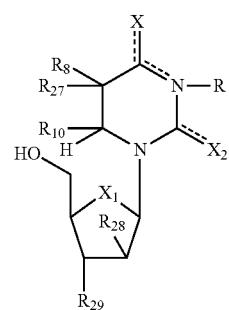

wherein:

X is =O, =S, N=CH—N(CH$_3$)$_2$, hydroxyl, alkoxy, thiol, acyloxy, amino, substituted amino, aminoacyl, or aminoacyloxy;

X$_1$ is O or S;

X$_2$ is =O, =S, hydroxyl, alkoxy, amino or substituted amino;

R is H, alkyl, substituted alkyl, acyl, acylamino, or alkylcarboxy, with the proviso that R is not present when X is hydroxyl, thiol, alkoxy, amino or substituted amino;

R$_8$ is H, halogen, or hydroxyl;

R$_{10}$ is hydroxy, C$_1$-C$_{18}$ alkoxy, acyloxy, or azido;

R$_{27}$ is C$_1$-C$_6$ alkyl, or C$_1$-C$_6$ substituted alkyl;

R$_{28}$ is halogen, hydroxyl, azido or cyano; and

R$_{29}$ is hydroxy, C$_1$-C$_3$ alkoxy, amino, or substituted amino.

12. The method according to claim 11, wherein the virus is HBV.

13. The method according to claim 11, wherein the virus is EBV.

14. The method according to claim 11, wherein the mammal is a human.

15. The method according to claim 14, wherein the compound is administered in combination with a pharmaceutically acceptable carrier or excipient.

16. The method according to claim 11, wherein X is =O, =S or aminoacyl; X$_1$ is O; X$_2$ is =O or =S. R is H, C$_1$-C$_6$ alkyl, R$_8$ is H or halogen, R$_{10}$ is H, hydroxy, C$_1$-C$_{18}$ alkoxy, acyloxy or azido, R$_{27}$ is alkyl or C$_{1-3}$ substituted alkyl, R$_{28}$ is halogen, hydroxy, or azido: R$_{29}$ is hydroxy or amino: and derivatives thereof wherein —OH and/or —NH$_2$ groups are protected with phosphates or phosphoesters.

17. A compound of the formula:

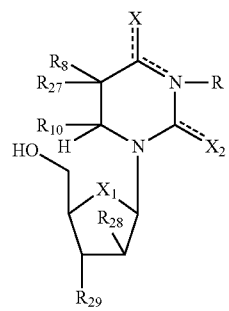

wherein:

X is =O, =S, N=CH—N(CH$_3$)$_2$, hydroxyl, alkoxy, thiol, acyloxy, amino, substituted amino, aminoacyl, or aminoacyloxy;

X$_1$ is O or S:

X$_2$ is =O, =S, hydroxyl, thiol, alkoxy, amino or substituted amino;

R is H, alkyl, substituted alkyl, acyl, acylamino, or alkylcarboxy, with the proviso that R is not present when X is hydroxyl, thiol, alkoxy, amino or substituted amino;

R$_8$ is H, halogen, or hydroxyl;

R$_{10}$ is H, halogen, hydroxy, C$_1$-C$_{18}$ alkoxy, acyloxy, or azido;

R$_{27}$ is C$_1$-C$_6$ alkyl, or C$_1$-C$_6$ substituted alkyl;

R$_{28}$ is halogen, hydroxyl, azido or cyano; and

R$_{29}$ is hydroxy, C$_1$-C$_3$ alkoxy, amino, or substituted amino.

18. The compound of claim 17, wherein the compound is combined with a pharmaceutically acceptable carrier or excipient.

* * * * *